US010155796B2

(12) United States Patent
Greene et al.

(10) Patent No.: US 10,155,796 B2
(45) Date of Patent: *Dec. 18, 2018

(54) COMPOSITIONS AND METHODS FOR INHIBITING TUMOR CELLS BY INHIBITING THE TRANSCRIPTION FACTOR ATF5

(71) Applicants: The Trustees of Columbia University in the City of New York, New York, NY (US); The Regents of the University of California, Oakland, CA (US)

(72) Inventors: Lloyd A. Greene, Larchmont, NY (US); James Angelastro, Davis, CA (US)

(73) Assignees: The Trustees of Columbia University in the City of New York, New York, NY (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/661,699

(22) Filed: Jul. 27, 2017

(65) Prior Publication Data
US 2018/0002389 A1    Jan. 4, 2018

Related U.S. Application Data

(63) Continuation of application No. 15/418,247, filed on Jan. 27, 2017, now Pat. No. 9,758,555, which is a continuation of application No. 14/830,194, filed on Aug. 19, 2015, which is a continuation of application No. PCT/US2014/017550, filed on Feb. 21, 2014.

(60) Provisional application No. 61/768,390, filed on Feb. 22, 2013.

(51) Int. Cl.
| *C07K 14/47* | (2006.01) |
| *A61K 38/00* | (2006.01) |
| *A61K 31/495* | (2006.01) |
| *A61K 38/17* | (2006.01) |

(52) U.S. Cl.
CPC ........ *C07K 14/4705* (2013.01); *A61K 31/495* (2013.01); *A61K 38/1709* (2013.01); *A61K 38/00* (2013.01)

(58) Field of Classification Search
CPC ............................ C07K 14/4705; A61K 38/00
See application file for complete search history.

(56) References Cited

U.S. PATENT DOCUMENTS

| 5,942,433 | A | * | 8/1999 | Vinson | C12N 15/11 435/320.1 |
| 5,955,593 | A | * | 9/1999 | Korsmeyer | C07K 14/4747 435/69.1 |
| 5,998,583 | A | * | 12/1999 | Korsmeyer | C07K 14/4747 424/185.1 |
| 6,221,355 | B1 | * | 4/2001 | Dowdy | C07K 14/005 424/192.1 |
| 6,303,576 | B1 | * | 10/2001 | Blaschuk | C07K 7/06 435/5 |
| 6,361,968 | B1 | * | 3/2002 | Vinson | C07K 14/4702 435/69.1 |
| 6,468,754 | B1 | * | 10/2002 | Greene | C12N 9/00 435/320.1 |
| 6,485,977 | B1 | * | 11/2002 | Collmer | C07K 14/005 435/320.1 |
| 7,888,326 | B2 | | 2/2011 | Greene et al. | |
| 8,158,420 | B2 | | 4/2012 | Greene et al. | |
| 2007/0092495 | A1 | | 4/2007 | Greene et al. | |
| 2012/0093919 | A1 | | 4/2012 | Bertino, Jr. et al. | |
| 2012/0238462 | A1 | | 9/2012 | Greene et al. | |

FOREIGN PATENT DOCUMENTS

| JP | 2010-512730 A | 4/2010 |
| WO | WO 2008/072777 A2 | 6/2008 |
| WO | WO2008/151037 | 12/2008 |
| WO | WO 2011/097513 A1 | 8/2011 |
| WO | WO 2013/013105 A2 | 1/2013 |

OTHER PUBLICATIONS

Acharya et al., Experimental identification of homodimerizing B-ZIP families in *Homo sapiens*, J. Struct. Biol. 155:130-139, 2006.
Angelastro et al., Downregulation of ATF 5 Is Required for Differentiation of Neural Progenitor Cells into Astrocytes, J. Neurosci. 25:3889-3899, 2005.
Angelastro et al., Selective destruction of glioblastoma cells by interference with the activity or expression of ATF5, Oncogene 25:907-916, 2006.
Ciaccio et al., High-yield expression in *E. coli* and refolding of the bZIP domain of activating transcription factor 5, Protein Expr. Purif. 62:235-243, 2008.
Ciaccio et al., Influence of the Valine Zipper Region on the Structure and Aggregation of the Basic Leucine Zipper (bZIP) Domain of ATF5, Mol. Pharm. 9:3190-3199, 2012.
Greene et al., The transcription factor ATF5: role in neurodevelopment and neural tumors, J. Neurochem. 108:11-22, 2009.
Krylov et al., Extending dimerization interfaces: the bZIP basic region can form a colied coil, EMBO J. 14:5329-5337, 1995.
Krylov et al., A general method to design dominant negatives to B-HLHZip proteins that abolish DNA binding, Proc. Natl. Acad. Sci., USA 94:12274-12279, 1997.
Lee et al., Reciprocal Actions of ATF5 and Shh in Proliferation of Cerebellar Granule Neuron Progenitor Cells, Dev. Neurobiol. 72:789-804, 2012.

(Continued)

*Primary Examiner* — Amber D Steele
(74) *Attorney, Agent, or Firm* — Baker Botts L.L.P.

(57) ABSTRACT

The present invention relates to methods for treating and/or preventing tumors and/or promoting apoptosis in a neoplastic cell comprising contacting the neoplastic cell with an cell-penetrating dominant-negative ATF5 ("CP-d/n-ATF5"), wherein the CP-d/n-ATF5 is capable of inhibiting ATF5 function and/or activity.

30 Claims, 31 Drawing Sheets

Specification includes a Sequence Listing.

(56) References Cited

OTHER PUBLICATIONS

Li, et al., Identification of a Novel DNA Binding Site and a Transcriptional Target for ATF5 in C6 Glioma and MCF-7 Breast Cancer Cells, Mol. Cancer Res. 7:933-943, 2009.
Mason et al., ATF5 regulates the proliferation and differentiation of oligodendrocytes, Mol. Cell. Neurosci. 29:372-380, 2005.
Monaco et al., The transcription factor ATF5 is widely expressed in carcinomas, and interference with its function selectively kills . . . , Int. J. Cancer 120:1883-1890, 2007.
Olive et al., A Dominant Negative to Activation Protein-1 (API) That Abolishes DNA Binding and Inhibits Oncogenesis, J. Biol. Chem. 272:18586-18594, 1997.
Arias et al. "Regulated ATF5 loss-of-function in adult mice blocks formation and causes regression/eradication of gliomas," Oncogene 31(6):739-751 (Jul. 4, 2011).
Dluzen et al., "BCL-2 Is a Downstream Target of ATF5 That Mediates the Prosurvival Function of ATF5 in a Cell Type-dependent Manner," Journal Of Biological Chemistry 286(9):7705-7713 (Mar. 4, 2011).
Supplementary European Search Report dated Jun. 30, 2016 in International Application No. EP 14754450.
International Search report dated Jun. 9, 2014 in International Application No. PCT/US14/17550.
Moll, J et al. "Attractive Interhelical Electrostatic Interactions In the Proline- and Acidic-Rich Region (PAR) Leucine Zipper subfamily Preclude Heterodimerization With Other Basic Leucine Zipper Subfamilies" Journal of Biological Chemistry. Nov. 3, 2000, vol. 275, No. 44; pp. 34826-34832; p. 34827.

* cited by examiner

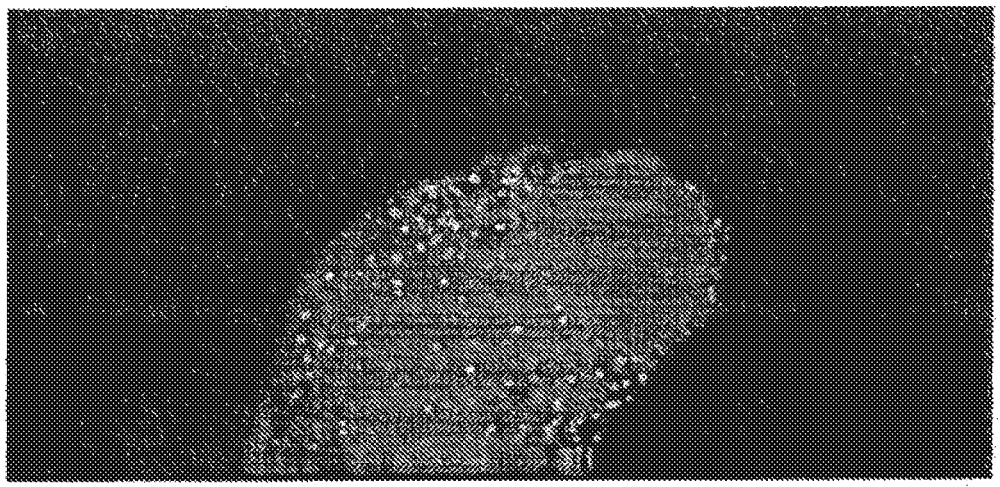
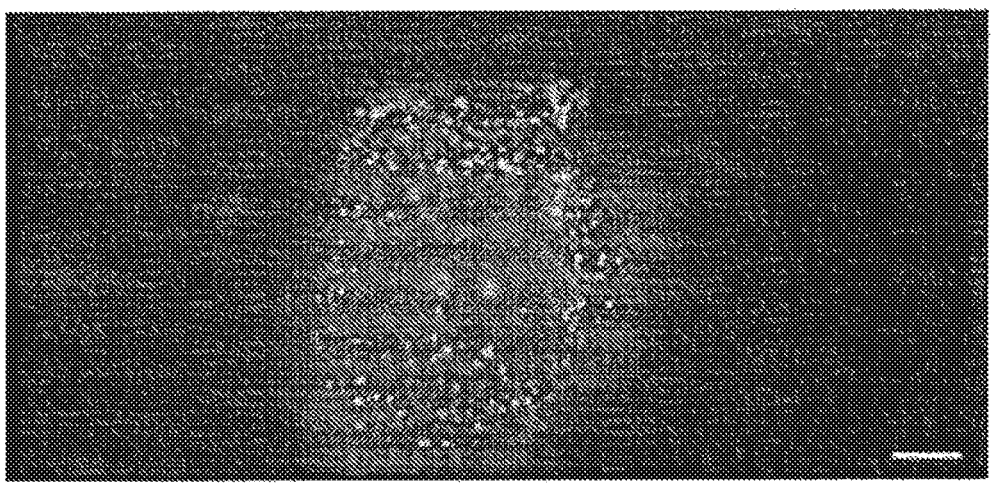
FIG. 3A

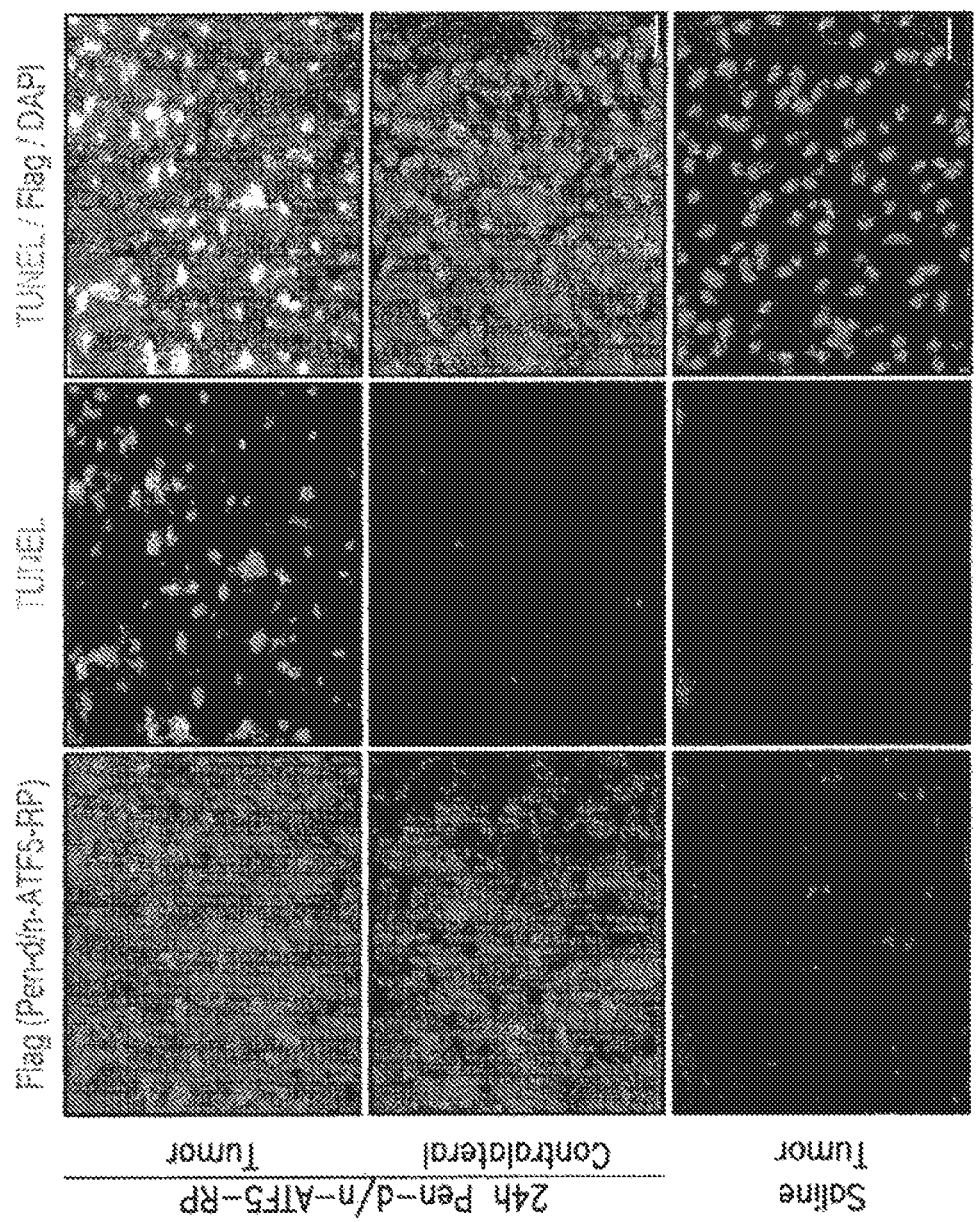

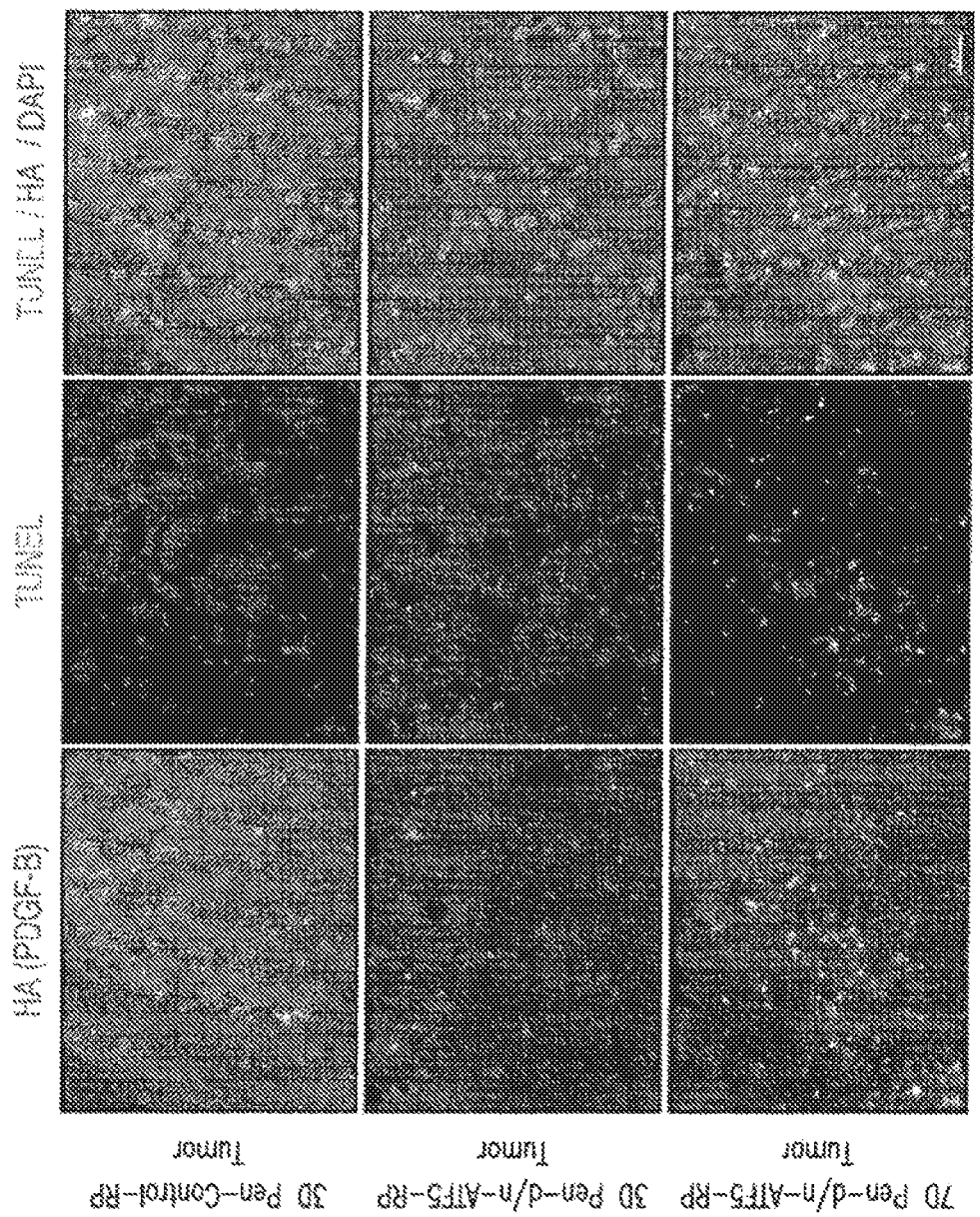

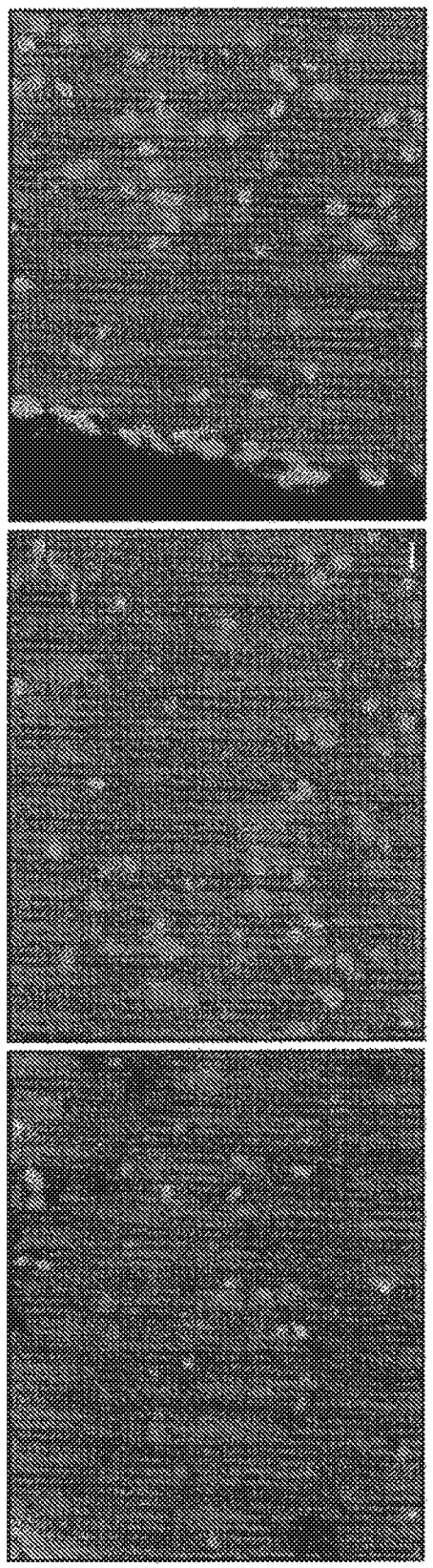

Lateral Ventricle | Hippocampal DG

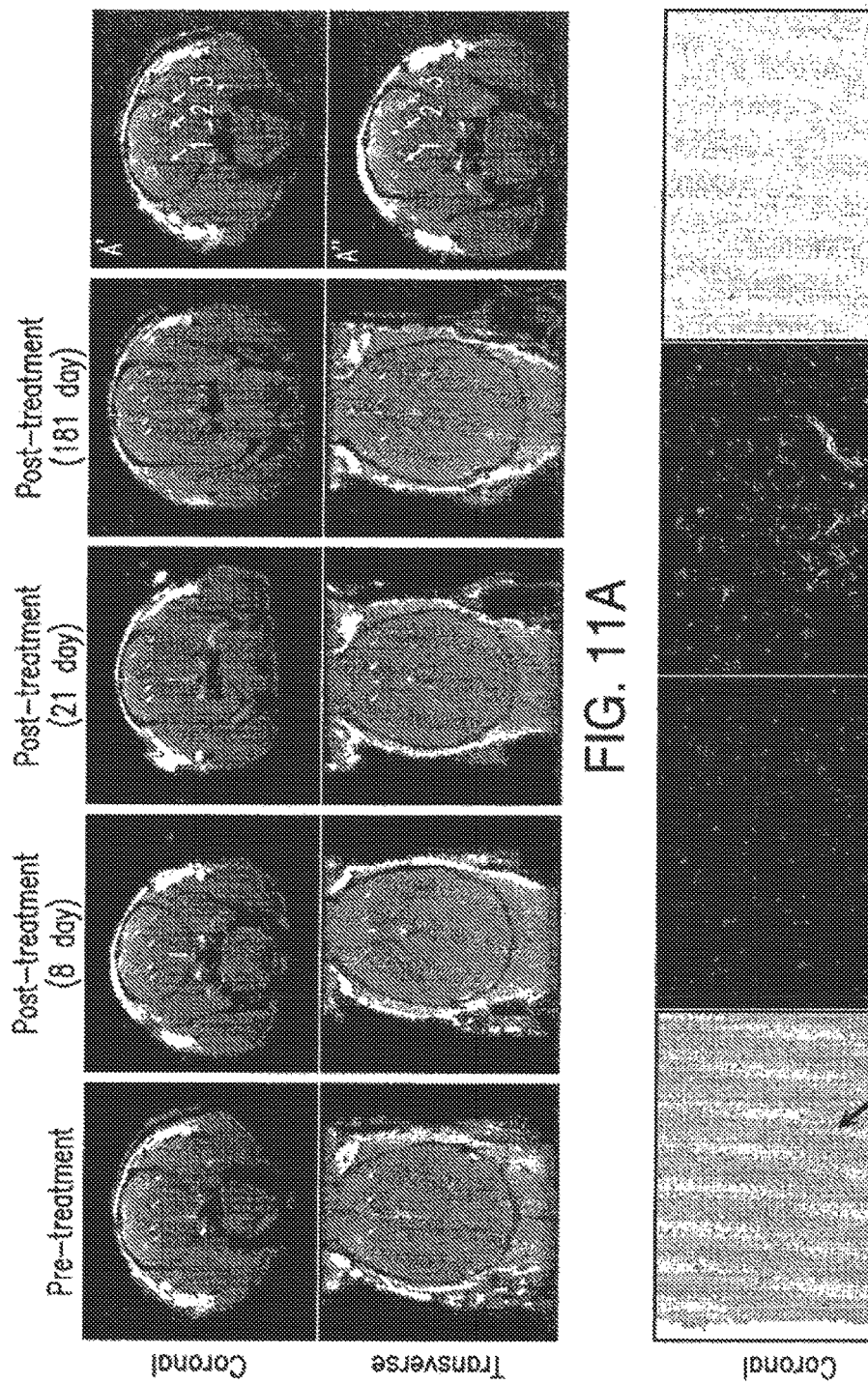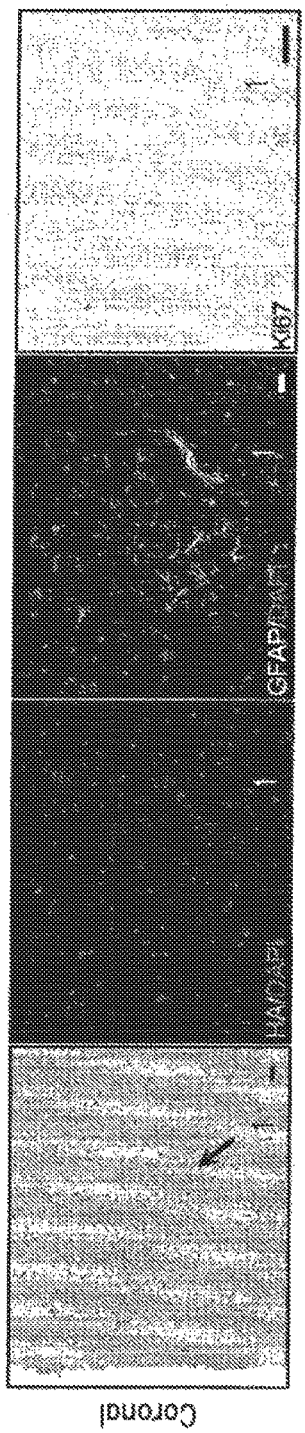

SEQUENCE LISTING

```
<160> NUMBER OF SEQ ID NOS: 55

<210> SEQ ID NO 1
<211> LENGTH: 7
<212> TYPE: PRT
<213> ORGANISM: Unknown
<220> FEATURE:
<223> OTHER INFORMATION: Description of Unknown: ATF5
      peptide sequence

<400> SEQUENCE: 1

Leu Glu Gln Glu Asn Ala Glu
1               5

<210> SEQ ID NO 2
<211> LENGTH: 14
<212> TYPE: PRT
<213> ORGANISM: Unknown
<220> FEATURE:
<223> OTHER INFORMATION: Description of Unknown: ATF5
      peptide sequence

<400> SEQUENCE: 2

Leu Glu Lys Glu Ala Glu Glu Leu Glu Gln Glu Asn Ala Glu
1               5                   10

<210> SEQ ID NO 3
<211> LENGTH: 22
<212> TYPE: PRT
<213> ORGANISM: Unknown
<220> FEATURE:
<223> OTHER INFORMATION: Description of Unknown: ATF5
      peptide sequence

<400> SEQUENCE: 3

Leu Ala Arg Glu Asn Glu Glu Leu Leu Glu Lys Glu Ala Glu Glu Leu
1               5                   10                  15

Glu Gln Glu Asn Ala Glu
            20

<210> SEQ ID NO 4
<211> LENGTH: 29
<212> TYPE: PRT
<213> ORGANISM: Unknown
<220> FEATURE:
<223> OTHER INFORMATION: Description of Unknown: ATF5
      peptide sequence

<400> SEQUENCE: 4
```

Leu Glu Gln Arg Ala Glu Glu Leu Ala Arg Glu Asn Glu Glu Leu Leu
1               5                   10                  15

Glu Lys Glu Ala Glu Glu Leu Glu Gln Glu Asn Ala Glu
            20                  25

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Glu Gln Glu Asn Ala Glu Leu Glu Gly Glu Cys Gln Gly Leu Glu
1               5                   10                  15

Ala Arg Asn Arg Glu Leu Lys Glu Arg Ala Glu Ser
            20                  25

<210> SEQ ID NO 6
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Leu Glu Lys Glu Ala Glu Glu Leu Glu Gln Glu Asn Ala Glu Leu Glu
1               5                   10                  15

Gly Glu Cys Gln Gly Leu Glu Ala Arg Asn Arg Glu Leu Lys Glu Arg
            20                  25                  30

Ala Glu Ser
        35

<210> SEQ ID NO 7
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Leu Ala Arg Glu Asn Glu Glu Leu Leu Glu Lys Glu Ala Glu Glu Leu
1               5                   10                  15

Glu Gln Glu Asn Ala Glu Leu Glu Gly Glu Cys Gln Gly Leu Glu Ala
            20                  25                  30

Arg Asn Arg Glu Leu Lys Glu Arg Ala Glu Ser
        35                  40

<210> SEQ ID NO 8
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Glu Gln Arg Ala Glu Glu Leu Ala Arg Asn Glu Glu Leu Leu Glu
1               5                   10                  15

Lys Glu Ala Glu Glu Leu Glu Gln Glu Asn Ala Glu Leu Glu Gly Glu

Cys Gln Gly Leu Glu Ala Arg Asn Arg Glu Leu Lys Glu Arg Ala Glu
                35                  40                  45

Ser

<210> SEQ ID NO 9
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Leu Glu Gln Arg Ala Glu Glu Leu Ala Arg Glu Asn Glu Glu Leu Leu
1               5                   10                  15

Glu Lys Glu Ala Glu Glu Leu Glu Gln Glu Asn Ala Glu Leu Glu Gly
                20                  25                  30

Glu Cys Gln Gly Leu Glu Ala Arg Asn Arg Glu Leu Lys Glu Arg Ala
                35                  40                  45

Glu Ser Val
    50

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Glu Gln Glu Asn Ala Glu Leu Glu Gly Glu Cys Gln Gly Leu Glu
1               5                   10                  15

Ala Arg Asn Arg Glu Leu Arg Glu Arg Ala Glu Ser
                20                  25

<210> SEQ ID NO 11
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Leu Glu Lys Glu Ala Glu Glu Leu Glu Gln Glu Asn Ala Glu Leu Glu
1               5                   10                  15

Gly Glu Cys Gln Gly Leu Glu Ala Arg Asn Arg Glu Leu Arg Glu Arg
                20                  25                  30

Ala Glu Ser
        35

<210> SEQ ID NO 12
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Leu Ala Arg Glu Asn Glu Glu Leu Leu Glu Lys Glu Ala Glu Glu Leu

```
                1               5                  10                  15
Glu Gln Glu Asn Ala Glu Leu Glu Gly Glu Cys Gln Gly Leu Glu Ala
                20                  25                  30

Arg Asn Arg Glu Leu Arg Glu Arg Ala Glu Ser
                35                  40

<210> SEQ ID NO 13
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Leu Glu Gln Arg Ala Glu Glu Leu Ala Arg Glu Asn Glu Glu Leu Leu
1               5                   10                  15

Glu Lys Glu Ala Glu Glu Leu Glu Gln Glu Asn Ala Glu Leu Glu Gly
                20                  25                  30

Glu Cys Gln Gly Leu Glu Ala Arg Asn Arg Glu Leu Arg Glu Arg Ala
                35                  40                  45

Glu Ser
    50

<210> SEQ ID NO 14
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Leu Glu Gln Arg Ala Glu Glu Leu Ala Arg Glu Asn Glu Glu Leu Leu
1               5                   10                  15

Glu Lys Glu Ala Glu Glu Leu Glu Gln Glu Asn Ala Glu Leu Glu Gly
                20                  25                  30

Glu Cys Gln Gly Leu Glu Ala Arg Asn Arg Glu Leu Arg Glu Arg Ala
                35                  40                  45

Glu Ser Val
    50

<210> SEQ ID NO 15
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Ser Ser His His His His His His Ser Ser Gly Leu Val Pro
1               5                   10                  15

Arg Gly Ser His Met Arg Gln Ile Lys Ile Trp Phe Gln Asn Arg Arg
                20                  25                  30

Met Lys Trp Lys Lys Asp Tyr Lys Asp Asp Asp Lys Met Ala Ser
                35                  40                  45

Met Thr Gly Gly Gln Gln Met Gly Arg Asp Pro Asp Leu Glu Gln Arg
    50                  55                  60

Ala Glu Glu Leu Ala Arg Glu Asn Glu Glu Leu Leu Glu Lys Glu Ala
65                  70                  75                  80
```

Glu Leu Glu Gln Glu Asn Ala Glu Leu Glu Gly Glu Cys Gln Gly
            85                  90                  95

Leu Glu Ala Arg Asn Arg Glu Leu Arg Glu Arg Ala Glu Ser Val
        100                 105                 110

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 16

His His His His His His
1               5

<210> SEQ ID NO 17
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gly Ser Ser His His His His His Ser Ser Gly Leu Val Pro
1               5                   10                  15

Arg Gly Ser His Met Leu Glu Tyr Gly Arg Lys Lys Arg Gln Arg
                20                  25                  30

Arg Arg Tyr Pro Tyr Asp Val Pro Asp Tyr Ala Met Ala Ser Met Thr
                35                  40                  45

Gly Gly Gln Gln Met Gly Arg Asp Pro Asp Leu Glu Gly Arg Ala Glu
        50                  55                  60

Glu Leu Ala Arg Glu Asn Glu Glu Leu Leu Lys Glu Ala Glu Glu
65                  70                  75                  80

Leu Glu Gln Glu Asn Ala Glu Leu Glu Gly Glu Cys Gln Gly Leu Glu
                85                  90                  95

Ala Arg Asn Arg Glu Leu Arg Glu Arg Ala Glu Ser Val
            100                 105

<210> SEQ ID NO 18
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gly Ser Ser His His His His His Ser Ser Gly Leu Val Pro
1               5                   10                  15

Arg Gly Ser His Met Arg Gln Ile Lys Ile Trp Phe Gln Asn Arg Arg
                20                  25                  30

Met Lys Trp Lys Lys Leu Glu Gln Arg Ala Glu Glu Leu Ala Arg Glu
        35                  40                  45

Asn Glu Glu Leu Leu Glu Lys Glu Ala Glu Glu Leu Glu Gln Glu Asn
        50                  55                  60

Ala Glu Leu Glu Gly Glu Cys Gln Gly Leu Glu Ala Arg Asn Arg Glu
65                  70                  75                  80

```
Leu Lys Glu Arg Ala Glu Ser Val
                85

<210> SEQ ID NO 19
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Arg Gln Ile Lys Ile Trp Phe Gln Asn Arg Arg Met Lys Trp Lys Lys
1               5                   10                  15

Leu Glu Gln Arg Ala Glu Glu Leu Ala Arg Glu Asn Glu Glu Leu Leu
            20                  25                  30

Glu Lys Glu Ala Glu Glu Leu Glu Gln Glu Asn Ala Glu Leu Glu Gly
        35                  40                  45

Glu Cys Gln Gly Leu Glu Ala Arg Asn Arg Glu Leu Lys Glu Arg Ala
    50                  55                  60

Glu Ser Val
65

<210> SEQ ID NO 20
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctggaacagg aaaacgcgga actggaaggc gaatgccagg gcctggaagc gcgcaaccgc     60
gaactgaaag aacgcgcgga aagctaa                                        87

<210> SEQ ID NO 21
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
ctggaaaaag aagcggaaga actggaacag gaaaacgcgg aactggaagg cgaatgccag     60
ggcctggaag cgcgcaaccg cgaactgaaa gaacgcgcgg aaagctaa                 108

<210> SEQ ID NO 22
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ctggcgcgcg aaaacgaaga actgctggaa aagaagcgg aagaactgga acaggaaaac      60
gcggaactgg aaggcgaatg ccagggcctg gaagcgcgca accgcgaact gaaagaacgc    120
gcggaaagct aa                                                        132

<210> SEQ ID NO 23
<211> LENGTH: 50
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Leu Glu Gln Arg Ala Glu Glu Leu Ala Arg Glu Asn Glu Glu Leu Leu
1               5                   10                  15
Glu Lys Glu Ala Glu Glu Leu Glu Gln Glu Asn Ala Glu Leu Glu Gly
            20                  25                  30
Glu Cys Gln Gly Leu Glu Ala Arg Asn Arg Glu Leu Lys Glu Arg Ala
        35                  40                  45
Glu Ser
    50

<210> SEQ ID NO 24
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
ctggaacagc gcgcggaaga actggcgcgc gaaaacgaag aactgctgga aaaagaagcg      60
gaagaactgg aacaggaaaa cgcggaactg gaaggcgaat gccagggcct ggaagcgcgc     120
aaccgcgaac tgaaagaacg cgcggaaagc taa                                  153

<210> SEQ ID NO 25
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ctggaacagc gcgcggaaga actggcgcgc gaaaacgaag aactgctgga aaaagaagcg      60
gaagaactgg aacaggaaaa cgcggaactg gaaggcgaat gccagggcct ggaagcgcgc     120
aaccgcgaac tgaaagaacg cgcggaaagc gtgtaa                               156

<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Glu Gly Glu Cys Gln Gly Leu Glu Ala Arg Asn Arg Glu Leu Lys
1               5                   10                  15
Glu Arg Ala Glu Ser Val
            20

<210> SEQ ID NO 27
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctggaacagg aaaacgcgga actggaaggc gaatgccagg gcctggaagc gcgcaaccgc    60
gaactgcgcg aacgcgcgga aagctaa    87

<210> SEQ ID NO 28
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
ctggaaaaag aagcggaaga actggaacag gaaaacgcgg aactggaagg cgaatgccag    60
ggcctggaag cgcgcaaccg cgaactgcgc gaacgcgcgg aaagctaa    108

<210> SEQ ID NO 29
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
ctggcgcgcg aaaacgaaga actgctggaa aaagaagcgg aagaactgga acaggaaaac    60
gcggaactgg aaggcgaatg ccagggcctg gaagcgcgca accgcgaact gcgcgaacgc    120
gcggaaagct aa    132

<210> SEQ ID NO 30
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
ctggaacagc gcgcggaaga actggcgcgc gaaaacgaag aactgctgga aaaagaagcg    60
gaagaactgg aacaggaaaa cgcggaactg gaaggcgaat gccagggcct ggaagcgcgc    120
aaccgcgaac tgcgcgaacg cgcggaaagc taa    153

<210> SEQ ID NO 31
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
ctggaacagc gcgcggaaga actggcgcgc gaaaacgaag aactgctgga aaaagaagcg    60
gaagaactgg aacaggaaaa cgcggaactg gaaggcgaat gccagggcct ggaagcgcgc    120
aaccgcgaac tgcgcgaacg cgcggaaagc gtgtaa    156

<210> SEQ ID NO 32
<211> LENGTH: 22
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 32

Leu Glu Gly Glu Cys Gln Gly Leu Glu Ala Arg Asn Arg Glu Leu Arg
1               5                   10                  15

Glu Arg Ala Glu Ser Val
            20

<210> SEQ ID NO 33
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Arg Glu Ile Gln Tyr Val Lys Asp Leu Leu Ile Glu Val Tyr Lys
1               5                   10                  15

Ala Arg Ser Gln Arg Thr Arg Ser
            20

<210> SEQ ID NO 34
<211> LENGTH: 16
<212> TYPE: PRT
<213> ORGANISM: Drosophila sp.

<400> SEQUENCE: 34

Arg Gln Ile Lys Ile Trp Phe Gln Asn Arg Arg Met Lys Trp Lys Lys
1               5                   10                  15

<210> SEQ ID NO 35
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atgggcagca gccatcatca tcatcatcac agcagcggcc tggtgccgcg cggcagccat     60
atgcgtcaaa ttaaaatttg gtttcaaaat cgtcgtatga atggaaaaaa agactacaag    120
gacgatgatg acaaaatggc atctatgact ggaggacaac aaatgggaag agacccagac    180
ctcgaacaaa gagcagaaga actagcaaga gaaaacgaag aactactaga aaagaagca    240 gaagaactag aacaagaaaa tgcagagcta gagggcgagt gccaagggct agaggcgcgg    300
aatcgggagc tgagggagag ggcagagtca gtgtag                              336

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Arg Leu Arg Arg Leu Leu Arg Arg Leu Leu Arg Arg Leu Arg Arg
1               5                   10                  15

<210> SEQ ID NO 37
```

```
<211> LENGTH: 12
<212> TYPE: PRT
<213> ORGANISM: Rabies virus

<400> SEQUENCE: 37

Arg Val Gly Arg Arg Arg Arg Arg Arg Arg Arg
1               5                   10

<210> SEQ ID NO 38
<211> LENGTH: 27
<212> TYPE: PRT
<213> ORGANISM: Unknown
<220> FEATURE:
<223> OTHER INFORMATION: Description of Unknown: Transportan
      peptide

<400> SEQUENCE: 38

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 39
<211> LENGTH: 16
<212> TYPE: PRT
<213> ORGANISM: Rattus sp.

<400> SEQUENCE: 39

Pro Val Ile Arg Val Trp Phe Gln Asn Lys Arg Cys Lys Asp Lys Lys
1               5                   10                  15

<210> SEQ ID NO 40
<211> LENGTH: 11
<212> TYPE: PRT
<213> ORGANISM: Human immunodeficiency virus

<400> SEQUENCE: 40

Tyr Gly Arg Lys Lys Arg Arg Gln Arg Arg Arg
1               5                   10

<210> SEQ ID NO 41
<211> LENGTH: 13
<212> TYPE: PRT
<213> ORGANISM: Human immunodeficiency virus

<400> SEQUENCE: 41

Gly Arg Lys Lys Arg Arg Gln Arg Arg Arg Pro Pro Gln
1               5                   10

<210> SEQ ID NO 42
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atgggcagca gccatcatca tcatcatcac agcagcggcc tggtgccgcg cggcagccat      60
atgctcgagt acggccgcaa gaaacgccgc cagcgccgcc gctatccata tgacgtccca     120
gactatgcta tggcatctat gactggagga caacaaatgg gaagagaccc agacctcgaa     180
caaagagcag aagaactagc aagagaaaac gaagaactac tagaaaaaga gcagaagaa      240
```

```
ctagaacaag aaaatgcaga gctagagggc gagtgccaag ggctagaggc gcggaatcgg    300
gagctgaggg agagggcaga gtcagtgtag                                     330
```

<210> SEQ ID NO 43
<211> LENGTH: 16
<212> TYPE: PRT
<213> ORGANISM: Mus sp.

<400> SEQUENCE: 43

```
Leu Leu Ile Ile Leu Arg Arg Arg Ile Arg Lys Gln Ala His Ala His
1               5                   10                  15
```

<210> SEQ ID NO 44
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25
```

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Lys Leu Ala Leu Lys Leu Ala Leu Lys Ala Leu Lys Ala Ala Leu Lys
1               5                   10                  15

Leu Ala
```

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

```
tccgcggccg caccggtcgc c                                              21
```

<210> SEQ ID NO 47
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

```
ctcgaggata tctcagttat ctacactgac tctgccctct ccctcag                  47
```

<210> SEQ ID NO 48
<211> LENGTH: 90
<212> TYPE: DNA

<213> ORGANISM: Artificial Sequence
<220> FEATURE:
<223> OTHER INFORMATION: Description of Artificial Sequence: Synthetic primer

<400> SEQUENCE: 48
ttaattaagc cgccatggat gcgtcaaatt aaaatttggt ttcaaaatcg tcgtatgaaa    60
tggaaaaaaa tggactacaa ggacgatgat    90

<210> SEQ ID NO 49
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ctcgagggat cctcagttat ctacactgac tctgccctct ccctcag    47

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
cccgggcata tgcgtcaaat taaaatttgg ttt    33

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
ctcgagggat cctcagttat ctagtctggg tctcttcc    38

<210> SEQ ID NO 52
<211> LENGTH: 67
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Arg Gln Ile Lys Ile Trp Phe Gln Asn Arg Arg Met Lys Trp Lys Lys
1               5                   10                  15

Leu Glu Gln Arg Ala Glu Glu Leu Ala Arg Glu Asn Glu Glu Leu Leu
            20                  25                  30

Glu Lys Glu Ala Glu Glu Leu Glu Gln Glu Asn Ala Glu Leu Glu Gly
        35                  40                  45

Glu Cys Gln Gly Leu Glu Ala Arg Asn Arg Glu Leu Arg Glu Arg Ala
    50                  55                  60

Glu Ser Val
65

<210> SEQ ID NO 53
<211> LENGTH: 21

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Glu Gly Glu Cys Gln Gly Leu Glu Ala Arg Asn Arg Glu Leu Lys
1               5                   10                  15

Glu Arg Ala Glu Ser
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Glu Gly Glu Cys Gln Gly Leu Glu Ala Arg Asn Arg Glu Leu Arg
1               5                   10                  15

Glu Arg Ala Glu Ser
            20

<210> SEQ ID NO 55
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Gly Ser Ser His His His His His His Ser Ser Gly Leu Val Pro
1               5                   10                  15

Arg Gly Ser His Met Arg Gln Ile Lys Ile Trp Phe Gln Asn Arg Arg
            20                  25                  30

Met Lys Trp Lys Lys Leu Glu Gln Arg Ala Glu Glu Leu Ala Arg Glu
        35                  40                  45

Asn Glu Glu Leu Leu Glu Lys Glu Ala Glu Glu Leu Glu Gln Glu Asn
    50                  55                  60

Ala Glu Leu Glu Gly Glu Cys Gln Gly Leu Glu Ala Arg Asn Arg Glu
65                  70                  75                  80

Leu Arg Glu Arg Ala Glu Ser Val
                85
```

COMPOSITIONS AND METHODS FOR INHIBITING TUMOR CELLS BY INHIBITING THE TRANSCRIPTION FACTOR ATF5

CROSS-REFERENCE TO RELATED APPLICATIONS

This application is a continuation of U.S. patent application Ser. No. 15/418,247, filed Jan. 27, 2017, which is a continuation of abandoned U.S. patent application Ser. No. 14/830,194, filed Aug. 19, 2015, which is a continuation of International Patent Application No. PCT/US2014/017550, filed Feb. 21, 2014, and claims priority to U.S. Provisional Application Ser. No. 61/768,390, filed Feb. 22, 2013, to all of which priority is claimed and the contents of which are incorporated herein in their entireties.

STATEMENT OF GOVERNMENT INTEREST

This invention was made with government support under Grant No. RCA126924A awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 24, 2017, is 23,000 bytes in size.

1. BACKGROUND OF THE INVENTION

Approximately one million people are diagnosed with cancer each year, and many millions of Americans of all ages are currently living with some form of cancer. At some time during the course of their lifetime, one out of every two American men and one out of every three American women will be diagnosed with some form of cancer. Of the one million Americans diagnosed with cancer annually, 17,000 are diagnosed with brain tumors. Brain tumors invade and destroy normal tissue, producing such effects as impaired sensorimotor and cognitive function, increased intracranial pressure, cerebral edema, and compression of brain tissue, cranial nerves, and cerebral vessels. Drowsiness, lethargy, obtuseness, personality changes, disordered conduct, and impaired mental faculties are the initial symptoms in 25% of patients with malignant brain tumors. Treatment of brain tumors is often multimodal, and depends on pathology and location of the tumors. For malignant gliomas, multimodal therapy, including chemotherapy, radiation therapy, and surgery, is used to try to reduce tumor mass. Regardless of approach, however, prognosis for patients suffering from these tumors is guarded: the median term of survival after chemotherapy, radiation therapy, and surgery is only about 1 year, and only 25% of these patients survive for 2 years.

The prevalence of cancer, and in particular brain tumors refractory to existing therapies, has led to the identification of transcription factors impacting cell cycle control of neuronal cells, including ATF5 (Acharay et al., J Struct Biol 155:130-139 (2006)). ATF5 belongs to the activating transcription factor/CREB family of basic leucine zipper transcription factors (Acharay et al., J Struct Biol 155:130-139 (2006); Greene et al., J Neurochem 108:11-22 (2009)). ATF5 is highly expressed by neural stem and progenitor cells for neuronal and glial lineages and its expression plummets when these differentiate (Angelastro et al., J Neurosci 23:4590-4600 (2003); Angelastro et al., J Neurosci 25:3889-3899 (2005); Mason et al., Mol Cell Neurosci 29:372-380 (2005)). Because constitutive ATF5 expression in neural progenitor cells causes them to remain in cell cycle and blocks their differentiation, (Angelastro et al., J Neurosci 23:4590-4600 (2003); Angelastro et al., J Neurosci 25:3889-3899 (2005); Mason et al., Mol Cell Neurosci 29:372-380 (2005)), ATF5 expression in GBM was assayed as GBMs are thought to be derived from neural stem and progenitor cells (Tanaka et al., Nat Rev Clin Oncol 10:14-26 (2012)). Examination of 29 resected GBMs revealed high ATF5 expression by all and by all 9 rodent and human GBM lines examined (Angelastro et al., Oncogene 25:907-916 (2006)). These findings have been corroborated and additional data has indicated a correlation between ATF5 levels and GBM prognosis (Dong et al., J Neuropathol Exp Neurol 64:948-955 (2005); Sheng et al., Nat Med 16:671-677 (2010)).

To examine the role of ATF5 in GBM, a dominant-negative inhibitor of the protein was created to interfere with ATF5 function (Acharay et al., J Struct Biol 155:130-139 (2006), Angelastro et al., Oncogene 25:907-916 (2006)), and si/shRNAs were developed to silence its expression. Culture experiments with human and rat GBM lines showed that both the d/n-ATF5 and the ATF5 si/shRNAs cause their massive apoptotic death (Angelastro et al., Oncogene 25:907-916 (2006)). In contrast, ATF5+ proliferating neural progenitor cells and astrocytes did not show this apoptotic response. In an initial in vivo study, it was found that if the d/n-ATF5 was retrovirally-delivered it would selectively and with very high efficiency kill tumor cells generated from implanted C6 rat GBM cells, but not normal proliferating brain cells (Angelastro et al., Oncogene 25:907-916 (2006)). In subsequent studies, an adult mouse model was used in which gliomas (of grades ranging form low-grade gliomas to GBMs) are efficiently generated by infection with a retrovirus expressing PDGF-B and a p53 shRNA (Arias et al., Oncogene 31:739-751 (2012)). Using mice engineered to conditionally express the d/n-ATF5 from the human GFAP promoter (which is expressed in neural stem/progenitor cells, astrocytes and GBMs), induction of that d/n-ATF5 led to complete regression/eradication of tumors and survival of all 24 treated mice. Likewise, expression of the d/n-ATF5, prior to injection of the PDGF-B/shRNA-p53 retrovirus, prevented tumor development in 85.7% of the mice. In contrast, for mice in which the d/n-ATF5 was not induced, 15/16 had tumors and 40% died within the test period. There were no apparent effects on normal cells (Arias et al., Oncogene 31:739-751 (2012)).

2. SUMMARY OF THE INVENTION

In certain embodiments, the present invention relates to methods for treating and/or preventing tumors and/or promoting apoptosis in a neoplastic cell comprising contacting the neoplastic cell with an cell-penetrating dominant-negative ATF5 ("CP-d/n-ATF5"), wherein the CP-d/n-ATF5 is capable of inhibiting ATF5 function and/or activity.

In certain embodiments, the neoplastic cell is selected from the group consisting of: breast, ovary, endometrium, gastric, colon, liver, pancreas, kidney, bladder, prostate, testis, skin (e.g., melanocyte/melanoma cell), esophagus, tongue, mouth, parotid, larynx, pharynx, lymph node, lung, blood (e.g., hematological cancers), peripheral nervous system, and brain. In certain embodiments, the neoplastic cell is selected from the group consisting of glioblastoma, astrocytoma, glioma, medulloblastoma, meningioma, mesothelioma, and neuroblastoma. In certain embodiments, the neoplastic cell is associated with a primary or a recurrent brain tumor.

In certain embodiments the CP-d/n-ATF5 is administered orally, parenterally (e.g., subcutaneously), intranasally, and/or transdermally.

In certain embodiments the CP-d/n-ATF5 comprises a portion of the human, rat, or mouse ATF5 peptide sequence or a combination thereof. In certain embodiments, the cell-penetrating dominant-negative ATF5 comprises a sequence selected from the group consisting of:

```
                                       (SEQ ID NO: 1)
LEQENAE, (SEQ ID NO: 2)
LEKEAEELEQENAE, (SEQ ID NO: 3)
LARENEELLEKEAEELEQENAE, (SEQ ID NO: 4)
LEQRAEELAREN EELLEKEAEELEQENAE,
or
                                       (SEQ ID NO: 4)
LEQRAEELARENEELLEKEAEELEQENAE,
``` linked to a peptide that forms a leucine zipper and to a cell-penetrating sequence. In certain embodiments, the CP-d/n-ATF5 comprises a sequence selected from the group consisting of:

```
                                       (SEQ ID NO: 5)
LEQENAELEGECQGLEARNRELKERAES, (SEQ ID NO: 6)
LEKEAEELEQENAELEGECQGLEARNRELK ERAES, (SEQ ID NO: 7)
LARENEELLEKEAEELEQENAELEGECQGLEARNRELKERAES, (SEQ ID NO: 8)
LEQRAEELAR NEELLEKEAEELEQENAELEGECQGLEARNRELKERA
ES, (SEQ ID NO: 9)
LEQRAEELARENEELLEKEAEELEQENAELEGECQGLEARNRELKERA
ESV,
``` where the underlined sequence is the dominant-negative sequence and the remainder of the sequence is the ATF5 leucine zipper, and the sequence is operably linked to (in frame) a cell-penetrating sequence. In certain embodiments, the cell-penetrating dominant-negative ATF5 comprises a sequence selected from the group consisting of:

```
                                       (SEQ ID NO: 10)
LEQENAELEGECQGLEARNRELRERAES, (SEQ ID NO: 11)
LEKEAEELEQENAEL EGECQGLEARNRELRERAES, (SEQ ID NO: 12)
LARENEELLEKEAEELEQENAELEGECQGLEARNREL RERAES, (SEQ ID NO: 13)
LEQRAEELARENEELLEKEAEELEQENAELEGECQGLEARNRELRERA
ES,
```

```
                                       (SEQ ID NO: 14)
LEQRAEELARENEELLEKEAEELEQENAELEGECQGLEARNRELRERA
ESV,
``` where the underlined sequence is the dominant-negative sequence and the remainder of the sequence is the ATF5 leucine zipper, and the sequence is operably lined to a cell-penetrating sequence.

In certain embodiments, the cell-penetrating dominant-negative ATF5 comprises a sequence selected from the group consisting of: (1)

```
                                       (SEQ ID NO: 15)
MGSSHHHHHHSSGLVPRGSHMRQIKIWFQNRRMKWKKDYKDDDDKMA

SMTGGQQMGRDPDLEQRAEELARENEELLEKEAEELEQENAE

LEGECQGLEARNRELRERAES V,
``` where the underlined residues (MG-HM) are a 6×His-tag leader sequence ("6×His" disclosed as SEQ ID NO: 16), the bold residues (RQ-KK) are a Penetratin sequence, the italicized residues (DY-DK) are a Flag tag, the residues with no font modification (MA-PD) are spacer amino acids, the bold and italicized residues (LE-AE) are a d/n sequence, and the bold and underlined residues (LE-SV) are an ATF5 leucine zipper truncated after its first Valine; (2)

```
                                       (SEQ ID NO: 17)
MGSSHHHHHHSSGLVPRGSHMLEYGRKKRRQRRRYPYDVPDYAMASMTG

GQQMGRDPDLEQRAEELARENEELLEKEAEELEQENAELEGECQGLEAR

NRELRERAESV,
``` where the underlined residues (MG-LE) are a 6×His-tag leader sequence ("6×His" disclosed as SEQ ID NO: 16), the bold residues (YG-RR) are a TAT sequence, the italicized residues (YP-YA) are an HA tag, the residues with no font modification (MA-PD) are spacer amino acids, the bold and italicized residues (LE-AE) are a d/n sequence, and the bold and underlined residues (LE-SV) are an ATF5 leucine zipper truncated after its first Valine; (3)

```
                                       (SEQ ID NO: 18)
MGSSHHHHHHSSGLVPRGSHMRQIKIWFQNRRMKWKKLEQRAEELARE

NEELLEKEAEELEQENAELEGECQGLEARNRELKERAESV
``` where the where the underlined residues (MG-HM) are a 6×His-tag leader sequence ("6×His" disclosed as SEQ ID NO: 16), the bold residues (RQ-KK) are a Penetratin sequence, the italicized residues (LE-AE) are a d/n sequence, and the bold and underlined residues (LE-SV) are an ATF5 leucine zipper truncated after its first Valine; and (4)

```
                                       (SEQ ID NO: 19)
RQIKIWFQNRRMKWKKLEQRAEELARENEELLEKEAEELEQENAELE

GECQGLEARNRELKERAESV
``` where the bold residues (RQ-KK) are a Penetratin sequence, the italicized residues (LE-AE) are a d/n sequence, and the bold and underlined residues (LE-SV) are an ATF5 leucine zipper truncated after its first Valine. In certain embodiments, the cell-penetrating dominant-negative ATF5 is chemically synthesized.

In certain embodiments, the invention also relates to kits for use in treating and/or preventing tumors and/or promoting apoptosis in a neoplastic cell. Additional aspects of the present invention will be apparent in view of the description which follows.

3. BRIEF DESCRIPTION OF THE FIGURES

FIG. 1 GFP-d/n-ATF5 C-terminally truncated fusion protein (GFP-d/n-ATF5-Tr) promotes the same level of apoptosis as full-length GFP-d/n-ATF5 protein in C6 glioma cells. C6 cells were transfected with pQC-X-I-eGFP, pQC-d/n-GFPATF5, or pQC-GFPATF5-tr. The percentages (mean±SEM, n=4; total of approximately 200 cells scored per condition) of condensed apoptotic nuclei in GFP+ transfected cells were determined 2 days later. Student's t-test; GFP+ cells versus GFP-d/n-ATF5+ cells or GFP-d/n-ATF5-tr cells, (*p<0.05); GFP-d/n-ATF5+ cells versus GFP-d/n-ATF5-tr cells, (Not Significant).

FIG. 2A-2C Purity and molecular properties of bacterially-expressed and purified 6×histidine-Flag-Tagged Penetratin-Flag-D/N-ATF5-tr (Pen-d/n-ATF5-RP) ("6×histidine" disclosed as SEQ ID NO: 16) and 6×histidine-Flag-Tagged Penetratin-Flag-Control (Pen-control-RP) peptides ("6×histidine" disclosed as SEQ ID NO: 16). (FIG. 2A) Coomassie stained SDS-PAGE of purified Pen-d/n-ATF5-RP and Pen-control-RP (5 μg per lane). Molecular weight markers are shown on the left, and a linear scheme of each peptide is shown above each lane. Purification was as described in Methods. (FIG. 2B) Deconvoluted mass spectra from LC-high Resolution mass spectrometry of purified Pen-d/n-ATF5-RP. The most abundant species is the 12,948.88 Da monomer form without formyl-methionine followed by the formyl-methionine 13,127 Da monomer form (isoform). The spectrum also reveals a small amount of the 25,897.5 Da dimer. (FIG. 2C) Stability of Pen-d/n-ATF5-RP in Human Serum. Pen-d/n-ATF5-RP (36 μM) was incubated with human serum (25% v/v in PBS) at 37° C. for 0 to 48 h. Aliquots were withdrawn at various times and the Pen-d/n-ATF5-RP peptide was resolved by SDS-PAGE, transferred to PVDF membrane and probed with anti-Flag antibody. The anti-Flag signal was detected by near IR using LiCor software and densitometry of the band at the expected size of Pen-d/n-ATF5-RP was performed and quantified using ImageJ. Values are mean±SEM, n=3.

FIG. 3A-3B Uptake and retention of Pen-d/n-ATF5-RP by cultured glioblastoma cells. (FIG. 3A) Confocal images of C6 rat glioblastoma cells incubated for 4 hours with either 200 nM Pen-control-RP (left) or Pen-d/n-ATF5-RP (right). Cells were washed, fixed and stained with anti-Flag (red) and DAPI (blue). Scale bar=2 μm. (FIG. 3B) Rat C6 and human U87 glioblastoma cells were incubated for the indicated times with 3 μM Pen-d/n-ATF5-RP, washed, fixed and immunostained with anti-Flag (green) and DAPI (blue). Scale bar=5 μm.

FIG. 4 Pen-d/n-ATF5-RP promotes apoptosis of C6 glioblastoma cells. C6 cells were treated with 3 μM Pen-d/n-ATF5-RP or 3 μM Pen-Control-RP, or were untreated. The percentage (mean±SEM; n=4 in 2 independent experiments; approximately 200 cells scored) of condensed apoptotic nuclei in cells was determined 5 days later. Student's t-test; Pen-d/n-ATF5-RP versus Pen-Control-RP cells or non-treated, (*p<0.05); Pen-Control-RP cells versus nontreated cells, (p=0.29).

FIG. 5A-5F Pen-d/n-ATF5-RP enters the mouse brain and causes targeted apoptosis of glioma cells. (FIG. 5A-5F) Representative brain sections stained with Flag antibody to indicate presence of Pen-d/n-ATF5-RP or HA to identify presence of tumor-inducing retrovirus (red); TUNEL to identify apoptosis (green) and DAPI to localize nuclei (blue). (FIG. 5A) Murine brain tumor 24 h post-treatment (16 h after last injection) with Pen-d/n-ATF5-RP (52 days post-retrovirus injection). (FIG. 5B) Normal contralateral cerebral hemisphere of the same mouse in FIG. 5A. (FIG. 5C) Murine brain tumor 24 h post-injection with saline (59 days post-retrovirus injection). Presence of Pen-d/n-ATF5 within cells is confirmed in the treated mouse (FIG. 5A, 5B) versus saline control (FIG. 5C) by increased Flag antibody staining. Glioma cell-specific induction of apoptosis by Pen-d/n-ATF5-RP is illustrated by increased TUNEL staining (green) in FIG. 5A as compared to FIG. 5B and FIG. 5C. (FIG. 5D) TUNEL and DAPI staining of a tumor-containing brain section 160 days post-retrovirus injection and 3 days after injection of Pen-control-RP. Note HA+ cells identifying tumor cells and absence of TUNEL staining. (FIG. 5E) Staining as in FIG. 5D of a tumor-containing section (143 days post-retrovirus injection) and 3 days after Pen-d/n-ATF5-RP treatment. Note the presence of TUNEL staining in HA+ tumor cells and fragmented appearance of the staining as compared to FIG. 5A and FIG. 5D. (FIG. 5F) Staining as in FIG. 5D of a tumor-containing section 150 days after retrovirus injection and 2 days after 2 treatments of subcutaneous Pen-d/n-ATF5-tr-RP injections. Note the qualitative similarity of staining pattern to FIG. 5E with fragmented PDGF-B-HA and TUNEL staining. Scale bars equal 20 μm.

FIG. 6A-6D Retention of Pen-d/n-ATF5-RP in mouse brain at various times after administration. Mice received 4 intraperitoneal injections of either saline (FIG. 6A) or Pen-d/n-ATF5-RP (FIG. 6B, 6C) as described in the text. Animals were sacrificed at either 40 (FIG. 6A, 6B) or 64 (FIG. 6C) h after the last injection and sections of their fixed brains were stained with either anti-Flag (Red; to visualize Pen-d/n-ATF5-RP) or DAPI (blue; to visualize nuclei). (FIG. 6D) Densitometry of anti-Flag Immunostaining. The optical densities (red channel) of fifteen random 0.176 inch2 areas were determined in each of the images and averaged±SD using Image J. Student's t-test; Pen-d/n-ATF5-RP (64 hours) or (40 hours) versus saline, (*p<0.05). Scale bar is 10 μm.

FIG. 7A-7D' H&E staining of the SVZ and hippocampal dentate gyrus shows no detectable difference between these structures in Pen-d/n-ATF5-RP-treated and non-treated mice. (FIG. 7A, 7A') Lateral ventricle/SVZ (FIG. 7A) and hippocampal dentate gyrus (FIG. 7A') from a tumor-bearing mouse 183 days after the second set of subcutaneous treatments with Pen-d/n-ATF5-RP. (FIG. 7B, 7B') Lateral ventricle/SVZ (FIG. 7B) and hippocampal dentate gyrus (FIG. 7B') from an age-matched control mouse not treated with Pen-d/n-ATF5-RP and not injected with retrovirus. (FIG. 7C, 7C') Lateral ventricle/SVZ (FIG. 7C) and hippocampal dentate gyrus (FIG. 7C') from a non-tumor-bearing mouse 1 day after the second set (given 5 days after the first set) of subcutaneous treatments with Pen-d/n-ATF5-RP. (FIG. 7D, 7D') Lateral ventricle/SVZ (FIG. 7D) and hippocampal dentate gyrus (FIG. 7D') from an age-matched untreated non-tumor-bearing control mouse. Scale for FIG. 7A-7B' is 20 μm and 50 μm for FIG. 7C-7D'.

FIG. 8A-8F Example of MRI and histopathology of a mouse glioma treated with Pen-Control-RP peptide. (FIG. 8A) Post-contrast 3D FLASH MRI coronal image of the cerebrum of a control mouse that was not injected with PDGF-B-HA/sh-p53 retrovirus. (FIG. 8B) Post-contrast 3D FLASH MRI coronal image of mouse cerebrum showing a bilateral tumor (white contrast) 246 days after PDGF-B-HA/ shp53 retrovirus injection and prior to treatment with Pen-Control-RP peptide. (FIG. 8C) Post-contrast 3D FLASH MRI image of the same mouse brain 40 days after subcutaneous treatment with Pen-Control-RP peptide (as described in the text) reveals persistence of the tumor (arrows). (FIG. 8D) H&E stained sections of the same mouse brain at tumor-containing areas 1 and 2 shown by arrows in panel FIG. 8C. The mouse was sacrificed 116 days after the second treatment with Pen-Control-RP peptide due to moribund behavior. Presence of tumor is indicated in both sections by hyperchromatic nuclei and higher cellularity. (FIG. 8E) Immunostaining for HA tag in sections from areas 1 and 2 shown in FIG. 8C reveals presence of virally-delivered PDGF-B-HA in induced tumor cells. (FIG. 8F) Immunostaining of sections from areas 1 and 2 shown in FIG. 8C reveals a high index of Ki67+/dividing cells indicative of tumor. Scale bars in FIG. 8D-8F are 20 μm.

FIG. 9A-9E Pen-d/n-ATF5-RP promotes rapid and long-term regression/eradication of mouse glioma as indicated by MRI and histology. (FIG. 9A) Post-contrast 3D FLASH MRI scans of a mouse brain before and at various times after treatment (as described in text) with Pen-d/n-ATF5-RP. Pretreatment shows image of cortex 243 days after PDGF-B-HA/shp53 retrovirus injection. Yellow arrows indicate location of the bilateral tumor. Post-treatment images of the same position of the mouse cortex are at the indicated times after the second administration of Pen-d/n-ATF5-RP. Yellow arrows in post-treatment images show location of original tumor. (FIG. 9B) H&E image of the same mouse brain harvested 192 days after the second Pen-d/n-ATF5-RP treatment. Region 1 represents the location of the section as shown in the final time point in FIG. 9A and at which the tumor was present before treatment. Note the absence of hyperchromatic nuclei and higher cellularity that characterize gliomas. (FIG. 9C) Ki67 staining in region 2 (from Panel A/176 days post-treatment). Note the absence of Ki67+/proliferating cells seen in gliomas. (FIG. 9D) HA/DAPI staining of section from region 1. Note the absence of cells expressing exogenous PDGF-B-HA. (FIG. 9E) GFAP/DAPI staining of section region 1. Note clusters of GFAP+ cells consistent with the presence of a glial scar where the tumor was formerly present. Lack of HA staining of a nearby section confirmed the absence of tumor cells. Diagonal green stripes are due to tissue folds. Scale bar is 20 μm.

FIG. 10 MRI and histopathological images of an untreated mouse with a bilateral tumor. Middle panel shows post-contrast 3D FLASH MRI image of a tumor-bearing mouse brain at 112 days after PDGF-B-HA/shp53 retrovirus injection. Panels (A) and (B) show images for sections stained with HA to reveal tumor cells and with DAPI to show nuclei. The yellow arrows on the MRI along with the letters show the relative locations of the HA+ sections shown in (A) and (B). Retroviral injection was on side B. Scale bar is 20 μm. DAPI (40,6-diamidino-2-phenylindole).

FIG. 11A-11E Second example illustrating that Pen-d/n-ATF5-RP promotes rapid and long-term regression/eradication of a mouse glioma as indicated by MRI and histology. (FIG. 11A) Post-contrast 3D FLASH MRI images of a tumor-bearing mouse brain before and at various times after treatment with Pen-d/n-ATF5-RP. Pretreatment coronal and transverse images (74 days after PDGF-B-HA/shp53 retrovirus injection) show multifocal tumors within the cortex (arrows). Images from the same mouse brain are shown at 8, 21 and 181 days after two sets of subcutaneous treatments with Pen-d/n-ATF5-RP as described in the text. Note decreased signal at 8 days and absence of detectable signals at 21 and 181 days following treatment. (FIG. 11A', 11A") Estimates of tumor volume corroborate loss of signal by 8 days after Pen-d/n-ATF5-RP treatment. The same images as in FIG. 11A for pretreatment and 8 days post-treatment with arrows pointing to tumor foci (yellow circles) for which volumetric measurements were obtained using the region of interest elliptic cylinder tool (yellow circles). At pretreatment, the calculated volumes in FIG. 11A' are 0.597 mm3, 0.164 mm3, and 0.760 mm3 for foci 1, 2, and 3, respectively. For 8 days post-treatment (FIG. 11A"), volumes of the same tumors decreased to 0.106 mm3, 0.0302 mm3, and 0.0895 mm3 for foci 1, 2, and 3, respectively. After 21 days of treatment the tumors could not be visualized for measurement. (FIG. 11B) H&E staining of the same sacrificed mouse brain (183 days after treatment; 190 days after initial tumor detection) corroborates the absence of detectable tumor with the arrow pointing to the remnant scar corresponding to tumor focus 1 shown in FIG. 11A' and corroborates absence of detectable tumor. (FIG. 11C) HA immunostaining of the same brain (for PDGF-B-HA) indicates the absence of detectable tumor cells in the same focus 1 region as in FIG. 11A' and FIG. 11B. (FIG. 11D) GFAP immunostaining of the same brain at focus 1 shows a remnant GFAP+ glial scar. (FIG. 11E) Ki67 immunostaining of the focus 1 region of the same brain reveals the absence of dividing cells. Scale bar is 20 μm for FIG. 11B-11E.

FIG. 12A-12C Long-term survival and tumor presence outcomes for glioma-bearing mice treated with Pen-d/n-ATF5-RP. (FIG. 12A) Survival of glioma-bearing mice (verified by MRI) with or without treatment with Pen-d/n-ATF5-RP (subcutaneous delivery as described in the text). Of the nine control mice, four control mice were treated with Pen-Control-RP peptide and five were untreated. The experimental endpoint was 200 days after initial tumor detection by MM. Survival analysis achieved by log-rank test showed a p-value=0.0007 (http://in-silico.net/tools/statistics/survivor). (FIG. 12B) MRI outcomes for tumor-bearing mice before and after subcutaneous treatment with Pen-d/n-ATF5-RP as described in the text. The latter times range from 176-225 days after tumor treatment (183-230 days after tumor detection). (FIG. 12C) Brain histopathological outcomes for tumors in control and Pen-d/n-ATF5-RP treated mice. In all cases, MRI verified the presence of tumors prior to treatment. Control animals were as described in FIG. 12A and brains were harvested either after death (6 controls), after the 6 month experimental endpoint (4 treated animals) or after sacrifice for non-tumor related health problems (2 treated animals). For treated animals, histological analysis was carried out 260-438 days after tumor initiation (183-259 days after Pen-d/n-ATF5-RP administration and 190-305 days after initial tumor detection). Sections of brain were prepared as described in Methods and were stained with H&E and immunostained for Ki67 and HA (to identify PDGF-B-HA+ tumor cells). The presence/absence of tumors was based on observations of hyperchromatic nuclei, high cellularity, elevated Ki67 staining and HA immunostaining.

FIG. 13 indicates that TAT-d/n-ATF5 (TAT-ZIP) promotes apoptotic death of cultured melanoma MEL501 cells. TAT-linked dominant-negative ATF5 peptide at the indicated concentrations (in μM) was added to medium of MEL501 melanoma cells. Four days later the cells were stained with Hoescht dye and the cells were stained for proportion with apoptotic nuclei.

FIG. 14 indicates that TAT-d/n-ATF5 (TAT-ZIP) reduces the expression of endogenous ATF5 in cultured U373 glioblastoma cells. TAT-linked dominant-negative ATF5 peptide at the indicated concentrations (in μM) was added to medium of U373 glioblastoma cells for 17 hrs day and the cells were then harvested and analyzed by Western immunoblotting for levels of endogenous ATF5. Note that the TAT-d/n-ATF5 greatly reduces expression of endogenous ATF5. As previous studies have shown that tumor cells require endogenous ATF5 to survive, the mechanism of action by which the cell-penetrating TAT-ZIP peptide kills may be by causing loss of the endogenous ATF5 protein. Note also the smear above the endogenous ATF5 when the TAT-ZIP peptide is present. This suggests that TAT-ZIP reduces endogenous ATF5 by causing its ubiquitination and proteasomal degradation.

FIG. 15 indicates that TAT-d/n-ATF5 (TAT-ZIP) peptide induces expression of the pro-death gene DDIT3 (CHOP) in various tumor cell lines. Cells were treated with TAT-d/n-ATF5 for the indicated times at the indicated doses (in μM) and then harvested and analyzed by Western immunoblotting for expression of CHOP and other non-responsive proteins. Note the elevation of CHOP in all cases. Since CHOP may promote cell death, these data indicate that induction of CHOP protein may be one mechanism by which TAT-d/n-ATF5 kills tumor cells.

FIG. 16 indicates that silencing of CHOP protein with siRNA (top Western immunoblot) partially protects U87 cells from death caused by TAT-d/n-ATF5 peptide. Cells were treated with siCHOP to silence CHOP expression (top Western immunoblot) or with control siRNA. They were then exposed to TAT-d/n-ATF5 for 2 days and assessed for proportion of cells with apoptotic nuclei. The data support the idea that part of the mechanism by which TAT-d/n-ATF5 kills tumor cells is by increasing their expression of CHOP which in turn mediates death.

FIG. 17 indicates that TAT-D/N-ATF5 down-regulates BCL2 survival protein. Cultured U87 human glioblastoma cells were treated with the indicated concentrations of TATZIP (TAT-d/n-ATF5 peptide) (in μM) for 30 hrs. The cells were then harvested and assessed by Western immunoblotting for expression of the survival protein BCL2. These findings indicate that in addition to elevating pro-death CHOP, TAT-d/n-ATF5 may also kill tumor cells by reducing their levels of the BCL2 survival protein.

FIG. 18 indicates that TAT-D/N-ATF5 synergizes with temozolomide (TMZ) to kill cultured U87 glioblastoma cells. Cells were cultured for one day with sub-lethal levels of TAT-d/n-ATF5 (TZIP 1 μM) and TMZ (50 μM) either separately or in combination, and then assessed for proportion of cells with apoptotic nuclei. TMZ is presently the first-line treatment for human GBM. The data reveal that TAT-d/n-ATF5 not only functions in presence of TMZ, but that the two drugs act in synergy to kill GBM cells. This suggests that TAT-d/n-ATF5 can be administered to patients who are taking TMZ.

Figure 21:
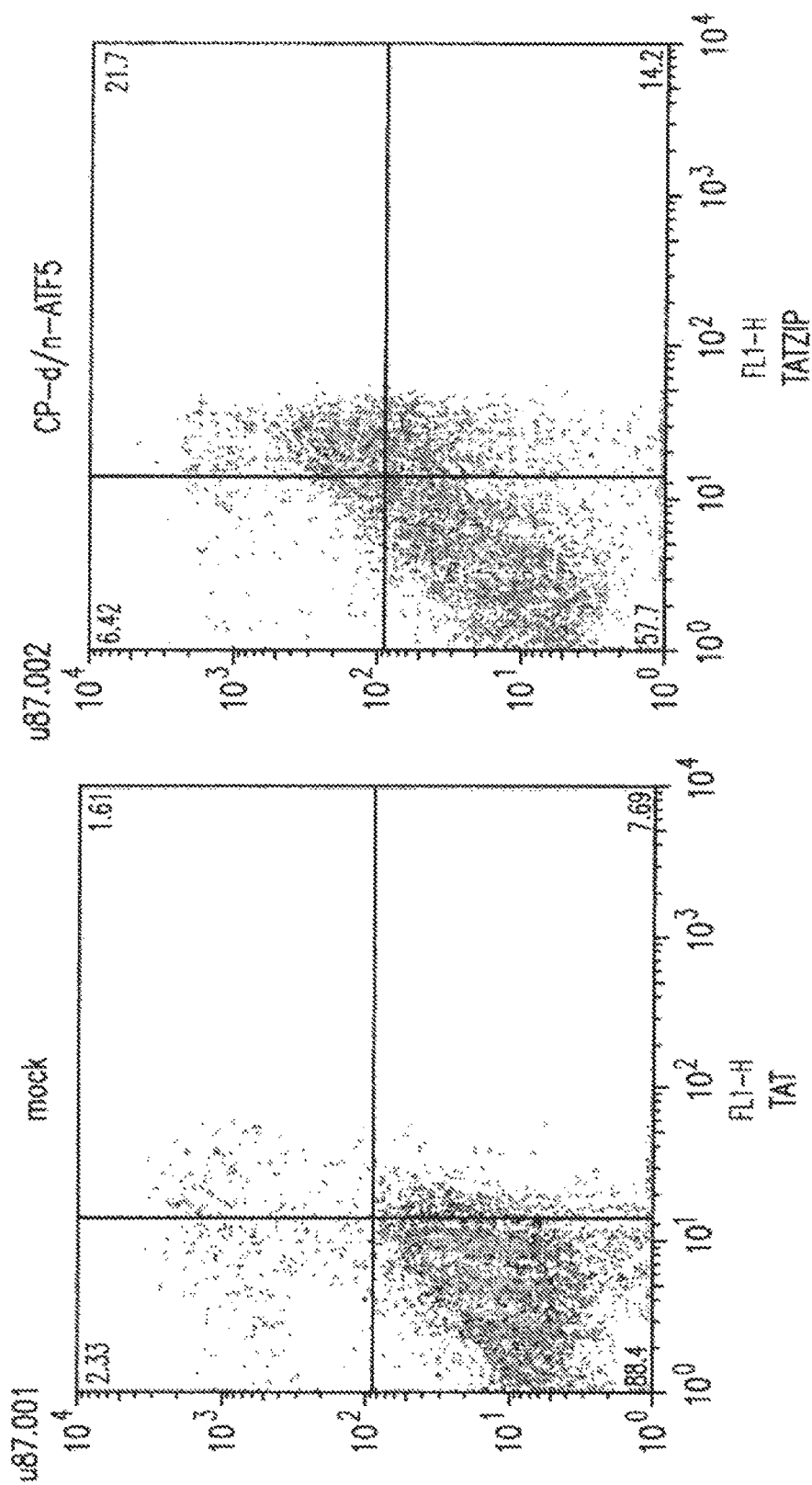

FIG. 21 depicts recombinant TAT-d/n-ATF5 treatment promoting death of cultured U87 human glioblastoma cells as indicated by Annexin V/PI staining and flow cytometry. Proportions of viable cells are shown in lower left quadrant (88% control vs 58% treated). Dying cell proportions are in the lower right and upper right quadrants (9% in controls vs 36% in treated).

Figure 22:
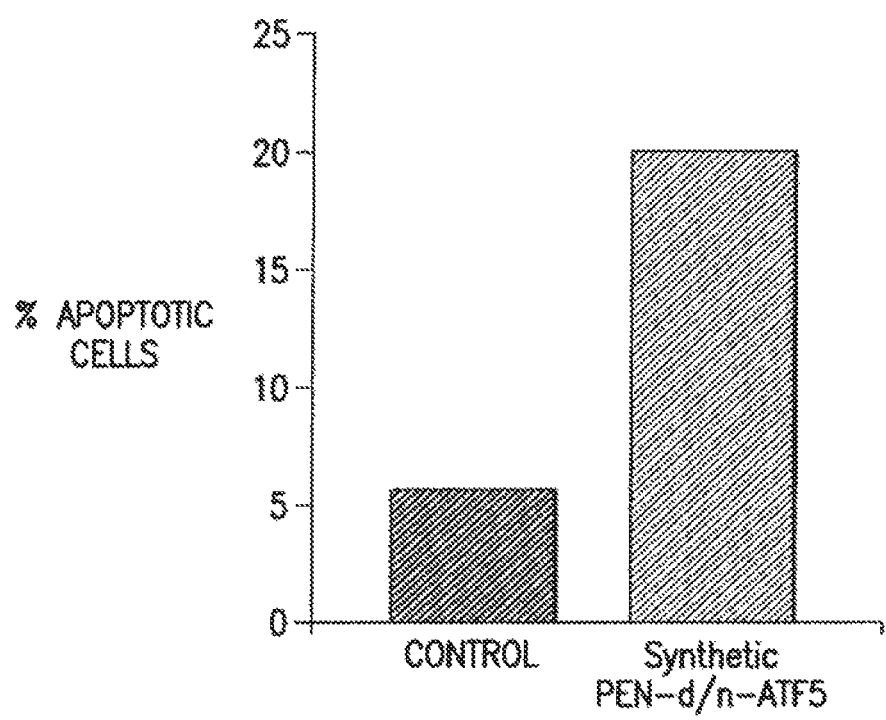
Figure 23:
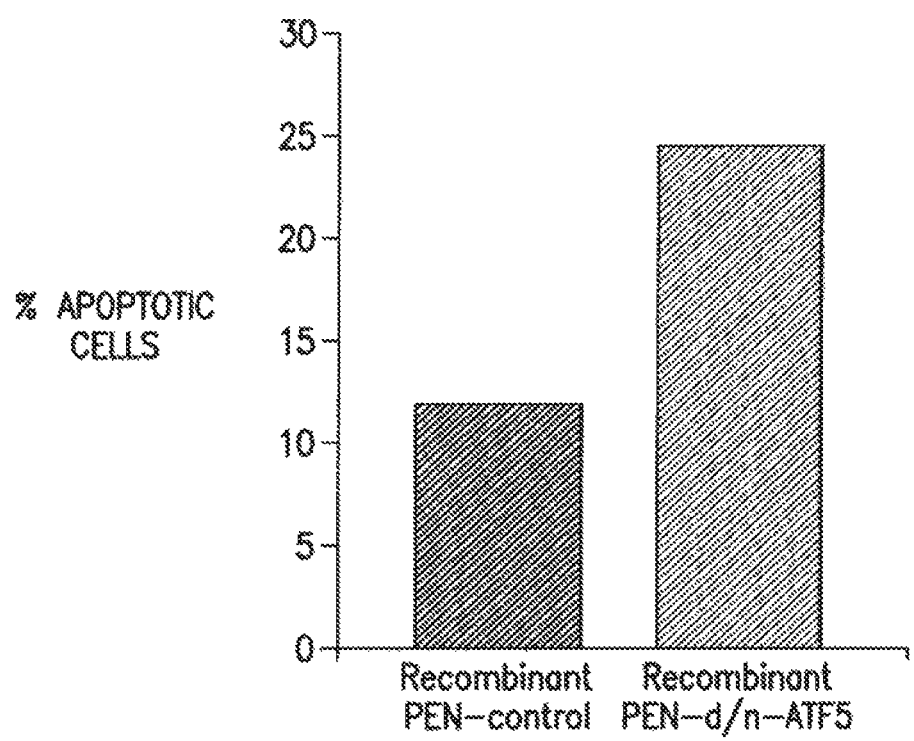

FIG. 22 depicts synthetic PEN-d/n-ATF5 promoting apoptotic death of primary GS9-6 human glioblastoma stem cells growing in culture as spheres. 6 days of treatment and data determined by Annexin V/PI staining and flow cytometry FIG. 23 depicts recombinant PEN-d/n-ATF5 promoting apoptotic death of primary GS9-6 human glioblastoma stem cells growing in culture as spheres. 5 days of treatment and data determined by Annexin V/PI staining and flow cytometry.

4. DETAILED DESCRIPTION OF THE INVENTION

4.1 ATF5 & D/N-ATF5 Compositions

ATF5 is widely expressed by various tumor types. In particular, ATF5 is expressed not only in highly proliferative neural tumors, e.g., glioblastomas, but is also expressed in multiple neoplasias including, but not necessarily limited to: breast, ovary, endometrium, gastric, colon, liver, pancreas, kidney, bladder, prostate, testis, skin, esophagus, tongue, mouth, parotid, larynx, pharynx, lymph node, lung, hematological cancers, peripheral nervous system, and brain tumors.

As used herein, "ATF5" includes both an "ATF5 protein" and an "ATF5 analogue". Unless otherwise indicated, "protein" shall include a protein, protein domain, polypeptide, or peptide, and any fragment thereof. The ATF5 protein has the amino acid sequence set forth in NCBI Accession No. NP_001180575 (human ATF5) or NCBI Accession No. NP_109618 (murine ATF5), including conservative substitutions thereof. As used herein, "conservative substitutions" are those amino acid substitutions which are functionally equivalent to a substituted amino acid residue, either because they have similar polarity or steric arrangement, or because they belong to the same class as the substituted residue (e.g., hydrophobic, acidic, or basic). As described below, Western immunoblotting has permitted the identification of the major cellular form of ATF5 protein. The ATF5 cDNA sequence predicts two potential in-frame methionine start sites that would lead to proteins of approximately 30 and 20 kDa. Observation that the major form of ATF5 in cells has an apparent molecular mass of 20-22 kDa indicates favored utilization of the second site. When a canonical Kozak initiation consensus sequence was included upstream of the first methionine, the larger protein was expressed, thereby indicating that the 22-kDa form is not formed by cleavage of a 30-kDa precursor. Accordingly, the ATF5 protein of the present invention further includes both the 22-kDa and 30-kDa isomers thereof.

An "ATF5 analogue", as used herein, is a functional variant of the ATF5 protein, having ATF5 biological activity, that has 60% or greater (in certain embodiments, 70% or greater or 80% or greater or 90% or greater or 95% or greater) amino-acid-sequence homology with the ATF5 protein. As further used herein, the term "ATF5 biological activity" refers to the activity of an ATF5 protein or ATF5 analogue to associate physically with, or bind with, CRE (i.e., binding of approximately two fold, or, more preferably, approximately five fold, above the background binding of a negative control), under the conditions of the assays described herein, although affinity may be different from that of native ATF5.

The skilled practitioner understands that the numbering of amino acid residues in ATF5 may be different than that set forth herein, or may contain certain conservative amino acid substitutions that produce the same ATF5-CRE associating activity as that described herein. Corresponding amino acids and conservative substitutions in other isoforms or analogues are easily identified by visually inspecting the relevant amino acid sequences, or by using commercially available homology software programs.

As outlined in the Examples section, interference with the function and/or activity of ATF5 promote apoptosis of glioblastoma multiforme tumors (GBM) in vitro and in vivo. Furthermore, selective interference with ATF5 function and/or activity in other carcinoma types is shown to triggers cell death. Culture and animal studies also show that the transcription factor ATF5 is required for survival of GBM cells and that limited subcutaneous treatment with a CP-d/n-ATF5 causes apparent tumor eradication in a mouse model of endogenous gliomas without apparent toxicity or side effects. As highlighted in the attached examples, the effect of such ATF5 interference by administration of a CP-d/n-ATF5 is indeed specific, in that interfering with ATF5 function and/or activity triggers increased cell death in neoplastic cells, but not normal cells.

As used herein, "dominant-negative ATF5" or "d/n-ATF5" is a peptide comprising a portion of the human ATF5 amino acid sequence. In certain embodiments, the d/n-ATF5 peptide comprises the sequence LEQENAELEGECQGLEARNRELKERAES (SEQ ID NO: 5), where the underlined sequence is the dominant-negative sequence and the remainder of the sequence is the ATF5 leucine zipper. In certain embodiments the d/n-ATF5 is encoded by a nucleic acid comprising the sequence CTG-GAACAGGAAAACGCGGAACTGGAAGGCGAATGC-CAGGGCCTGG AAGCGCGCAACCGCGAACT-GAAAGAACGCGCGGAAAGCTAA (SEQ ID NO: 20). In certain embodiments the d/n-ATF5 peptide comprises (SEQ ID NO: 6)
LEKEAEELEQENAELEGECQGLEARNRELKERAES.

In certain embodiments the d/n-ATF5 is encoded by a nucleic acid comprising the sequence CTG-GAAAAAGAAGCGGAAGAACTGGAACAG-GAAAACGCGGAACTGGAAGG CGAATGCCAGGGC-CTGGAAGCGCGCAACCGCGAACTGAAAGAACGCG CGGA AAGCTAA (SEQ ID NO: 21). In certain embodiments, the d/n-ATF5 peptide comprises the sequence (SEQ ID NO: 7)
LARENEELLEKEA EELEQENAELEGECQGLEARNRELKERAES, where the underlined sequence is the dominant-negative sequence and the remainder of the sequence is the ATF5 leucine zipper. In certain embodiments the d/n-ATF5 is encoded by a nucleic acid comprising the sequence CTG-GCGCGCGAAAACGAAGAACTGCTG-GAAAAAGAAGCGGAAGAACTGGAA CAG-GAAAACGCGGAACTGGAAGGCGAATGCCAGGGCC TGGAAGCGCGCAAC CGCGAACT-GAAAGAACGCGCGGAAAGCTAA (SEQ ID NO: 22). In certain embodiments, the d/n-ATF5 peptide comprises the sequence (SEQ ID NO: 23)
LEQRAEELARENEELLEKEAEELEQENAELEGECQGLEARN RELKE
RAES, where the underlined sequence is the dominant-negative sequence and the remainder of the sequence is the ATF5 leucine zipper. In certain embodiments the d/n-ATF5 is encoded by a nucleic acid comprising the sequence CTG-GAACAGCGCGCGGA AGAACTGGCGCGCGAAAAC-GAAGAACTGCTGGAAAAAGAAGCGGAAGAACT GGAACAGGAAAACGCGGAACTGGAAGGCGAAT-GCCAGGGCCTGGAAGCGCG CAACCGCGAACT-GAAAGAACGCGCGGAAAGCTAA (SEQ ID NO: 24). In certain embodiments, the d/n-ATF5 peptide comprises the sequence (SEQ ID NO: 9)
LEQRAEELARENEELLEKEAEELEQENAELEGECQGLEARNREL KE
RAESV, where the underlined sequence is the dominant-negative sequence and the remainder of the sequence is the ATF5 leucine zipper. In certain embodiments the d/n-ATF5 is encoded by a nucleic acid comprising the sequence CTG-GAACAGCGCGCGGAAGAACTGGCGCG CGAAAAC-GAAGAACTGCTGGAAAAAGAAGCGGAAGAACTG-GAACAGGAAA ACGCGGAACTGGAAGGCGAATGCCAGGGCCTG-GAAGCGCGCAACCGCGAAC TGAAAGAACGCGCG GAAAGCGTGTAA (SEQ ID NO: 25). In certain embodiments, a d/n-ATF5 comprising the ATF5 leucin zipper sequence LEGECQGLEARNRELKERAESV (SEQ ID NO: 26), will further comprise, 1, 2, 3, 4, 5, 6, 7, 8, 9, 10, 11, 12, 13, 14, 15, 16, 17, 18, 19, 20, 21, 22, 23, or 24 additional C-terminal ATF5 leucine zipper residues. In certain embodiments, the d/n-ATF5 peptide consists of one of the foregoing peptide sequences.

As used herein, "dominant-negative ATF5" or "d/n-ATF5" is a peptide comprising a portion of the rat or mouse ATF5 amino acid sequence. In certain embodiments, the d/n-ATF5 peptide comprises the sequence LEQENAELEGECQGLEARNRELRERAES (SEQ ID NO: 10), where the underlined sequence is the dominant-negative sequence and the remainder of the sequence is the ATF5 leucine zipper. In certain embodiments the d/n-ATF5 is encoded by a nucleic acid comprising the sequence CTG-GAACAGGAAAACGCGGAACTGGAAGGCGAATGC-CAGGG CCTGGAAGCGCGCAACCGCGAACTGCGC-GAACGCGCGGAAAGCTAA (SEQ ID NO: 27). In certain embodiments, the d/n-ATF5 peptide comprises the sequence (SEQ ID NO: 11)
LEKEAEELEQENAELEGECQ GLEARNRELRERAES, where the underlined sequence is the dominant-negative sequence and the remainder of the sequence is the ATF5 leucine zipper. In certain embodiments the d/n-ATF5 is encoded by a nucleic acid comprising the sequence CTG-GAAAAAGAAGCG GAAGAACTGGAACAG-GAAAACGCGGAACTGGAAGGCGAATGCCAGGGC-CTG GAAGCGCGCAACCGCGAACTGCGCGAACGCGCG-GAAAGCTAA (SEQ ID NO: 28). In certain embodiments, the d/n-ATF5 peptide comprises the sequence (SEQ ID NO: 12)
LARENEELLEKEAEELEQENAELEGECQGL EARNRELRERAES, where the underlined sequence is the dominant-negative sequence and the remainder of the sequence is the ATF5 leucine zipper. In certain embodiments the d/n-ATF5 is encoded by a nucleic acid comprising the sequence CTG- GCGCGCGAAAACGAAGAAC TGCTGGAAAAAGAAGCGGAAGAACTGGAACAGGAAAACGCGGAACTGGAAG GCGAATGCCAGGGCCTGGAAGCGCGCAACCGCGAACTGCGCGAACGCGCGG AAAGCTAA (SEQ ID NO: 29). In certain embodiments, the d/n-ATF5 peptide comprises the sequence (SEQ ID NO: 13)
LEQRAEELARENEELLEKEAEELEQENAELEGECQGLEARNRELRERAES, where the underlined sequence is the dominant-negative sequence and the remainder of the sequence is the ATF5 leucine zipper. In certain embodiments the d/n-ATF5 is encoded by a nucleic acid comprising the sequence CTGGAACAGCGCGCGGAAGAACTGGCGCGCGAAAACGAA GAACTGCTGGAAAAAGAAGCGGAAGAACTGGAACAGGAAAACGCGGAACTG GAAGGCGAATGCCAGGGCCTGGAAGCGCGCAACCGCGAACTGCGCGAACGC GCGGAAAGCTAA (SEQ ID NO: 30). In certain embodiments, the d/n-ATF5 peptide comprises the sequence (SEQ ID NO: 14)
LEQRAEELARENEELLEKEAEELEQENAELEGECQGLEARNRELRERAESV, where the underlined sequence is the dominant-negative sequence and the remainder of the sequence is the ATF5 leucine zipper. In certain embodiments the d/n-ATF5 is encoded by a nucleic acid comprising the sequence CTGGAACAGCGCGCGGAAGAACTGGCGCGCGAAAACGAAGA ACTGCTGGAAAAAGAAGCGGAAGAACTGGAACAGGAAAACGCGGAACTGGA AGGCGAATGCCAGGGCCTGGAAGCGCGCAACCGCGAACTGCGCGAACGCGC GGAAAGCGTGTAA (SEQ ID NO: 31). In certain embodiments, a d/n-ATF5 comprising the ATF5 leucin zipper sequence LEGECQGLEARNRELRERAESV (SEQ ID NO: 32), will further comprise, 1, 2, 3, 4, 5, 6, 7, 8, 9, 10, 11, 12, 13, 14, 15, 16, 17, 18, 19, 20, 21, 22, 23, or 24 additional C-terminal ATF5 leucine zipper residues of the sequence EREIQYVKDLLIEVYKARSQRTRS (SEQ ID NO: 33). In certain embodiments, the d/n-ATF5 peptide consists of one of the foregoing peptide sequences.

As used herein, a "cell-penetrating peptide" or "CP" is a peptide that comprises a short amino acid sequence (e.g., in certain embodiments, about 12-30 residues) or functional motif that confers the energy-independent (i.e., non-endocytotic) translocation properties associated with transport of the membrane-permeable complex across the plasma and/or nuclear membranes of a cell. Representative amino acid motifs conferring such properties are listed in U.S. Pat. No. 6,348,185, the contents of which are expressly incorporated herein by reference. The cell-penetrating peptides of the present invention preferably include, but are not limited to, penetratin1, transportan, pIs1, TAT(48-60), pVEC, MTS, and MAP.

The cell-penetrating peptides of the present invention include those sequences that retain certain structural and functional features of the identified cell-penetrating peptides, yet differ from the identified peptides' amino acid sequences at one or more positions. Such polypeptide variants can be prepared by substituting, deleting, or adding amino acid residues from the original sequences via methods known in the art.

In certain embodiments, such substantially similar sequences include sequences that incorporate conservative amino acid substitutions, as described above in connection with polypeptide apoptotic target inhibitors. In certain embodiments, a cell-penetrating peptide of the present invention is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homologous to the amino acid sequence of the identified peptide and is capable of mediating cell penetration. The effect of the amino acid substitutions on the ability of the synthesized peptide to mediate cell penetration can be tested using the methods disclosed in Examples section, below.

In certain embodiments of the present invention, the cell-penetrating peptide is penetratin1, comprising the peptide sequence RQIKIWFQNRRMKWKK (SEQ ID NO: 34), or a conservative variant thereof. As used herein, a "conservative variant" is a peptide having one or more amino acid substitutions, wherein the substitutions do not adversely affect the shape—or, therefore, the biological activity (i.e., transport activity) or membrane toxicity—of the cell-penetrating peptide.

Penetratin1 is a 16-amino-acid polypeptide derived from the third alpha-helix of the homeodomain of *Drosophila antennapedia*. Its structure and function have been well studied and characterized: Derossi et al., Trends Cell Biol., 8(2):84-87, 1998; Dunican et al., Biopolymers, 60(1):45-60, 2001; Hallbrink et al., Biochim. Biophys. Acta, 1515(2): 101-09, 2001; Bolton et al., Eur. J. Neurosci., 12(8):2847-55, 2000; Kilk et al., Bioconjug. Chem., 12(6):911-16, 2001; Bellet-Amalric et al., Biochim. Biophys. Acta, 1467(1):131-43, 2000; Fischer et al., J. Pept. Res., 55(2): 163-72, 2000; Thoren et al., FEBS Lett., 482(3):265-68, 2000.

It has been shown that penetratin1 efficiently carries avidin, a 63-kDa protein, into human Bowes melanoma cells (Kilk et al., Bioconjug. Chem., 12(6):911-16, 2001). Additionally, it has been shown that the transportation of penetratin1 and its cargo is non-endocytotic and energy-independent, and does not depend upon receptor molecules or transporter molecules. Furthermore, it is known that penetratin1 is able to cross a pure lipid bilayer (Thoren et al., FEBS Lett., 482(3):265-68, 2000). This feature enables penetratin1 to transport its cargo, free from the limitation of cell-surface-receptor/-transporter availability. The delivery vector previously has been shown to enter all cell types (Derossi et al., Trends Cell Biol., 8(2):84-87, 1998), and effectively to deliver peptides (Troy et al., Proc. Natl. Acad. Sci. USA, 93:5635-40, 1996) or antisense oligonucleotides (Troy et al., J. Neurosci., 16:253-61, 1996; Troy et al., J. Neurosci., 17:1911-18, 1997).

In certain embodiments, the CP-d/n-ATF5 is a peptide comprising a Penetratin sequence operably linked to a rat d/n-ATF5 sequence. In certain embodiments the CP-d/n-ATF5 peptide sequence is (SEQ ID NO: 15)
MGSSHHHHHHSSGLVPRGSHMRQIKIWFQNRRMKWKK*DYKDDDD*

*KMA*SMTGGQQMGRDPD<u>LEQRAEELARENEELLEKEAEELEQENAE</u>

<u>LEGECQGLEARNRELRERAESV</u>, where the underlined residues are a 6×His-tag leader sequence ("6×His" disclosed as SEQ ID NO: 16), the bold residues are a Penetratin sequence, the italicized residues are a Flag tag, the residues with no font modification are spacer amino acids, the bold and italicized residues are a d/n sequence, and the bold and underlined residues are an ATF5 leucine zipper truncated after its first Valine. In certain embodiments the CP-d/n-ATF5 is encoded by a nucleic acid comprising the sequence (SEQ ID NO: 35)
ATGGGCAGCAGCCATCATCATCATCATCACAGCAGCGGCCTGGTGCC

GCGCGGCAGCCATATGCGTCAAATTAAAATTTGGTTTCAAAATCGTC

GTATGAAATGGAAAAAAGACTACAAGGACGATGATGACAAAATGGCA

TCTATGACTGGAGGACAACAAATGGGAAGAGACCCAGACCTCGAACA

AAGAGCAGAAGAACTAGCAAGAGAAAACGAAGAACTACTAGAAAAAG

AAGCAGAAGAACTAGAACAAGAAAATGCAGAGCTAGAGGGCGAGTGC

CAAGGGCTAGAGGCGCGGAATCGGGAGCTGAGGGAGAGGGCAGAGTC

AGTGTAG.

Other non-limiting embodiments of the present invention involve the use of the following exemplary cell permeant molecules: RL16 (H-RRLRRLLRRLLRRLLRRLRR-OH (SEQ ID NO: 36)), a sequence derived from Penetratin1 with slightly different physical properties (Biochim Biophys Acta. 2008 July-August; 1780(7-8):948-59); and RVGR-RRRRRRRR (SEQ ID NO: 37), a rabies virus sequence which targets neurons see P. Kumar, H. Wu, J. L. McBride, K. E. Jung, M. H. Kim, B. L. Davidson, S. K. Lee, P. Shankar and N. Manjunath, Transvascular delivery of small interfering RNA to the central nervous system, *Nature* 448 (2007), pp. 39-43.

In certain alternative non-limiting embodiments of the present invention, the cell-penetrating peptide is a cell-penetrating peptides selected from the group consisting of: transportan, pIS1, Tat(48-60), pVEC, MAP, and MTS. Transportan is a 27-amino-acid long peptide containing 12 functional amino acids from the amino terminus of the neuropeptide galanin, and the 14-residue sequence of mastoparan in the carboxyl terminus, connected by a lysine (Pooga et al., FASEB J., 12(1):67-77, 1998). It comprises the amino acid sequence GWTLNSAGYLLGKINLKA-LAALAKKIL (SEQ ID NO: 38), or a conservative variant thereof.

pIs1 is derived from the third helix of the homeodomain of the rat insulin 1 gene enhancer protein (Magzoub et al., Biochim. Biophys. Acta, 1512(1):77-89, 2001; Kilk et al., Bioconjug. Chem., 12(6):911-16, 2001). pIs1 comprises the amino acid sequence PVIRVW FQNKRCKDKK (SEQ ID NO: 39), or a conservative variant thereof.

Tat is a transcription activating factor, of 86-102 amino acids, that allows translocation across the plasma membrane of an HIV-infected cell, to transactivate the viral genome (Hallbrink et al., Biochem. Biophys. Acta., 1515(2):101-09, 2001; Suzuki et al., J. Biol. Chem., 277(4):2437-43, 2002; Futaki et al., J. Biol. Chem., 276(8):5836-40, 2001). A small Tat fragment, extending from residues 48-60, has been determined to be responsible for nuclear import (Vives et al., J. Biol. Chem., 272(25):16010-017, 1997); it comprises the amino acid sequence: YGRKKRRQRRR (SEQ ID NO: 40); GRKKRRQRRRPPQ (SEQ ID NO: 41); or a conservative variant thereof.

In certain embodiments, the CP-d/n-ATF5 is a peptide comprising a TAT sequence operably linked to a rat d/n-ATF5 sequence. In certain embodiments the CP-d/n-ATF5 peptide sequence is (SEQ ID NO: 17)
MGSSHHHHHHSSGLVPRGSHMLEYGRKKRRQRRRYPYDVPDYAMA

SMTGGQQMGRDPD***LEQRAEELARENEELLEK EAEELEQENAE*L**

EGECQGLEARNRELRERAESV, where the underlined residues are a 6×His-tag leader sequence ("6×His" disclosed as SEQ ID NO: 16), the bold residues are a TAT sequence, the italicized residues are an HA tag, the residues with no font modification are spacer amino acids, the bold and italicized residues are a d/n sequence, and the bold and underlined residues are an ATF5 leucine zipper truncated after its first Valine. In certain embodiments the CP-d/n-ATF5 is encoded by a nucleic acid comprising the sequence (SEQ ID NO: 42)
ATGGGCAGCAGCCATCATCATCATCATCACAGCAGCGGCCTGGTGCC

GCGCGGCAGCCATATGCTCGAGTACGGCCGCAAGAAACGCCGCCAGC

GCCGCCGCTATCCATATGACGTCCCAGACTATGCTATGGCATCTATG

ACTGGAGGACAACAAATGGGAAGAGACCCAGACCTCGAACAAAGAGC

AGAAGAACTAGCAAGAGAAAACGAAGAACTACTAGAAAAAGAAGCAG

AAGAACTAGAACAAGAAAATGCAGAGCTAGAGGGCGAGTGCCAAGGG

CTAGAGGCGCGGAATCGGGAGCTGAGGGAGAGGGCAGAGTCAGTGTA

G.

pVEC is an 18-amino-acid-long peptide derived from the murine sequence of the cell-adhesion molecule, vascular endothelial cadherin, extending from amino acid 615-632 (Elmquist et al., Exp. Cell Res., 269(2):237-44, 2001). pVEC comprises the amino acid sequence LLIILRR-RIRKQAHAH (SEQ ID NO: 43), or a conservative variant thereof.

MTSs, or membrane translocating sequences, are those portions of certain peptides which are recognized by the acceptor proteins that are responsible for directing nascent translation products into the appropriate cellular organelles for further processing (Lindgren et al., Trends in Pharmacological Sciences, 21(3):99-103, 2000; Brodsky, J. L., Int. Rev. Cyt., 178:277-328, 1998; Zhao et al., J. Immunol. Methods, 254(1-2):137-45, 2001). An MTS of particular relevance is MPS peptide, a chimera of the hydrophobic terminal domain of the viral gp41 protein and the nuclear localization signal from simian virus 40 large antigen; it represents one combination of a nuclear localization signal and a membrane translocation sequence that is internalized independent of temperature, and functions as a carrier for oligonucleotides (Lindgren et al., Trends in Pharmacological Sciences, 21(3):99-103, 2000; Morris et al., Nucleic Acids Res., 25:2730-36, 1997). MPS comprises the amino acid sequence GALFLGWLGAAGSTMGAWSQPKKKRKV (SEQ ID NO: 44), or a conservative variant thereof.

Model amphipathic peptides, or MAPs, form a group of peptides that have, as their essential features, helical amphipathicity and a length of at least four complete helical turns (Scheller et al., J. Peptide Science, 5(4):185-94, 1999; Hallbrink et al., Biochim. Biophys. Acta., 1515(2):101-09, 2001). An exemplary MAP comprises the amino acid sequence KLALKLALKALKAALKLA-amide (SEQ ID NO: 45), or a conservative variant thereof.

In certain embodiments, the cell-penetrating peptides described above are covalently bound to the d/n-ATF5, e.g., via a peptide bond. In certain embodiments the cell-penetrating peptide is operably linked to a d/n-ATF5 via recombinant DNA technology. For example, the d/n-ATF5 can be introduced either upstream (for linkage to the amino terminus of the cell-penetrating peptide) or downstream (for linkage to the carboxy terminus of the cell-penetrating peptide), or both, of a nucleic acid sequence encoding the cell-penetrating peptide of interest. Such fusion sequences comprising both the d/n-ATF5 encoding nucleic acid sequence and the cell-penetrating peptide encoding nucleic acid sequence can be expressed using techniques well known in the art.

In certain embodiments the d/n-ATF5 can be operably linked to the cell-penetrating peptide via a non-covalent linkage. In certain embodiments such non-covalent linkage is mediated by ionic interactions, hydrophobic interactions, hydrogen bonds, or van der Waals forces.

In certain embodiments the d/n-ATF5 is operably linked to the cell penetrating peptide via a chemical linker. Examples of such linkages typically incorporate 1-30 non-hydrogen atoms selected from the group consisting of C, N, O, S and P. Exemplary linkers include, but are not limited to, a substituted alkyl or a substituted cycloalkyl. Alternately, the heterologous moiety may be directly attached (where the linker is a single bond) to the amino or carboxy terminus of the cell-penetrating peptide. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. In certain embodiments, the linker incorporates less than 20 nonhydrogen atoms and are composed of any combination of ether, thioether, urea, thiourea, amine, ester, carboxamide, sulfonamide, hydrazide bonds and aromatic or heteroaromatic bonds. In certain embodiments, the linker is a combination of single carbon-carbon bonds and carboxamide, sulfonamide or thioether bonds.

A general strategy for conjugation involves preparing the cell-penetrating peptide and the d/n-ATF5 components separately, wherein each is modified or derivatized with appropriate reactive groups to allow for linkage between the two. The modified d/n-ATF5 is then incubated together with a cell-penetrating peptide that is prepared for linkage, for a sufficient time (and under such appropriate conditions of temperature, pH, molar ratio, etc.) as to generate a covalent bond between the cell-penetrating peptide and the d/n-ATF5.

The present invention contemplates the use of proteins and protein analogues generated by synthesis of polypeptides in vitro, e.g., by chemical means or in vitro translation of mRNA. For example, ATF5 and inhibitors thereof may be synthesized by methods commonly known to one skilled in the art (*Modern Techniques of Peptide and Amino Acid Analysis* (New York: John Wiley & Sons, 1981); Bodansky, M., *Principles of Peptide Synthesis* (New York: Springer-Verlag New York, Inc., 1984). Examples of methods that may be employed in the synthesis of the amino acid sequences, and analogues of these sequences, include, but are not limited to, solid-phase peptide synthesis, solution-method peptide synthesis, and synthesis using any of the commercially-available peptide synthesizers. The amino acid sequences of the present invention may contain coupling agents and protecting groups, which are used in the synthesis of protein sequences, and which are well known to one of skill in the art.

As used herein, "amino acid residue," "amino acid," or "residue," includes genetically encoded amino acid residues and non-genetically encoded amino acid residues, e.g., non-genetically encoded amino acid residues or non-natural amino acids include, but are not limited to D-enantiomers of naturally occurring chiral amino acids, β-alanine (β-Ala); 2,3-diaminopropionic acid (Dpr); nipecotic acid (Nip); pipecolic acid (Pip); ornithine (Orn); citrulline (Cit); t-butylalanine (t-BuA); 2-t-butylglycine (t-BuG); N-methylisoleucine (MeIle); phenylglycine (PhG); cyclohexylalanine (ChA); norleucine (Nle); naphthylalanine (Nal); 4-chlorophenylalanine (Phe(4-Cl)); 2-fluorophenyl alanine (Phe(2-F)); 3-fluorophenyl alanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe (pNH2)); N-methyl valine (MeVal); homocysteine (hCys), homophenylalanine (hPhe); homoserine (hSer); hydroxyproline (Hyp); homoproline (hPro); and the corresponding D-enantiomer of each of the foregoing, e.g., D-β-Ala, D-Dpr, D-Nip, D-Orn, D-Cit, D-t-BuA, D-t-BuG, D-MeIle, D-PhG, D-ChA, D-Nle, D-Nal, D-Phe(4-Cl), D-Phe(2-F), D-Phe(3-F), D-Phe(4-F), D-Pen, D-Tic, D-Thi, D-MSO, D-hArg, D-AcLys, D-Dbu, D-Dab, D-Phe(pNH2), D-MeVal, D-hCys, D-hPhe, D-hSer, D-Hyp, and D-hPro. Additional non-genetically encoded amino acid residues include 3-aminopropionic acid; 4-aminobutyric acid; isonipecotic acid (Inp); aza-pipecolic acid (azPip); aza-proline (azPro); α-aminoisobutyric acid (Aib); ε-aminohexanoic acid (Aha); δ-aminovaleric acid (Ava); N-methylglycine (MeGly).

In certain embodiments, the cell-penetrating dominant-negative ATF5 comprises a sequence selected from the group consisting of: (1)

(SEQ ID NO: 15)
MGSSHHHHHHESSGLVPRGSHMRQIKIWFQNRRMKWKK*DYKDDD*

*DK*MASMTGGQQMGRDPDLEQRAEELARENEELLEKEAEELEQENAE

LEGECQGLEARNRELRERAESV, where the underlined residues (MG-HM) are a 6×His-tag leader sequence ("6×His" disclosed as SEQ ID NO: 16), the bold residues (RQ-KK) are a Penetratin sequence, the italicized residues (DY-DK) are a Flag tag, the residues with no font modification (MA-PD) are spacer amino acids, the bold and italicized residues (LE-AE) are a d/n sequence, and the bold and underlined residues (LE-SV) are an ATF5 leucine zipper truncated after its first Valine; (2)

(SEQ ID NO: 17)
MGSSHHHHHHSSGLVPRGSHMLEYGRKKRRQRRR*YPYDVPDYA*

MASMTGGQQMGRDPDLEQRAEELARENEELLEKEAEELEQENAE

LEGECQGLEARNRELRERAESV, where the underlined residues (MG-LE) are a 6×His-tag leader sequence ("6×His" disclosed as SEQ ID NO: 16), the bold residues (YG-RR) are a TAT sequence, the italicized residues (YP-YA) are an HA tag, the residues with no font modification (MA-PD) are spacer amino acids, the bold and italicized residues (LE-AE) are a d/n sequence, and the bold and underlined residues (LE-SV) are an ATF5 leucine zipper truncated after its first Valine; (3)

(SEQ ID NO: 18)
MGSSHHHHHHSSGLVPRGSHMRQIKIWFQNRRMKWKKLEQ

RAEELARENEELLEKEAEELEQENAE*LEGECQGLEARNREL*

*KERAE*SV where the where the underlined residues (MG-HM) are a 6×His-tag leader sequence ("6×His" disclosed as SEQ ID NO: 16), the bold residues (RQ-KK) are a Penetratin sequence, the italicized residues (LE-AE) are a d/n sequence, and the bold and underlined residues (LE-SV) are an ATF5 leucine zipper truncated after its first Valine; and (4)

(SEQ ID NO: 19)
RQIKIWFQNRRMKWKKLEQRAEELARENEELLEKEAEELEQ

ENAE*LEGECQGLEARNRELKERAE*SV where the bold residues (RQ-KK) are a Penetratin sequence, the italicized residues (LE-AE) are a d/n sequence, and the bold and underlined residues (LE-SV) are an ATF5 leucine zipper truncated after its first Valine. In certain embodiments, the cell-penetrating dominant-negative ATF5 is chemically synthesized.

4.2 Use of D/N-ATF5 Compositions

In accordance with methods described herein, ATF5 can be inhibited in a cell by disabling, disrupting, or inactivating the function or activity of ATF5 in the cell. For example, the function or activity of ATF5 in a cell may be inhibited by providing a dominant negative-ATF5 molecule capable of inhibiting the function or activity of native ATF5 in the cell. In certain embodiments, the d/n-ATF5 is a CP-d/n-ATF5.

In certain embodiments, function or activity of the ATF5 in the cell is inhibited by at least 1%, 5%, 10%, 20%, 30%, 40%, 50%, or greater (inclusive of intermediate ranges between those explicitly recited, e.g., 5-10%, 10-20%, 20-30%, 40-50%, or greater than 50% including 50%-100%). In certain embodiments, function or activity of the ATF5 is decreased by inhibiting expression of ATF5. Such expression can be inhibited by at least 1%, 5%, 10%, 20%, 30%, 40%, 50%, or greater (inclusive of intermediate ranges between those explicitly recited, e.g., 5-10%, 10-20%, 20-30%, 40-50%, or greater than 50% including 50%-100%). In certain embodiments, expression is decreased by 60%, 80%, or 90%, as outlined in FIG. 11A-11E.

In certain embodiments, the present invention provides methods for treating or preventing a tumor in a subject in need of treatment, comprising administering to the subject a pharmaceutical composition comprising a CP-d/n-ATF5 and, optionally, a pharmaceutically-acceptable carrier. The CP-d/n-ATF5 is provided in an amount that is effective to treat the tumor in a subject to whom the composition is administered. As used herein, the phrase "effective" means effective to ameliorate or minimize the clinical impairment or symptoms of the tumor. For example, the clinical impairment or symptoms of the tumor may be ameliorated or minimized by diminishing any pain or discomfort suffered by the subject; by extending the survival of the subject beyond that which would otherwise be expected in the absence of such treatment; by inhibiting or preventing the development or spread of the tumor; or by limiting, suspending, terminating, or otherwise controlling the maturation and proliferation of cells in the tumor. The amount of CP-d/n-ATF5 effective to treat a tumor in a subject in need of treatment will vary depending upon the particular factors of each case, including the type of tumor, the stage of the tumor, the subject's weight, the severity of the subject's condition, and the method of administration. This amount can be readily determined by the skilled artisan.

As used herein, the term "tumor" refers to a pathologic proliferation of cells, and includes a neoplasia. The term "neoplasia", and related terms as further used herein, refers to the uncontrolled and progressive multiplication of tumor cells under conditions that would not elicit, or would cause cessation of, multiplication of normal cells. Neoplasia results in the formation of a "neoplasm", which is defined herein to mean any new and abnormal growth, particularly a new growth of tissue, in which the growth of cells is uncontrolled and progressive. As used herein, neoplasms include, without limitation, morphological irregularities in cells in tissue of a subject, as well as pathologic proliferation of cells in tissue of a subject, as compared with normal proliferation in the same type of tissue. Additionally, neoplasms include benign tumors and malignant tumors. Malignant neoplasms are distinguished from benign in that the former show a greater degree of anaplasia, or loss of differentiation and orientation of cells, and have the properties of invasion and metastasis. Thus, neoplasia includes "cancer" including hematological cancers, which herein refers to a proliferation of tumor cells having the unique trait of loss of normal controls, resulting in unregulated growth, lack of differentiation, local tissue invasion, and metastasis.

Additionally, as used herein, the term "neural tumor" refers to a tumorigenic form of neural cells (i.e., transformed neural cells), and includes astrocytoma cells (i.e., cells of all astrocytomas, including, without limitation, Grades I-IV astrocytomas, anaplastic astrocytoma, astroblastoma, astrocytoma fibrillare, astrocytoma protoplasmaticum, gemistocytic astrocytoma, and glioblastoma multiforme), gliomas, medulloblastomas, neuroblastomas, and other brain tumors. Brain tumors invade and destroy normal tissue, producing such effects as impaired sensorimotor and cognitive function, increased intracranial pressure, cerebral edema, and compression of brain tissue, cranial nerves, and cerebral vessels. Metastases may involve the skull or any intracranial structure. The size, location, rate of growth, and histologic grade of malignancy determine the seriousness of brain tumors. Nonmalignant tumors grow slowly, with few mitoses, no necrosis, and no vascular proliferation. Malignant tumors grow more rapidly, and invade other tissues. However, they rarely spread beyond the CNS, because they cause death by local growth.

Brain tumors may be classified by site (e.g., brain stem, cerebellum, cerebrum, cranial nerves, ependyma, meninges, neuroglia, pineal region, pituitary gland, and skull) or by histologic type (e.g., meningioma, primary CNS lymphoma, or astrocytoma). Common primary childhood tumors are cerebellar astrocytomas and medulloblastomas, ependymomas, gliomas of the brain stem, neuroblastomas, and congenital tumors. In adults, primary tumors include meningiomas, schwannomas, and gliomas of the cerebral hemispheres (particularly the malignant glioblastoma multiforme and anaplastic astrocytoma, and the more benign astrocytoma and oligodendroglioma). Overall incidence of intracranial neoplasms is essentially equal in males and females, but cerebellar medulloblastoma and glioblastoma multiforme are more common in males.

Gliomas are tumors composed of tissue representing neuroglia in any one of its stages of development. They account for 45% of intracranial tumors. Gliomas can encompass all of the primary intrinsic neoplasms of the brain and spinal cord, including astrocytomas, ependymomas, and neurocytomas. Astrocytomas are tumors composed of transformed astrocytes, or astrocytic tumor cells. Such tumors have been classified in order of increasing malignancy: Grade I consists of fibrillary or protoplasmic astrocytes; Grade II is an astroblastoma, consisting of cells with abundant cytoplasm and two or three nuclei; and Grades III and IV are forms of glioblastoma multiforme, a rapidly growing tumor that is usually confined to the cerebral hemispheres and composed of a mixture of astrocytes, spongioblasts, astroblasts, and other astrocytic tumor cells. Astrocytoma, a primary CNS tumor, is frequently found in the brain stem, cerebellum, and cerebrum. Anaplastic astrocytoma and glioblastoma multiforme are commonly located in the cerebrum. The present invention additionally provides methods for promoting apoptosis in a neoplastic cell comprising contacting the neoplastic cell with an ATF5 inhibitor. The neoplastic cell can be selected from the group consisting of: breast, ovary, endometrium, gastric, colon, liver, pancreas, kidney, bladder, prostate, testis, skin, esophagus, tongue, mouth, parotid, larynx, pharynx, lymph node, lung, and brain. In one embodiment, the neoplastic cell is selected from the group consisting of glioblastoma, astrocytoma, glioma, medulloblastoma and neuroblastoma.

For example, but not by way of limitation, cell lines shown through testing to be susceptible to TAT-d/n-ATF5 (1-3 µM range) include: U87 (human glioblastoma); U373 (human glioblastoma); LN229 (human glioblastoma); C6 (rat glioblastoma); Mel501 (human melanoma); H2452 (human mesothelioma); MDA-MB-468 (human breast cancer). In addition, a non-limiting list of cell lines shown through testing to be susceptible to PEN-d/n-ATF5 (3 µM) include: Panc-1 (human pancreatic cancer); SH-SYSY (human neuroblastoma cells); and HCT-116 (colon-carcinoma cancer). The method of the present invention can be performed in vitro as well as in vivo in a subject. As used herein, "apoptosis" refers to cell death which is wholly or partially genetically controlled.

As outlined in the examples below, certain CP-d/n-ATF5 compositions are effective anti-neoplastic agents across species, e.g., rat/mouse CP-d/n-ATF5 is effective against human cancers. Thus, in certain embodiments the CP-d/n-ATF5 can comprise a rat or mouse d/n-ATF5 peptide sequence and the subject may be any animal, including, but not limited to a mammal (e.g., a human, domestic animal, or commercial animal). In certain embodiments, the CP-d/n-ATF5 can comprise a rat or mouse d/n-ATF5 peptide sequence and the subject is a human.

In accordance with the method of the present invention, CP-d/n-ATF5 can be administered to a human or animal subject by known procedures, including, without limitation, oral administration, parenteral administration, intranasal administration and transdermal administration. Preferably, the inhibitors or factors are administered parenterally, by intracranial, intraspinal, intrathecal, or subcutaneous injection.

4.3 D/N-ATF5 Pharmaceutical Compositions

For oral administration, CP-d/n-ATF5 can be formulated as capsules, tablets, powders, granules, or as a suspension. The CP-d/n-ATF5 formulation may have conventional additives, such as lactose, mannitol, corn starch, or potato starch. The CP-d/n-ATF5 formulation also may be presented with binders, such as crystalline cellulose, cellulose derivatives, acacia, corn starch, or gelatins. Additionally, the CP-d/n-ATF5 formulation may be presented with disintegrators, such as corn starch, potato starch, or sodium carboxymethylcellulose. The CP-d/n-ATF5 formulation also may be presented with dibasic calcium phosphate anhydrous or sodium starch glycolate. Finally, the CP-d/n-ATF5 formulation may be presented with lubricants, such as talc or magnesium stearate.

For parenteral administration (i.e., administration by injection through a route other than the alimentary canal), CP-d/n-ATF5 can be combined with a sterile aqueous solution that is preferably isotonic with the blood of the subject. Such a CP-d/n-ATF5 formulation can be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The CP-d/n-ATF5 formulation can be presented in unit or multi-dose containers, such as sealed ampoules or vials. The CP-d/n-ATF5 formulation can be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual.

In certain embodiments, the CP-d/n-ATF5 formulation is prepared for intranasal delivery. For nasal administration, solutions or suspensions comprising the CP-d/n-ATF5 formulation can be prepared for direct application to the nasal cavity by conventional means, for example with a dropper, pipette or spray. Other means for delivering the nasal spray composition, such as inhalation via a metered dose inhaler (MDI), may also be used according to the present invention. Several types of MDIs are regularly used for administration by inhalation. These types of devices can include breath-actuated MDI, dry powder inhaler (DPI), spacer/holding chambers in combination with MDI, and nebulizers. The term "MDI" as used herein refers to an inhalation delivery system comprising, for example, a canister containing an active agent dissolved or suspended in a propellant optionally with one or more excipients, a metered dose valve, an actuator, and a mouthpiece. The canister is usually filled with a solution or suspension of an active agent, such as the nasal spray composition, and a propellant, such as one or more hydrofluoroalkanes. When the actuator is depressed a metered dose of the solution is aerosolized for inhalation. Particles comprising the active agent are propelled toward the mouthpiece where they may then be inhaled by a subject. The formulations may be provided in single or multidose form. For example, in the case of a dropper or pipette, this may be achieved by the patient administering an appropriate, predetermined volume of the solution or suspension. In the case of a spray, this may be achieved for example by means of a metering atomising spray pump. To improve nasal delivery and retention the components according to the invention may be encapsulated with cyclodextrins, or formulated with agents expected to enhance delivery and retention in the nasal mucosa.

Commercially available administration devices that are used or can be adapted for nasal administration of a composition of the invention include the AERONEB™ (Aerogen, San Francisco, Calif.), AERONEB GO™ (Aerogen); PARI LC PLUS™, PARI BOY™ N, PARI™ eflow (a nebulizer disclosed in U.S. Pat. No. 6,962,151), PARI LC SINUS™, PARI SINUSTAR™, PARI SINUNEB™, VibrENT™ and PARI DURANEB™ (PART Respiratory Equipment, Inc., Monterey, Calif. or Munich, Germany); MICROAIR™ (Omron Healthcare, Inc, Vernon Hills, Ill.), HALOLITE™ (Profile Therapeutics Inc, Boston, Mass.), RESPIMAT™ (Boehringer Ingelheim, Germany), AERODOSE™ (Aerogen, Inc, Mountain View, Calif.), OMRON ELITE™ (Omron Healthcare, Inc, Vernon Hills, Ill.), OMRON MICROAIR™ (Omron Healthcare, Inc, Vernon Hills, MABISMIST™ II (Mabis Healthcare, Inc, Lake Forest, Ill.), LUMISCOPE™ 6610, (The Lumiscope Company, Inc, East Brunswick, N.J.), AIRSEP MYSTIQUE™, (AirSep Corporation, Buffalo, N.Y.), ACORN-1™ and ACORN-II™ (Vital Signs, Inc, Totowa, N.J.), AQUATOWER™ (Medical Industries America, Adel, Iowa), AVANEB™ (Hudson Respiratory Care Incorporated, Temecula, Calif.), AEROCURRENT™ utilizing the AEROCELL™ disposable cartridge (AerovectRx Corporation, Atlanta, Ga.), CIRRUS™ (Intersurgical Incorporated, Liverpool, N.Y.), DART™ (Professional Medical Products, Greenwood, S.C.), DEVILBISS™ PULMO AIDE (DeVilbiss Corp; Somerset, Pa.), DOWNDRAFT™ (Marquest, Englewood, Colo.), FAN JET™ (Marquest, Englewood, Colo.), MB-5™ (Mefar, Bovezzo, Italy), MISTY NEB™ (Baxter, Valencia, Calif.), SALTER 8900™ (Salter Labs, Arvin, Calif.), SIDESTREAM™ (Medic-Aid, Sussex, UK), UPDRAFT-II™ (Hudson Respiratory Care; Temecula, Calif.), WHISPER JET™ (Marquest Medical Products, Englewood, Colo.), AIOLOS™ (Aiolos Medicinsk Teknik, Karlstad, Sweden), INSPIRON™ (Intertech Resources, Inc., Bannockburn, Ill.), OPTIMIST™ (Unomedical Inc., McAllen, Tex.), PRODOMO™, SPIRA™ (Respiratory Care Center, Hameenlinna, Finland), AERx™ Essence™ and Ultra™, (Aradigm Corporation, Hayward, Calif.), SONIK™ LDI Nebulizer (Evit Labs, Sacramento, Calif.), ACCUSPRAY™ (BD Medical, Franklin Lake, N.J.), ViaNase ID™ (electronic atomizer; Kurve, Bothell, Wash.), OptiMist™ device or OPTINOSE™ (Oslo, Norway), MAD Nasal™ (Wolfe Tory Medical, Inc., Salt Lake City, Utah), Freepod™ (Valois, Marly le Roi, France), Dolphin™ (Valois), Monopowder™ (Valois), Equadel™ (Valois), VP3™ and VP7™ (Valois), VP6 Pump™ (Valois), Standard Systems Pumps™ (Ing. Erich Pfeiffer, Radolfzell, Germany), AmPump™ (Ing. Erich Pfeiffer), Counting Pump™ (Ing. Erich Pfeiffer), Advanced Preservative Free System™ (Ing. Erich Pfeiffer), Unit Dose System™ (Ing. Erich Pfeiffer), Bidose System™ (Ing. Erich Pfeiffer), Bidose Powder System™ (Ing. Erich Pfeiffer), Sinus Science™ (Aerosol Science Laboratories, Inc., Camarillo, Calif.), ChiSys™ (Archimedes, Reading, UK), Fit-Lizer™ (Bioactis, Ltd, a SNBL subsidiary (Tokyo, J P), Swordfish V™ (Mystic Pharmaceuticals, Austin, Tex.), DirectHaler™ Nasal (DirectHaler, Copenhagen, Denmark) and SWIRLER™ Radioaerosol System (AMICI, Inc., Spring City, Pa.).

For transdermal administration, CP-d/n-ATF5 can be combined with skin penetration enhancers, such as propylene glycol, polyethylene glycol, isopropanol, ethanol, oleic acid, N-methylpyrrolidone, and the like, which increase the permeability of the skin to the CP-d/n-ATF5, and permit the CP-d/n-ATF5 to penetrate through the skin and into the bloodstream. The CP-d/n-ATF5 compositions also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch.

The present invention also provides therapeutic compositions, comprising a CP-d/n-ATF5 and, optionally, a pharmaceutically-acceptable carrier. The pharmaceutically-acceptable carrier must be "acceptable" in the sense of being compatible with the other ingredients of the composition, and not deleterious to the recipient thereof. The pharmaceutically-acceptable carrier employed herein is selected from various organic or inorganic materials that are used as materials for pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and viscosity-increasing agents. If necessary, pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others.

The CP-d/n-ATF5 formulations of the present invention can be prepared by methods well-known in the pharmaceutical arts. For example, the CP-d/n-ATF5 can be brought into association with a carrier or diluent, as a suspension or solution. Optionally, one or more accessory ingredients (e.g., buffers, flavoring agents, surface active agents, and the like) also can be added. The choice of carrier will depend upon the route of administration. The pharmaceutical composition would be useful for administering the CP-d/n-ATF5 to a subject to treat a tumor and/or neoplastic cell, as discussed herein. The CP-d/n-ATF5 is provided in an amount that is effective to treat the tumor and/or neoplastic cell in a subject to whom the pharmaceutical composition is administered. That amount may be readily determined by the skilled artisan, as described above.

Compositions of the present disclosure can further include other therapeutic agents. For example, they can include any one or more anti-cancer agents. In certain embodiments, the one or more anti-cancer agent will be selected from the group consisting of: alkylating agents; anti-metabolites; anti-microtubule agents; topoisomerase inhibitors, antibiotics, and antibodies/antibody-drug conjugates. The amounts of those anti-cancer agents in compositions of the present disclosure can, in certain embodiments, be reduced as compared to normal doses of such agents administered in a similar fashion.

The present invention also provides kits for use in treating and/or preventing tumors and/or neoplastic cells. In certain embodiments the kits comprise a CP-d/n-ATF5 molecule and a pharmaceutically acceptable carrier. In certain embodiments the kits further comprise a means for administration, for example, but not limited to, a pre-filled syringe, pen, pump, or other pre-filled device for parenteral administration of the CP-d/n-ATF5. In certain embodiments, the kits will comprise a CP-d/n-ATF5 formulated for intranasal delivery and a means for intranasal administration, such as, but not limited to, a metered dose inhaler or other commercially available administration device which can be used or can be adapted for nasal administration of a composition as described herein.

The present invention is described in the following Examples, which are set forth to aid in the understanding of the invention, and should not be construed to limit in any way the scope of the invention as defined in the claims which follow thereafter.

5. EXAMPLES

5.1 CP-d/n-ATF5 Example

5.1.1 Materials & Methods

Truncation of d/n ATF-5. Using pQC eGFP-d/n-ATF5 plasmid (see, Angelastro et al., J Neurosci 2003; 23(11): 4590-600) as template, PCR using upstream primer 5'-TCC GCG GCC GCA CCG GTC GCC-3' (SEQ ID NO: 46) and downstream primer 5'-CTC GAG GAT ATC TCA GTT ATC TAC ACT GAC TCT GCC CTC TCC CTC AG-3' (SEQ ID NO: 47) truncated 75 base pairs from the 3' plasmid. Electrophoretically purified eGFP-d/n ATF5-tr (tr=truncated) cDNA was ligated into pGEM-T Easy Cloning vector (Promega), transformed into DH5α cells, and plated onto LB agar-Ampicillin plates with blue-white selection. Selected colonies were amplified overnight in LB plus ampicillin. Plasmids isolated from the culture (mini-prep, Invitrogen) were digested with AgeI and EcoRV followed by agarose gel electrophoresis to verify d/n-ATF5-tr insertion and inserts underwent DNA sequencing for verification. AgeI/EcoRV digested eGFP-d/n-ATF5-tr cDNA was ligated into AgeI/coRV-digested purified pQCXIX (Clontech) expression vector. The ligation mixture was used to transform DH5α bacteria and the product was verified by AgeI/EcoRV digestion and gel electrophoresis from minipreps of bacterial cultures and DNA sequencing of uncut plasmid. The pQC-eGFP-d/n-ATF5-tr plasmid was grown in Maxiprep (Invitrogen).

CP-6×His-Pen-Flag-tagged-d/n-ATF5 protein ("6×His" disclosed as SEQ ID NO: 16) production and bioassay. To create Cell-Penetrating-6×His-Penetratin-Flag-tagged-d/n-ATF5-tr (CP-6×His-Pen-Flag-tagged-d/n-ATF5-tr) cDNA ("6×His" disclosed as SEQ ID NO: 16), PCR was first employed using upstream primer 5'-TTA ATT AAG CCG CCA TGG ATG CGT CAA ATT AAA ATT TGG TTT CAA AAT CGT CGT ATG AAA TGG AAA AAA ATG GAC TAC AAG GAC GAT GAT-3' (SEQ ID NO: 48) and downstream primer 5'-CTC GAG GGA TCC TCA GTT ATC TAC ACT GAC TCT GCC CTC TCC CTC AG-3' (SEQ ID NO: 49) and pQC-Flag-d/n-ATF5-tr as template. The product was purified after gel electrophoresis and ligated into pGEM-T Easy cloning vector. This was transformed into DH5α cells and for white colony selection. Miniprep clones were digested with EcoRV followed by gel electrophoresis and sequencing of uncut plasmid to verify the insert. To insert a 6×His tag (SEQ ID NO: 16) at the N-terminus, Pen-d/n-ATF5-RP-tr was cloned into the pET-15b expression vector (Novagen). Both pET-15b and pGEMT-Pen-d/n-ATF5-RP-tr vectors were digested with Nde-1 and BamH1 and the cut Pen-d/n-ATF5-RP-tr was separated from pGEMT by gel electrophoresis. Likewise, cut pET-15b was separated from the insert by gel electrophoresis. Both pET-15b and Pen-d/n-ATF5-RP-tr were excised from the gel and purified and then ligated using T4 DNA ligase. The ligated material was used to transform DH5α cells and colonies selected. Miniprepped constructs were digested with Xba-1 and EcoRV to verify the presence of vector and Pen-d/n-ATF5-RP insert using gel electrophoresis. The pET-15b-Pen-d/n-ATF5-RP was verified by DNA sequencing for correct orientation and sequence.

To generate CP-6×His-Pen-Flag-tagged-d/n-ATF5 protein ("6×His" disclosed as SEQ ID NO: 16), the expression construct was transformed into BL21 DE3 pLysS cells (Novagen). Colonies were selected and amplified in LB. Peptide production was induced with 1 mM IPTG and verified by SDS-PAGE. Once protein induction was verified, extractions were accomplished with detergent-based BugBuster master mix system (Novagen). Isolation and purification of the Pen-Flag-tagged-d/n-ATF5 peptide was accomplished using its N-terminal 6×HIS-tag (SEQ ID NO: 16) and cobalt spin column system (HisPur; Thermo Fisher). Purified peptide was desalted and buffer-exchanged to PBS using Zeba de-salt spin columns (Thermo Fisher) or G-25 Sephadex (GE Health Care). Desalted protein was sterile-filtered using 0.20 μm polyethersulfone membrane syringe filters (Sarstedt). Lastly, the peptide was concentrated to 1-2 mg/ml using Amicon Ultra-4 centrifugal filter devices (3000 MW Cutoff).

A control peptide (Pen-Flag-tagged-Control) was created and produced using the same methodology by eliminating the d/n-ATF5 portion of the construct using PCR upstream primer 5'-CCCGGGCATATGCGTCAAATTAAAATTTGGTTT-3' (SEQ ID NO: 50) and downstream primer 5'-CTC-GAGGGATCCTCAGTTATCTAGTCTGGGTCTCTTCC-3' (SEQ ID NO: 51).

Mass Spectroscopy.

Linear MALDI-TOF Analysis for Nominal Molecular Mass Measurement:

Matrix-assisted laser desorption/ionization (MALDI) measurements were acquired on a MALDI-TOF/TOF mass spectrometer (4700 Proteomics Analyzer, AB Sciex) equipped with a 200 Hz ND-YAG laser source (355 nm). Samples were spotted onto the MALDI plate with an equivolume of MALDI matrix (sinapinic acid in 50% ACN/0.1% FA, Fluka) and air dried. The instrument was operated at an accelerating voltage of 20 kV. Spectra were taken from signal averaging of 4,000 laser shots. Mass Spectra analyses were performed in positive ion linear mode with a mass range of 10,000-60,000 m/z. Data were further analyzed by Data Explorer 4.5 (AB Sciex).

LC-MS Analysis:

Samples were injected onto an Aeris Widepore XB-C8 column (3.6μ, 2.10×50 mm). A standard reverse phase gradient was run over 8 minutes at flow rate of 250μ/min and the eluent monitored by a LTQ-OrbitrapXL mass spectrometer (Thermo Fisher) in profile mode. Ion Max Source (Thermo Fisher) was used as the electrospray ionization source and source parameters were 5 kV spray voltage, capillary temperature of 275° C. and sheath gas setting of 20. Spectral data were acquired at a resolution setting of 15,000 FWHM with the lockmass feature.

Bioactivity of the pQC-eGFP-d/n ATF-5tr product (C-terminally truncated d/n-ATF5). Purified pQC-eGFP-d/n-ATF5-tr, full-length pQC-eGFP-d/n-A TF5 positive control or pQC-eGFP negative control plasmids were transfected into rat C6 glial cells in 24 well plates using Lipofectamine 2000 (Invitrogen). After 48 hours, cells were stained with DAPI and 10 random fields were viewed under fluorescent microscopy at 40×. Cells displaying fragmented, condensed chromatin were scored as apoptotic and quantified relative to total cells (n=3 independent experiments).

Cell penetrating (CP)-6×His-Pen-Flag-tagged-d/n-ATF5 ("6×His" disclosed as SEQ ID NO: 16) bioassay. For peptide bioassays, rat C6 glioblastoma cells were maintained in serum-free DMEM for 2 hours, and then in DMEM/0.5% FBS without or with 3 μM Penetratin (Pen)-d/n-ATF5-RP peptide or (Penetratin) Pen-control-RP. After 5 days, cells were stained with DAPI and percent of apoptotic cells determined as described above.

Imaging of internalized Pen-d/n-ATF5-RP (Recombinant Protein). Rat C6 cells (from Jeff Bruce; Columbia University, New York; authenticated 2004 by grafting into Rat brain Angelastro et al., Oncogene 2006; 25(6):907-16) and U87 cells (purchased and authenticated from the ATCC) were plated on fibronectin-coated confocal microscopy coverslips and maintained overnight. 3 μM each of Pen-d/n-ATF5-RP or Pen-Control-RP were added to wells and incubated for 1, 2, 4, or 24 hours. Cells were washed 3× with PBS to remove extracellular peptide and stained with primary mouse anti-FLAG antibody (Sigma-Aldrich) overnight followed by incubation for two hours with secondary anti-mouse Alexa-568 (Invitrogen). Microscopy used a Carl Zeiss Axiovert 200 with Axiocam video capture or Delta Vision Deconvolution microscope at 0.1-μm optical sections enhanced by Huygens Deconvolution Software. Images of xy and yz planes confirmed co-localization of Pen-d/n-ATF5-RP and DAPI staining.

Retrovirus-induced mouse glioblastoma model and treatment with Pen-d/n-ATF5-RP. As described previously (Arias et al., Oncogene 2012; 31(6):739-51), adult mice were anesthetized and underwent stereotaxic injection of retrovirus expressing PDGF-B and p53-shRNA to generate malignant gliomas. Analgesics were given immediately after surgery. Injected mice were monitored post-surgically and throughout the study period, which ranged from 52 to 438 days. Pen-d/n-ATF5-RP or Pen-Control-RP was administered to tumor-bearing animals in treatments of four subcutaneous or intraperitoneal injections, spaced 1-2 hours apart. The doses were 1 mg/kg (200 μl, 0.9% saline) for each injection. In some experiments as indicated, dosing was repeated 5 days later. Animals injected with 0.9% saline at the same dosing schedule and volume served as controls.

Brain sectioning and staining. As previously described, (Arias et al., Oncogene 2012; 31(6):739-51), mice were euthanized by deep isoflurane anesthesia followed by transcardial perfusion with 10% formalin. Brains were fixed in 4% paraformaldehyde, incubated overnight in 30% sucrose and were mounted in OCT medium, frozen and cut into 14-μm coronal sections. In other cases as indicated, brains of perfused mice were incubated in 10% formalin/PBS for 4-7 days and then paraffin-embedded. Paraffin sections were subjected to antigen retrieval as described (Schrot et al., J Neurooncol 2007; 85(2):149-57). Sections were stained with DAPI and the following: Anti-Flag M2 (1:200; Sigma-Aldrich), rabbit anti-Flag (1:1000, Cell Signaling), rabbit anti-HA (4 μg/ml; sc-805 Santa Cruz Biotechnology), or TUNEL (Roche) and Anti-Flag M2. Sections were visualized with a DAPI filter and immunofluorescence (Alexa 488/568; Invitrogen) or colorimetrically with diaminobenzidine or fast red (Mach2; Biocare Medical) and photographed on a Carl Zeiss Axiovert 200 with Axiocam video.

MRI analysis. Anesthetized (isoflurane and oxygen) mice were fitted intravenously with a 30 gauge catheter, and positioned head first, prone on the scanner bed. MM acquisitions were performed on a Bruker Biospec 7 Tesla magnet operating Paravision v5.1 and outfitted with a 116-mm diameter gradient with integrated shim control. Maximum gradient strength was 450 mT/m. A cross coil configuration was used for imaging brains and a 72-mm ID linear coil was used for RF transmission and a 4 channel phased array coil for RF reception. Pre-contrast and 1 minute post contrast images were acquired with FLASH_3Dslab. Gadolinium was injected intravenously at a dose of 1 μl/g body weight.

5.1.2 Results

Generation of a Cell-Penetrating Form of d/n-ATF5.

Figure 1:
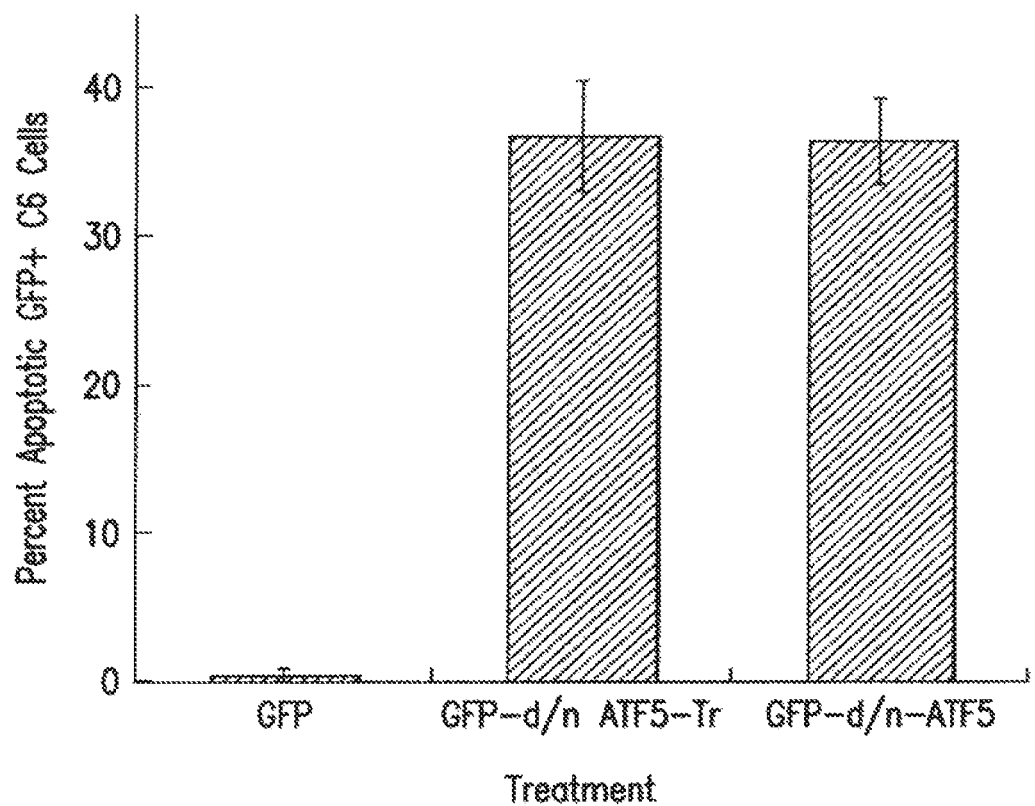

A modified cell-penetrating form of d/n-ATF5 that could be delivered systemically was prepared as outlined herein. This has a potential advantage of rapid biodistribution, reduced immune response, passage through the blood brain barrier, entry into cells, and the capacity reaching widely dispersed tumor cells. The original d/n-ATF5 is an N-terminally truncated form of ATF5 that includes the wild-type leucine zipper domain with an amphipathic α-helical sequence with leucine repeats at every seventh residue replacing the DNA binding domain [Angelastro et al., J Neurosci 2003; 23(10):4590-600]. The resulting protein is capable of interacting with ATF5 and its binding partners via the enhanced leucine zipper region, but not with DNA, and consequently acts as an effective d/n suppressor of ATF5 actions [Angelastro et al., J Neurosci 2003; 23(11):4590-600; Vinson et al., Genes Dev 1993; 7(6):1047-58]. Deletion of the N-terminal domain substantially stabilizes d/n-ATF5 against degradation [Lee et al., Developmental Neurobiology 2012; 72(6):789-804; Uekusa et al., Biochem Biophys Res Commun 2009; 380(3):673-8]. To design a deliverable form of d/n-ATF5, the last 25 amino acids of the protein were first truncated, which includes the C-terminal two valine/valine heptad repeats. Transfection of this deleted construct into C6 glioblastoma cells showed equal effectiveness as the full length d/n-ATF5 in promoting apoptosis (FIG. 1).

Figure 2A:
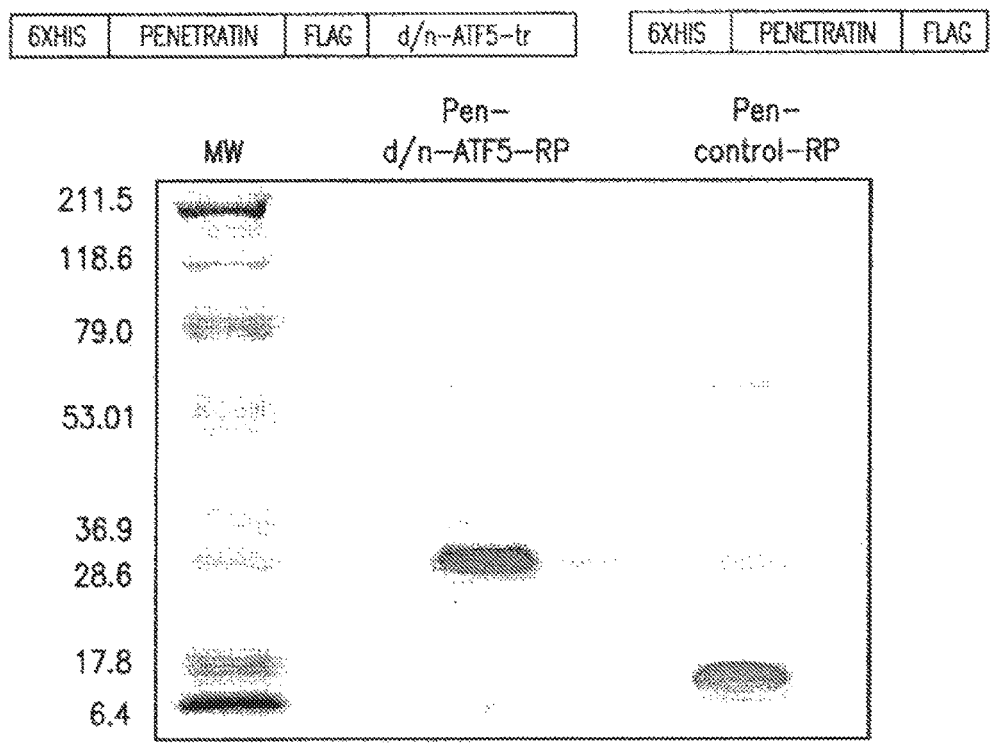
Figure 2B:
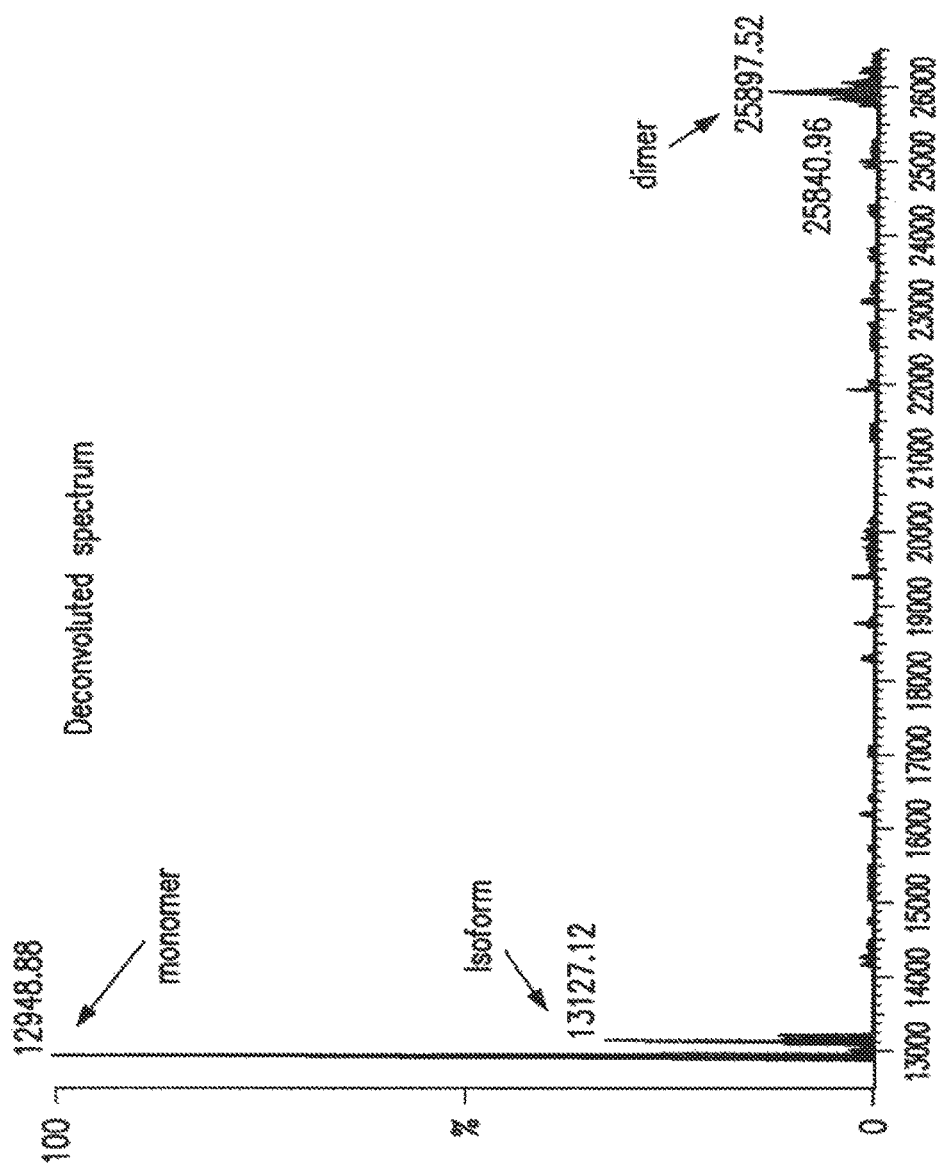

To generate a cell-penetrating form of the C-terminally truncated d/n-ATF5 (d/n-ATF5-tr), an N-terminally Flag-tagged d/n-ATF5-tr construct N-terminally fused to a 6× histidine repeat (SEQ ID NO: 16) followed by a penetratin sequence was designed (FIG. 2A). Penetratin sequence is a 16-amino acid motif from the Antennapedia homeodomain protein permitting passage of fused cargos through biological membranes into cells [Dupont et al., Methods in molecular biology 2011; 683:21-9.]. Milligram quantities of the protein (designated Pen-d/n-ATF5-Recombinant Protein (RP)) were generated by expression in bacteria followed by purification by cobalt resin affinity chromatography using the 6×His sequence (SEQ ID NO: 16). SDS-PAGE showed the purified preparations were more than 95% homogeneous with minor species including what appeared to be aggregated protein multimers. Calculated Mr of Pen-d/n-ATF5-RP with normal bacterial removal of the N-formylmethionine is 12,949.18 Da, but the major purified product shows an apparent molecular mass between 25-28 KDa by SDS-PAGE (FIG. 2A). Wild type ATF5 and the ATF5 leucine zipper can migrate anomalously when subjected to SDS-PAGE and so high resolution LC-HRMS was employed to verify the correct molecular weight of Pen-d/n-ATF5-RP as well as its solution state. The deconvoluted spectra revealed the most abundant form to be the predicted 12,948.7 Da monomer, with a low amount of dimer at 25,897.5 Da (FIG. 2B). Prior studies have also shown that recombinant wild type full-length ATF5 or the bzip domain of ATF5 can form dimers in vitro. Finally, as a control for Pen-d/n-ATF5-RP, a peptide (Pen-Control-RP) was generated by similar means that lacks the d/n-ATF5-tr sequence (FIG. 2A). The purified recombinant control (with a calculated molecular mass of 7,099.98 Da) migrated at an apparent MW of 7,100 Da by SDS-PAGE (FIG. 2A).

Figure 2C:
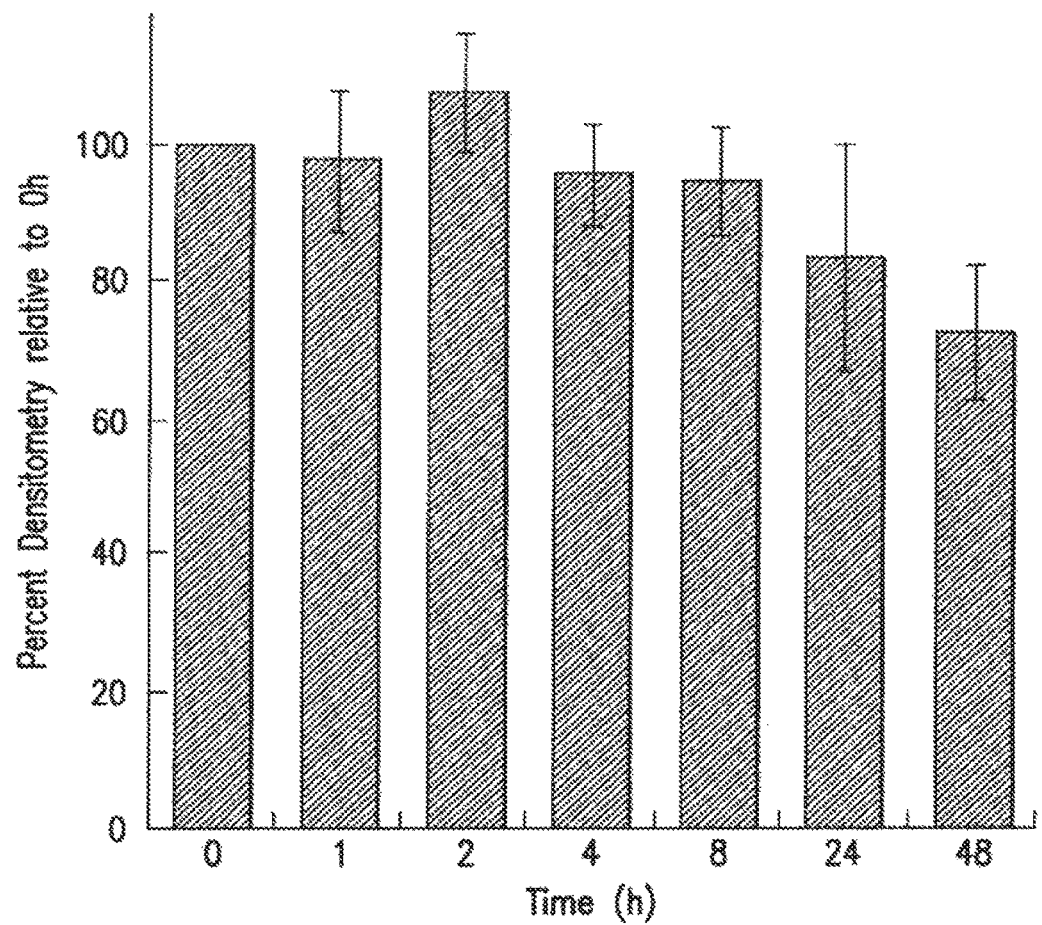

Because Pen-d/n-ATF5-RP is designed for systemic administration, stability in presence of human serum at 37° C. was shown with no significant degradation at 8 h and a mean loss of 28% of full-length protein by 48 h (FIG. 2C).

Pen-d/n-ATF5-RP Rapidly Enters and Causes Apoptosis of Cultured Glioblastoma Cells.

Figure 3B:
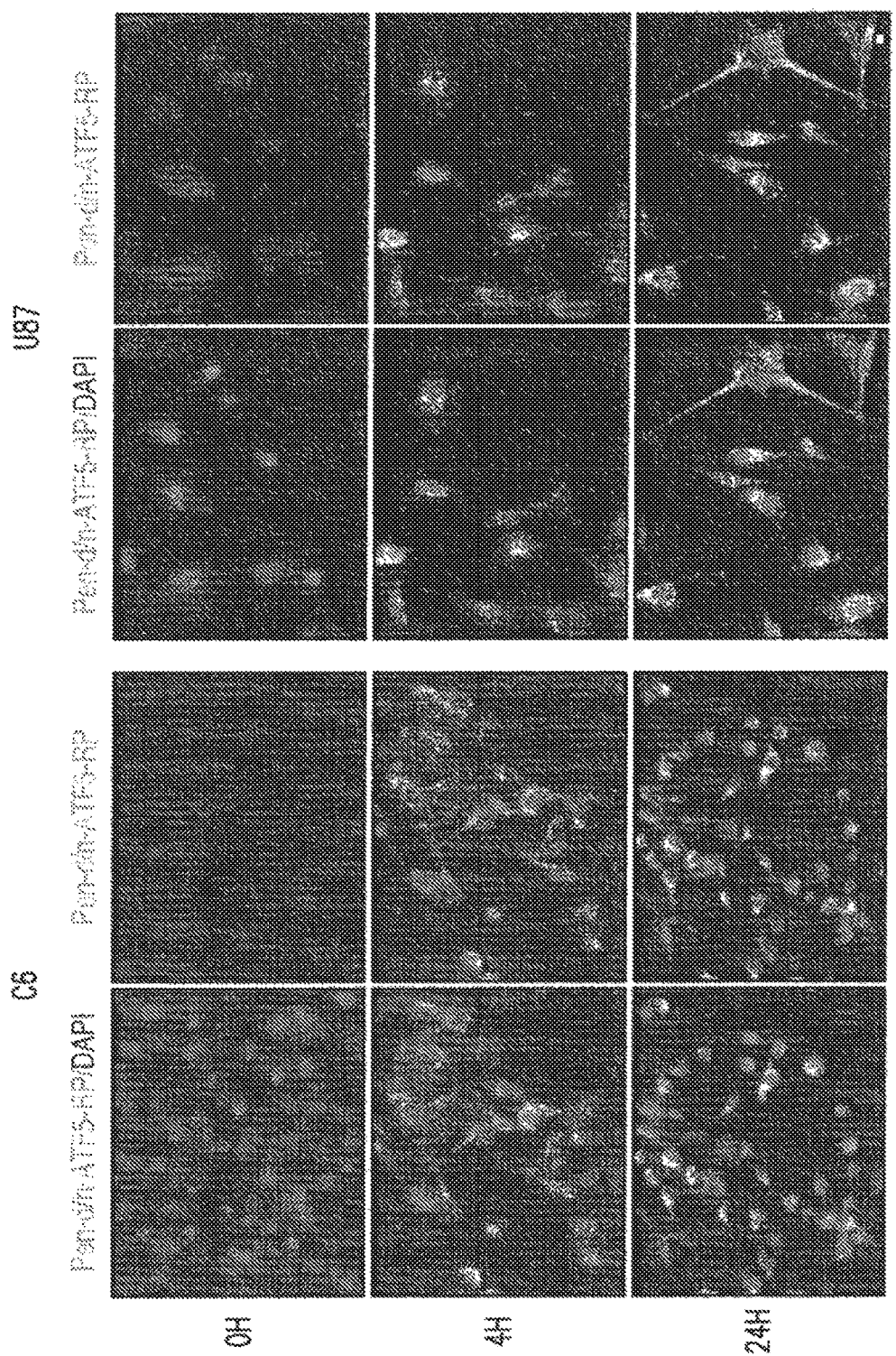

Before carrying out animal experiments, the ability of Pen-d/n-ATF5-RP to enter and kill glioblastoma cells in culture was verified. When added to serum-containing cultures of rat C6 and human U87 glioblastoma cells, both Pen-control-RP and Pen-d/n-ATF5-RP were readily detectable in the cells within 2-4 h and remained detectable for at least 24 h (FIG. 3A, 3B). Confocal microscopy revealed that the peptides were present in both the cytoplasmic and nuclear compartments (FIG. 3A).

Figure 4:
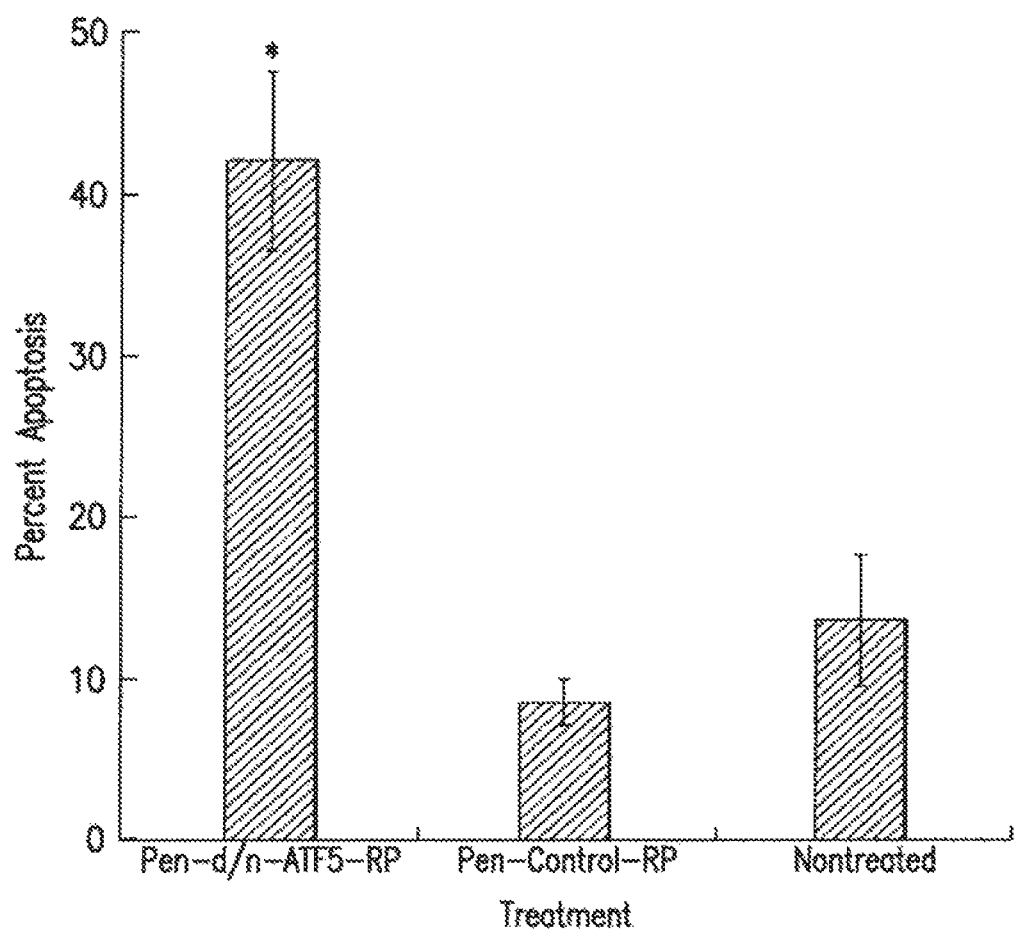
Figure 6D:
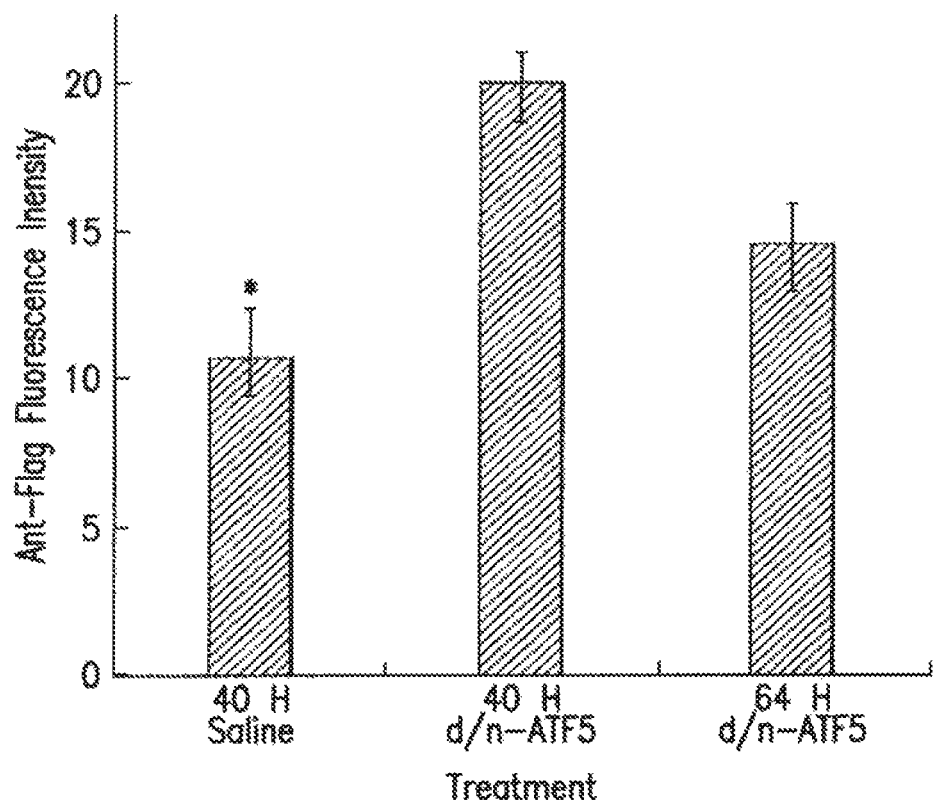
Figure 7A:
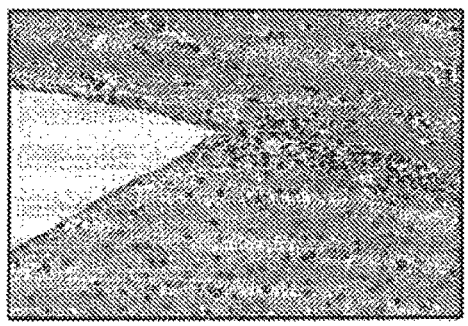
Figure 7A:
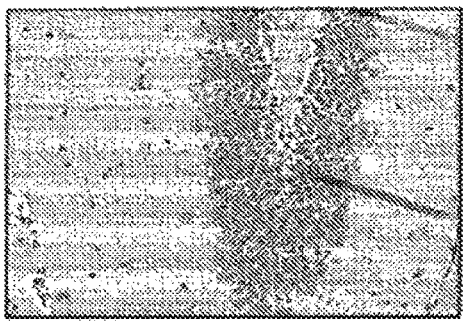
Figure 7B:
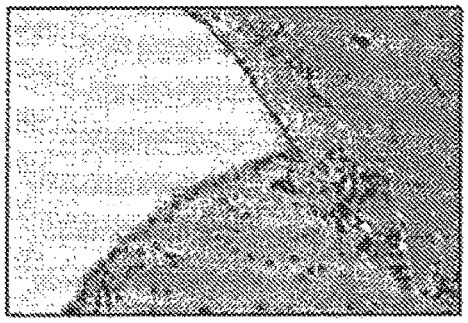
Figure 7B:
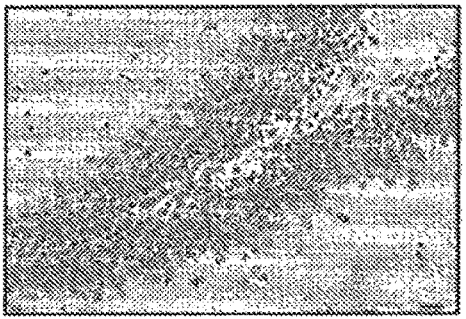
Figure 7C:
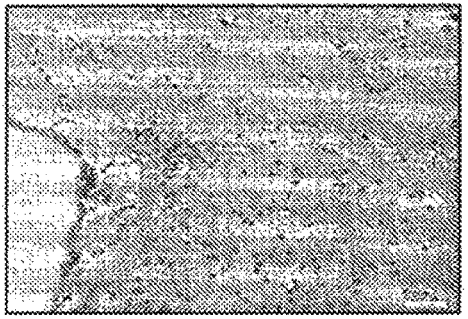
Figure 7C:
Figure 7D:
Figure 7D:
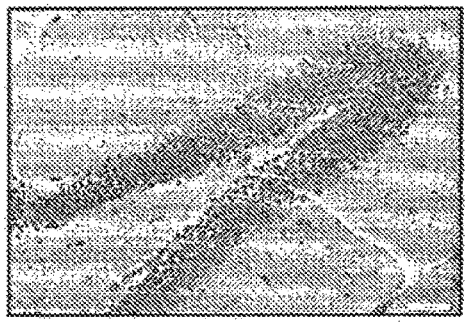

C6 cultures exposed to Pen-control-RP and Pen-d/n-ATF5-RP were also assessed for apoptotic cell death. The Pen-Control-RP treated cultures showed background levels of apoptotic death similar to that in non-treated cultures, whereas cultures treated with Pen-d/n-ATF5-RP showed greatly increased numbers of dying cells (FIG. 4). These actions are similar to what has been previously reported for multiple rodent and human glioblastoma cells transfected with d/n-ATF5 constructs or exposed to ATF5 siRNA [Angelastro et al., Oncogene 2006; 25(6):907-16; Arias et al., Oncogene 2012; 31(6):739-51; Sheng et al., Nat Med 2010; 16(6):671-7; Dluzen et al., The Journal of biological chemistry 2011; 286(9):7705-13].

Systemically-Delivered Pen-d/n-ATF5-RP Crosses the Blood Brain Barrier, Enters Cells and Selectively Triggers Rapid, Selective Apoptotic Death of Glioma Cells.

To test the capacity of Pen-d/n-ATF5-RP to reach and treat primary brain tumors, a model in which gliomas are generated by stereotactic injection of PDGF-B-HA/shRNA-p53 retrovirus into the adult mouse brain was used. The tumors are presumably derived from endogenous dividing progenitor cells and closely resemble infiltrative human gliomas ranging from stages II-IV. The tumors were detectable as early as 52 days post-injection by MRI (see below) and were histologically identifiable by the presence of the HA tag as well as by high cellularity, hyperchromatic nuclei, and elevated Ki67 staining.

In an initial set of experiments, Pen-d/n-ATF5-RP, saline or Pen-Control-RP was delivered intraperitoneally to tumor-bearing mice in a single set of four injections each of 1 mg/kg at intervals of 1-2 h. The mice were sacrificed 16-64 hours after the last injection and the fixed brains were stained with anti-Flag antibody to detect Pen-d/n-ATF5-RP or with anti-HA to mark PDGF-B-HA expressing tumor cells, and for TUNEL to identify dying cells. At 16 h, both tumor and normal brain cells (in the contralateral hemisphere from the tumor) showed Flag staining indicative of extensive uptake of Pen-d/n-ATF5-RP; there was no signal with saline injection (FIG. 5A-5C). Flag staining was still evident at 40 h after treatment and was detectable, though at reduced levels at 64 h (FIG. 6A-6D). While normal brain tissue showed no TUNEL staining (FIG. 5B), there was extensive TUNEL staining within the tumors one day after treatment with Pen-d/n-ATF5-RP (FIG. 5A). Little or no TUNEL signal was observed in tumors of animals treated with saline (FIG. 5C). Co-localized TUNEL and PDGF-B-HA+ tumor marker staining continued to be evident at 64 h after Pen-d/n-ATF5-RP treatment, but the signals indicated cell degeneration and fragmentation (FIG. 5E) compared with cells treated with this peptide for 16 h (FIG. 5A) or with Pen-Control-RP peptide (FIG. 5D).

To enhance the potential long-term therapeutic efficacy of Pen-d/n-ATF5-RP administration, a treatment protocol was devised in which tumor-bearing animals received two sets of subcutaneous injections, 5 days apart, each as described above. Tumors of mice assessed two days after the second treatment (7 days after initial treatment) showed patterns of HA and TUNEL staining, that, like 64 h after a single set of treatments, indicated cell degeneration and fragmentation (FIG. 5F).

Full body necropsy of non-tumor bearing animals one (n=2) or two days (n=2) after completion of the above dual treatment regimen revealed no evident pathological lesions to internal organs and no evident abnormalities of the cerebrum or cerebellum (FIG. 7A-7D' and Table 1). In addition, a liver-kidney serum chemistry panel carried out 1 day after the second set of Pen-d/n-ATF5-RP injections indicated no damage to either organ (Table 1; n=2).

TABLE 1

Results from gross necropsy of organs, H&E straining of tissue sections and liver-kidney function blood panel of mice treated with Pen-d/n-ATF5-RP.

| Gross Necropsy/ H&E slides | 1 day after Pen-d/n-ATF5-RP treatment #1 | 1 day after Pen-d/n-ATF5-RP treatment #2 | Control | 2 day after Pen-d/n-ATF5-RP treatment #1* | 2 day after Pen-d/n-ATF5-RP treatment #2* | 6 Month Post-tumor treatment with Pen-d/n-ATF5-RP #1 | 6 Month Post-tumor treatment with Pen-d/n-ATF5-RP #2 |
|---|---|---|---|---|---|---|---|
| Cerebrum, cerebellum, nasal cavity, liver, kidneys, spleen, pancreas, heart lungs, trachea, esophagus, thymus, salivary glands, GI tract, hind limb muscles, urinary bladder, reproductive tract | No gross lesion/No significant changes of pathological significance | No gross lesion/No significant changes of pathological significance | No gross lesion/No significant changes of pathological significance | No gross lesion/No significant changes of pathological significance | No gross lesion/No significant changes of pathological significance | No gross lesion/No significant changes of pathological significance | No gross lesion/No significant changes of pathological significance |

The indicated organs were collected from mice sacrificed at 1 day, 2 days and >6 months (190 days and 183 days, corresponding to mice with eradicated tumors in FIGS. 3A-3B, and FIGS. 8A-8F and FIGS. 11A-11E,) after the second of two sets of subcataneous treatments with Pen-d/n-ATF5-RP as described in the text. The >6 month animals had MRI-detected tumors before treatment and no histologically detectable tumors at the time of sacrifice. All other animals were not tumor-bearing. The control mouse was untreated. The organs were evaluated for gross pathological changes and then fixed, paraffin embedded and used for preparation of slide-mounted 5 μm sections. The slides were stained with H&E and examined microscopically for possible and pathological changes. Gross pathological analysis and evalution of sections were carried out by the Comparative Pathology TABLE 1-continued Laboratory at the UC Davis School of Veterinary Medicine. *Regional coagulative necrosis in the liver and focal linear pneumonia of the lung were observed due to inadvertent needle penetration during the injections.

| | Liver-Kidney function panel | | | | | | | | | |
|---|---|---|---|---|---|---|---|---|---|---|
| Mouse | Albumin g/dL | Alkaline Phosphatase U/L | Alanine Transaminase U/L | Aspartate Transaminase U/L | Blood Urea Nitrogen mg/dL | Creatinine mg/dL | Total Bilirubin mg/dL | Total Protein g/dL | Lipemia | Hemolysis |
| Male, one day after Pen-d/n-ATF5-RP treatment #1 | 3.95 | 52.9 | 55.4 | 128.7 | 20.4 | 0.072 | 0.089 | 5.87 | None | None |
| Male, one day after Pen-d/n-ATF5-RP treatment #2 | 3.35 | 46.0 | 21.6 | 66.6 | 19.7 | 0.061 | 0.115 | 5.21 | None | None |
| JAX database strain range (males) | 3.77 ± 0.247 | 78.3 ± 32.6 | 52.7 ± 19.6 | 152 ± 92.6 | 23.7 ± 3.47 | 0.167 ± 0.258 | 0.695 ± 0.167 | 6.10 ± 0.396 | Not Listed | Not Listed |

For liver-kidney function panel, blood samples were obtained were obtained 1 day after the second of two sets of subcataneous treatments with Pen-d/n-ATF5-RP as described in the text. The animals were not tumor-bearing. The analysis was carried out by the ComparativePathology Laboratory at the UC Davis School of Veterinary Medicine. The data for the strain (C57BL/6J) range was obtained from the Mouse Phenome Database at the Jackson Laboratory (http://phenome.jax.org/db/q?rtn=meas/catlister&req=Dblood--clinical%20chemistryqqq44&reqstrainid=7).

Systemically delivered Pen-d/n-ATF5-RP promotes rapid regression of mouse gliomas without recurrence as indicated by MRI and histology. Whether systemic administration of Pen-d/n-ATF5-RP promoted prolonged regression of gliomas in a mouse model was assessed. To achieve this MRI (post-contrast enhanced 3D FLASH T1 weighted) was used to assess tumors before and at various times after treatment with Pen-d/n-ATF5-RP, Pen-control-RP or no treatment. In many cases, the tumors were either multifocal or present in both hemispheres prior to treatment (FIG. 8A-8F, FIG. 9A-9E, FIG. 10, and FIG. 11A-11E). The peptides were injected subcutaneously using the two treatment protocol described above. Treatments commenced only after the presence of tumors was verified by MRI and were randomly assigned.

Figure 8A:
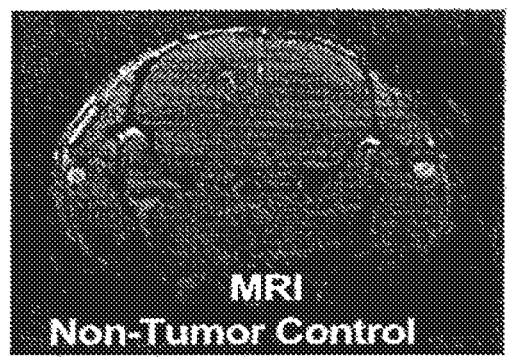
Figure 8B:
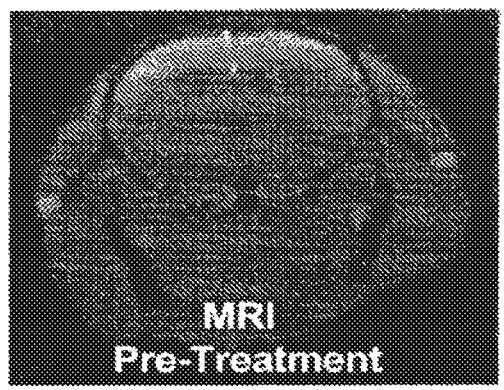
Figure 8C:
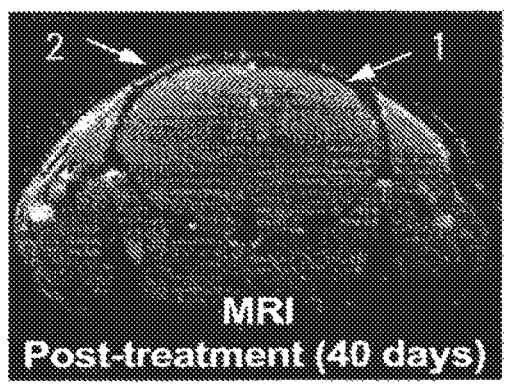
Figure 8D:
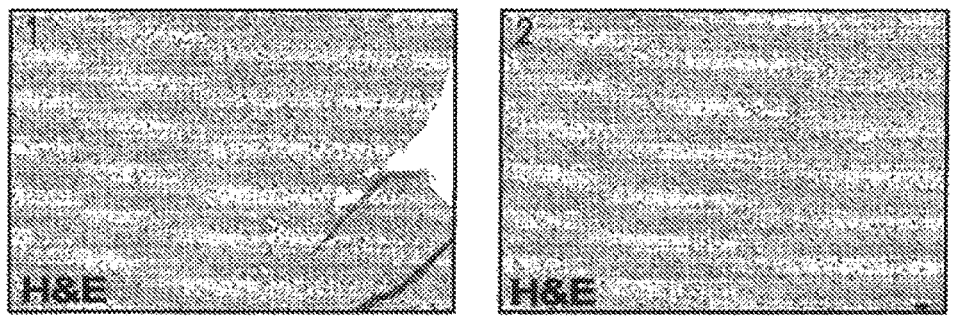
Figure 8E:
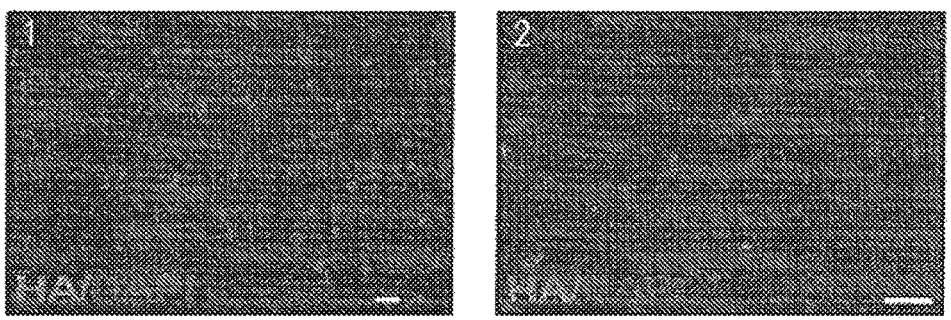
Figure 8F:
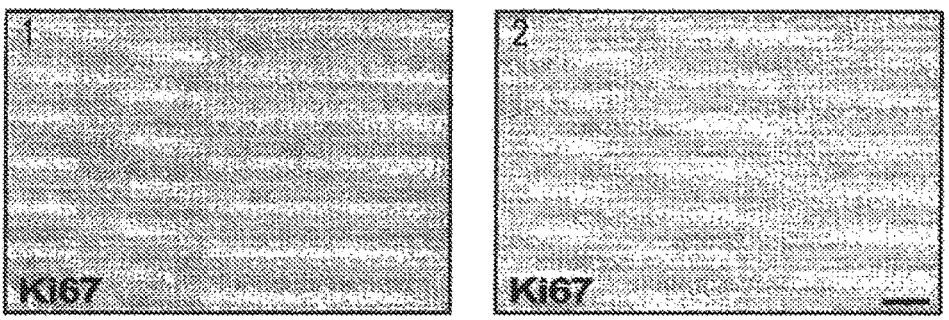
Figure 9A:
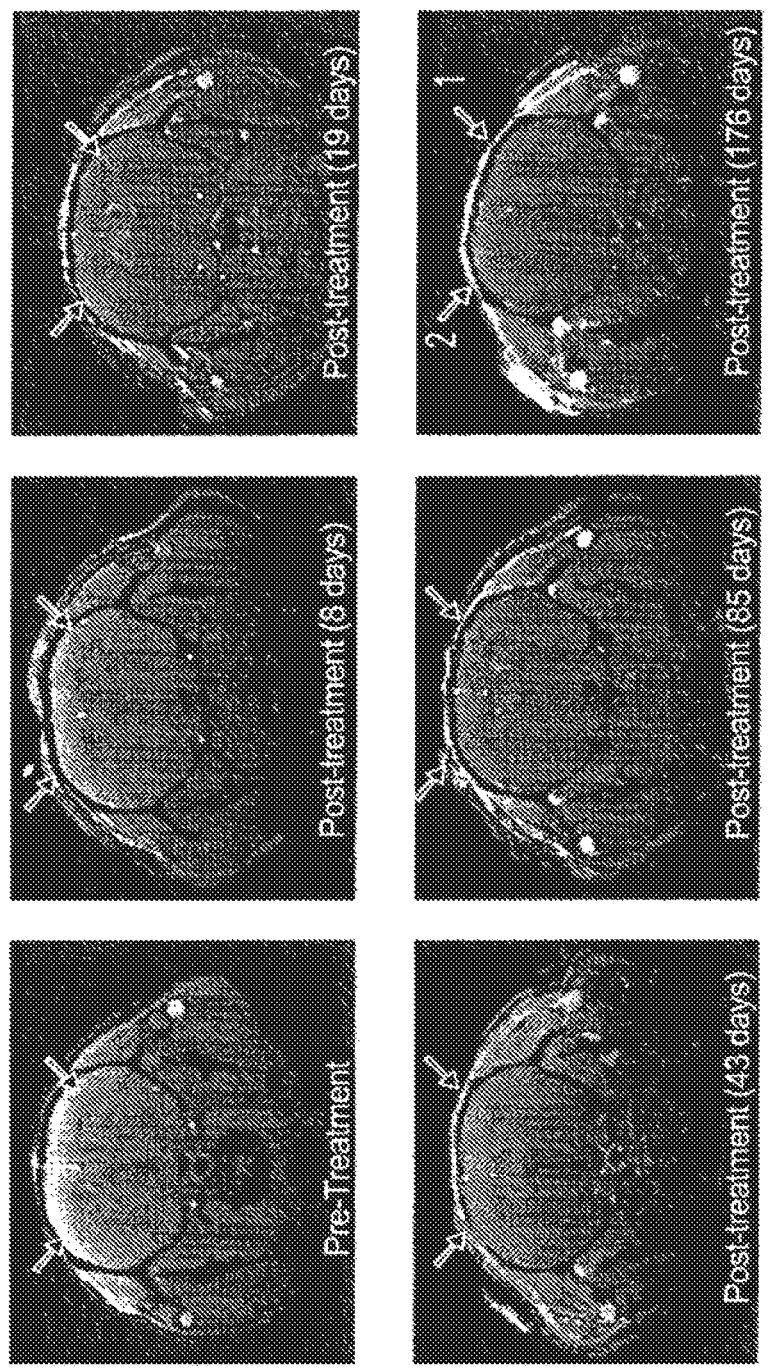
Figure 9B:
Figure 9D:
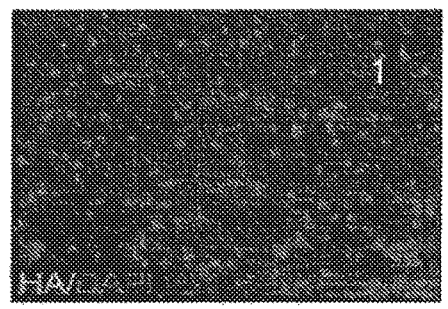
Figure 9C:
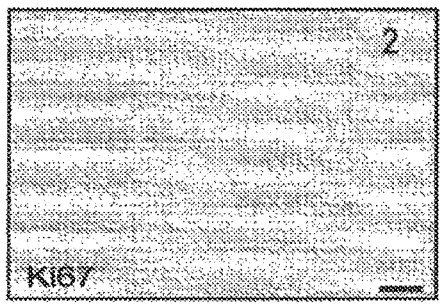
Figure 9E:
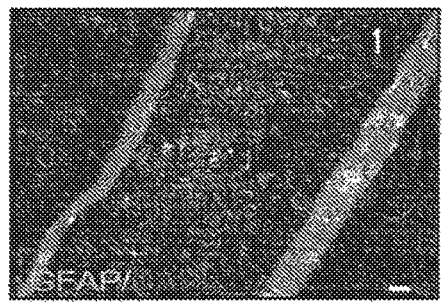

As anticipated, in no case was tumor regression observed as assessed by MRI in untreated animals (n=5) or animals treated with Pen-control-RP (n=4). A typical example for an animal treated with control peptide is shown in FIG. 8A-8F. Tumor presence was verified by histology on brains of animals those either died or were sacrificed after exhibiting moribund behavior or that survived beyond the study endpoint (6 months after MRI tumor detection). The tumors were HA+(FIG. 8E and FIG. 10), indicating the presence of the tagged PDGF-B and exhibited hyperchromatic nuclei (FIG. 8D) and elevated Ki67 staining typical of gliomas (FIG. 8F). The infiltrative tumor boundaries matched those in the MRI images (FIG. 8A-8F).

For mice treated with Pen-d/n-ATF5-RP, MRI revealed significant reduction (2/5; FIG. 9A-9E and FIG. 11A-11E) or un-detectability (3/5) of tumor signals at 8 days after treatment (the earliest time monitored) and full loss of detectable tumor signal within 3 weeks (n=7/7). When assessed by MRI at 176-225 days after peptide treatment, 7/7 mice assessed were tumor-free (see for example, FIG. 8A-8F, FIG. 11A-11E and FIG. 12B). Thus, Pen-d/n-ATF5-RP treatment appeared to rapidly clear gliomas without MRI-detectable recurrence for at least 6-7 months.

Postmortem histology (n=6; 183-259 days after treatment; 190-305 days after tumor detection) corroborated the MRI findings of tumor regression/eradication (FIG. 8A-8F, FIG. 11A-11E, and FIG. 12C). As in the rest of the brain, areas that initially had been tumor positive by MRI, showed an absence of hyperchromatic nuclei or high cellularity or elevated Ki67 staining (FIG. 8A-8F and FIG. 11A-11E). There was also no staining (other than scarce scattered single cells) for PDGF-B-HA+(FIG. 8A-8F and FIG. 11A-11E). There were however, foci of GFAP+ cells, suggesting glial activation and scarring in the areas where tumors had been present (FIG. 8A-8F and FIG. 11A-11E).

Figure 12A:
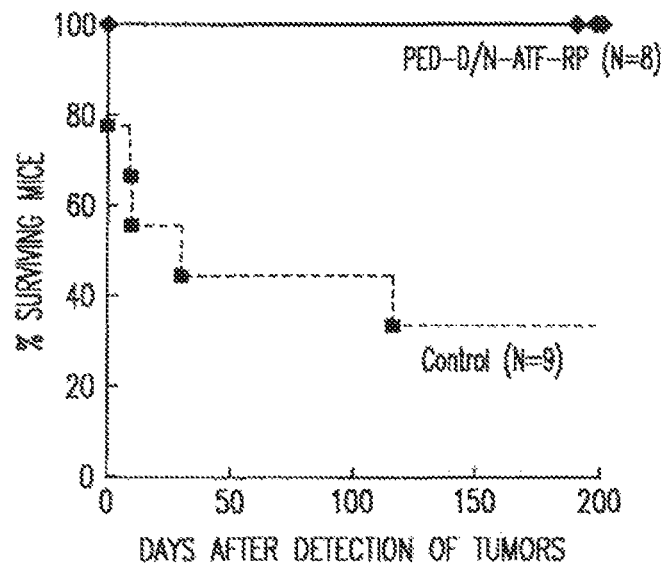
Figure 12B:
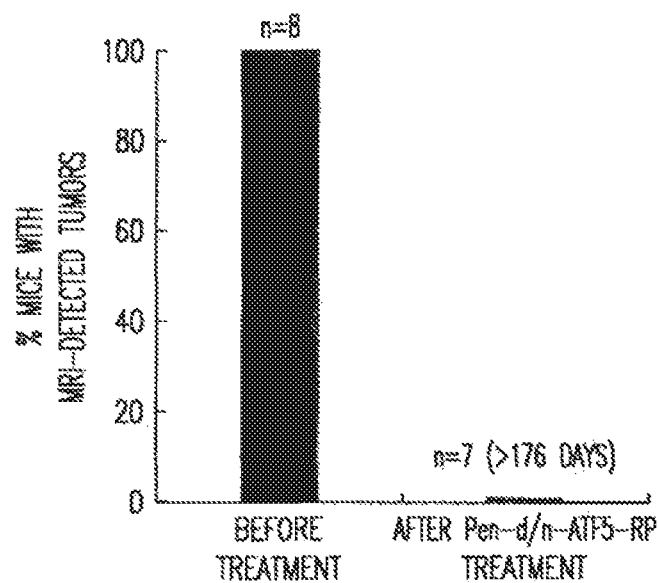
Figure 12C:
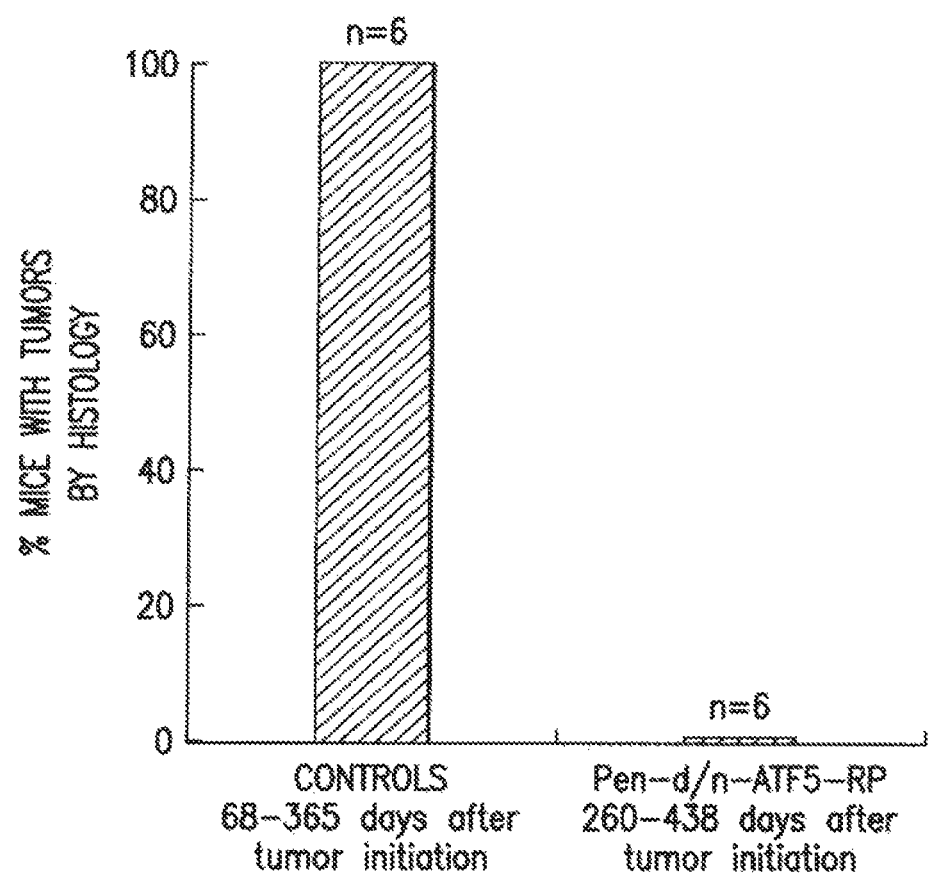

Systemically delivered Pen-d/n-ATF5-RP promotes long-term survival while maintaining normal brain and tissue integrity. All eight tumor-bearing mice treated with Pen-d/n-ATF5-RP survived to the nominal 180 day endpoint of the study after detection of tumors (FIG. 12A). In contrast, 6/9 control mice died within this time. In a past study 40% (n=16) of mice died within 180 days of tumor initiation [Arias et al., Oncogene 2012; 31(6):739-51].

In addition to the 6 mice that were sacrificed for histology at 6-8 months after Pen-d/n-ATF5-RP treatment, 2 animals have been maintained for a 12-month post-treatment time.

Other than the absence of tumors and the presence of glial scarring in areas of prior tumor localization, H&E staining of the brains of the animals sacrificed 6-8 months after Pen-d/n-ATF5-RP treatment indicated no evident abnormalities and both the subventricular and hippocampal subgranular zones appeared normal (FIG. 7A-7D'). Additionally, the weights of the treated mice prior to sacrifice were either within (4/6) or greater than (2/6) one standard deviation of the mean weight of age-matched controls given in the Mouse Phenome Database at the Jackson Laboratory (phenome.jax.org/db/q?rtn=strains/details&strainid=7). Two mice were also subjected to full body necropsy at >6 months of treatment (190 days and 183 days, corresponding to mice with eradicated tumors in FIG. 8A-8F and FIG. 11A-11E, respectively). No pathological changes were seen in any of the organs surveyed (Table 1).

5.1.3 Discussion

The findings presented herein show that Pen-d/n-ATF5-RP enters and promotes apoptotic activity in cultured GBM cells and that when systemically administered to animals, crosses the blood brain barrier, enters brain and tumor cells and causes massive tumor cell death and long-term tumor regression/eradication without apparent harm to normal tissues.

Another feature of the study presented herein was that the treated tumor-bearing animals survived for at least 6-12 months. By contrast, 2/3 of control animals died or showed morbidity within 189 days of tumor detection and all were tumor positive at death or at the 6 month point. Taken together, the results presented herein provide proof that a cell penetrating form of d/n-ATF5 can be used to treat malignant gliomas.

A model in which malignant gliomas were induced in adult mice by retrovirally expressed PDGF-B and p53 shRNA, presumably by transformation of PDGF-α-receptor+ neural progenitors and oligodendrocyte precursors, was used in the instant study. Such tumors resemble high grade human glioma [Arias et al., Oncogene 2012; 31(6):739-51] and, like the latter, are highly diffuse and relatively large and can invade both hemispheres. Given the wide expression of ATF5 in human GBMs and lower grade gliomas and the variety of human and rodent-derived GBM cell lines (with and without compromised p53 and PTEN) that express and require ATF5 for survival [Arias et al., Oncogene 2012; 31(6):739-51], it is expected that, based on the data presented herein, a range of malignant glioma cell types will be susceptible to treatment with cell-penetrating d/n-ATF5. Furthermore, although malignant gliomas are the focus of this study, it is significant to note that ATF5 is expressed by a wide variety of carcinomas [Sheng et al., Oncotarget 2010; 1(6):457-60; Chen A et al., International journal of gynecological pathology 2012; 31(6):532-7; Fernandez et al., Oncogene 2004; 23(29):5084-91.; Kong et al., Experimental and therapeutic medicine 2011; 2(5):827-831; Monaco et al., Int J Cancer 2007; 120(9):1883-90; and Hu et al., Anticancer research 2012; 32(10):4385-94], and that culture studies have shown apoptotic actions of d/n-ATF5 or ATF5 siRNA on tumor cells from a diverse range of tissues. [Sheng et al., Oncotarget 2010; 1(6):457-60; Chen A et al., International journal of gynecological pathology 2012; 31(6):532-7; Monaco et al., Int J Cancer 2007; 120(9):1883-90; and Hu et al., Anticancer research 2012; 32(10):4385-94]. Thus, based on the data presented herein, a diverse range of cancers will be susceptible to treatment with cell-penetrating d/n-ATF5.

An important aspect of the instant study was that although Pen-d/n-ATF5-RP promoted regression/eradication of tumors, it had no apparent adverse effects on normal tissue. It is significant that treated animals survived without apparent effect for at least 6-12 months and that no evident acute or long term tissue damage was observed. In addition, any potential negative effects of Pen-d/n-ATF5-RP may be mitigated by the limited duration of treatment.

Figure 10:
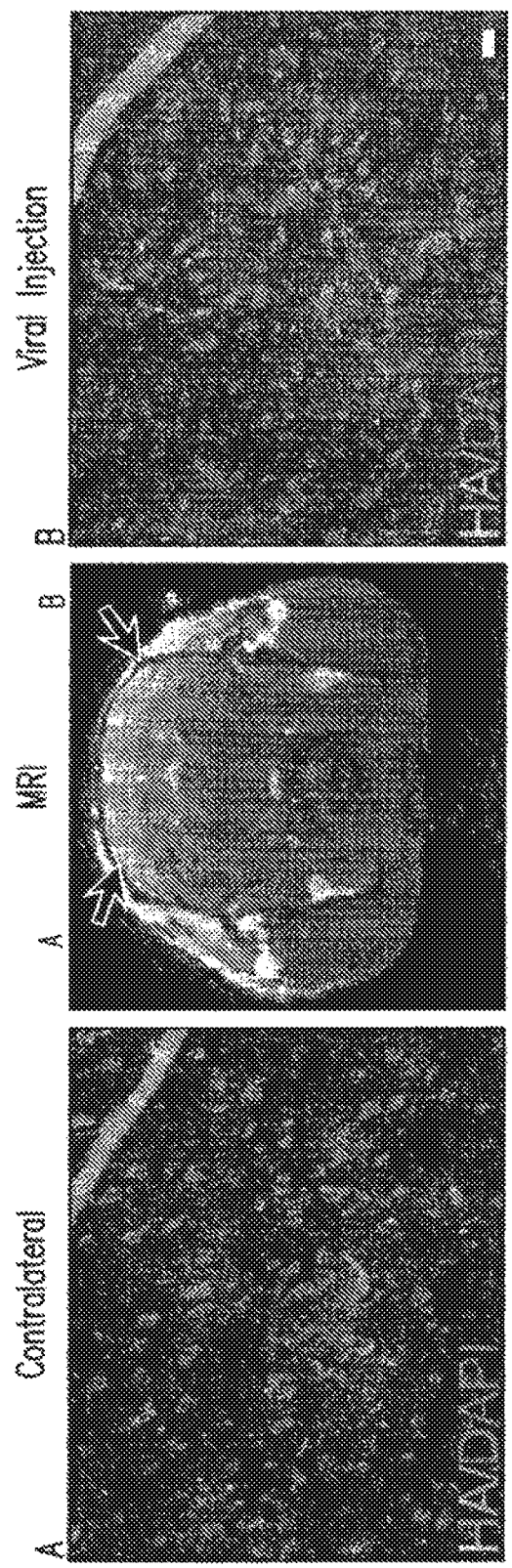
Figure 13:
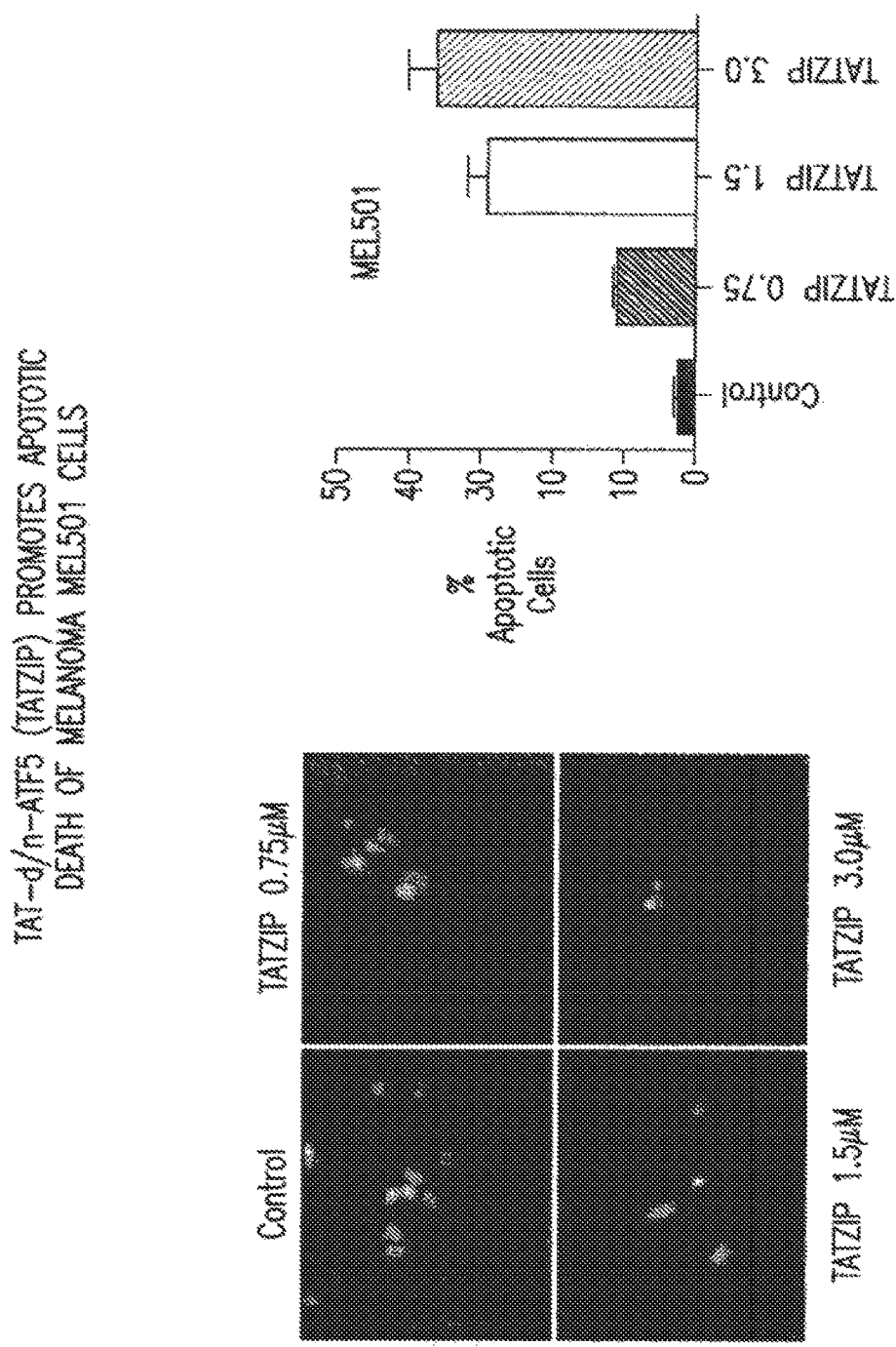

5.2 Addition Cell Lines and CP-d/n-ATF5 Compositions 5.2.1 TAT-d/n-ATF5 Promotes Apoptotic Death of Cultured Melanoma MEL501 Cells TAT-linked dominant-negative ATF5 peptide was added to medium of MEL501 melanoma cells at the concentrations (in μM) indicated in FIG. 13. Four days later the cells were stained with Hoescht dye and the cells were stained for proportion with apoptotic nuclei. As illustrated in FIG. 10, TAT-d/n/ATF5 promoted apoptosis in a dose-dependent fashion.

Figure 14:
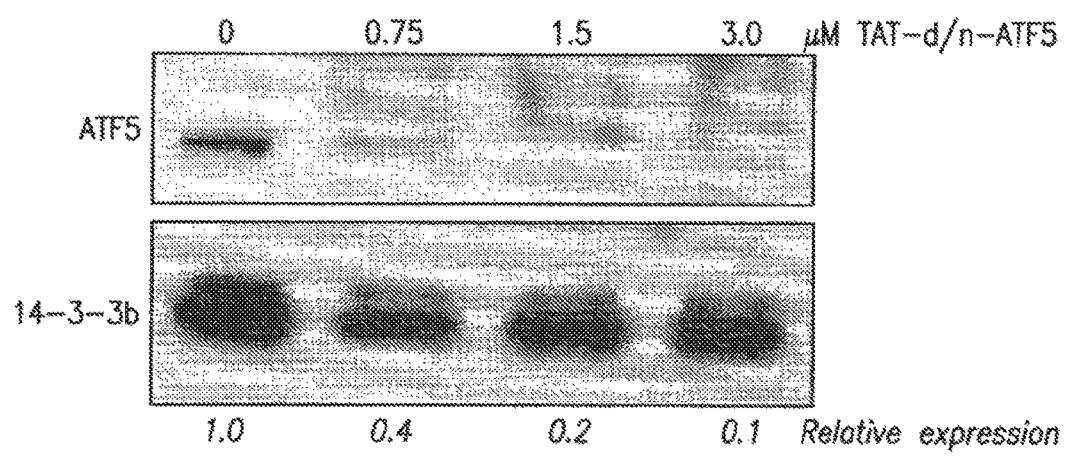

5.2.2 TAT-d/n-ATF5 Reduces Expression of Endogenous ATF5 in Cultured U373 Glioblastoma Cells TAT-linked dominant-negative ATF5 peptide was added to medium of U373 glioblastoma cells at the concentrations (in μM) indicated in FIG. 14 for 17 hrs day and the cells were then harvested and analyzed by Western immunoblotting for levels of endogenous ATF5. Note that the TAT-d/n-ATF5 greatly reduces expression of endogenous ATF5. As previous studies have shown that tumor cells require endogenous ATF5 to survive, but without being bound by theory, the mechanism of action by which the cell-penetrating TAT-ZIP peptide kills may be by causing loss of the endogenous ATF5 protein. Note also the smear above the endogenous ATF5 when the TAT-ZIP peptide is present. This suggests that TAT-ZIP reduces endogenous ATF5 by causing its ubiquitination and proteasomal degradation.

5.2.3 TAT-d/n-ATF5 Induces Expression of the Pro-Death Gene DDIT3

Figure 15:
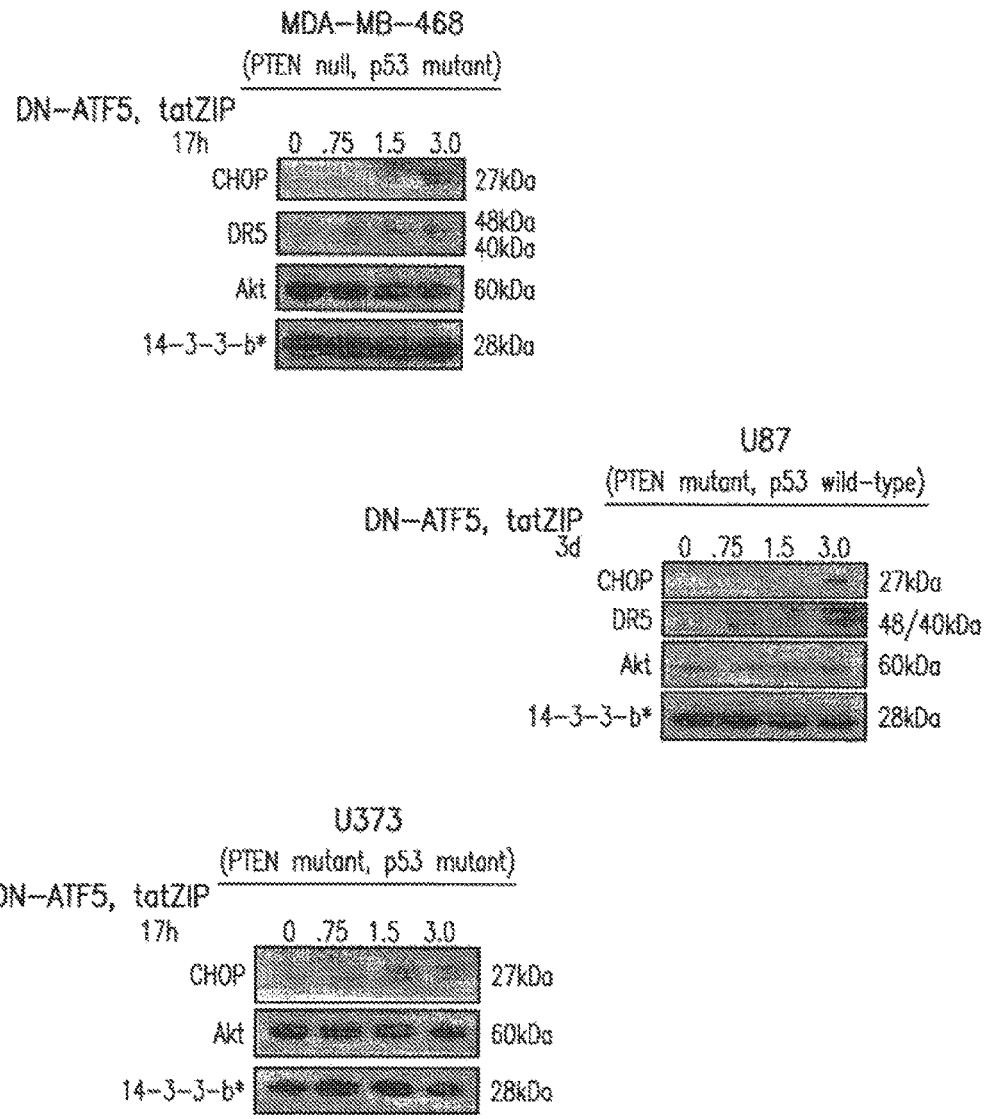

TAT-d/n-ATF5 (TAT-ZIP) peptide induces expression of the pro-death gene DDIT3 (CHOP) in various tumor cell lines. Cells were treated with TAT-d/n-ATF5 for the times and doses (in μM) indicated in FIG. 15 and then harvested and analyzed by Western immunoblotting for expression of CHOP and other non-responsive proteins. Note the elevation of CHOP in all cases. Since CHOP may promote cell death, these data indicate that induction of CHOP protein may be one mechanism by which TAT-d/n-ATF5 kills tumor cells.

5.2.4 Silencing of CHOP Protein with siRNA Partially Protects U87 Cells from TAT-d/n-ATF5

Figure 16:
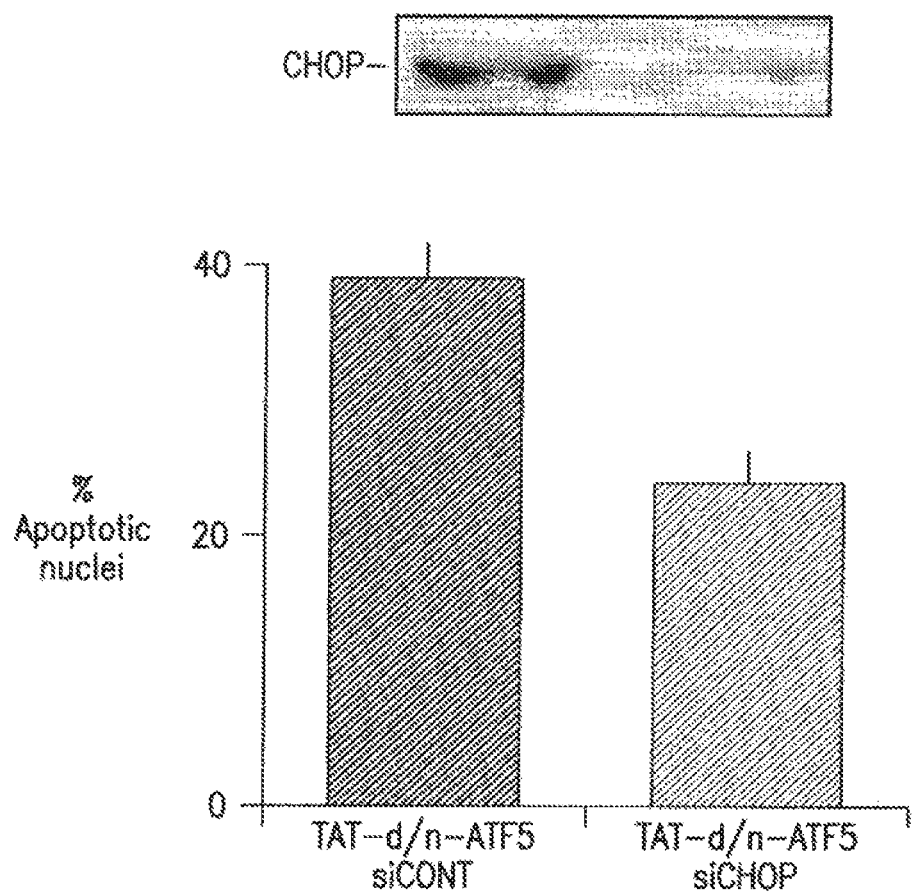

Silencing of CHOP protein with siRNA (top Western immunoblot of FIG. 16) partially protects U87 cells from death caused by TAT-d/n-ATF5 peptide. Cells were treated with siCHOP to silence CHOP expression (top Western immunoblot of FIG. 16) or with control siRNA. They were then exposed to TAT-d/n-ATF5 for 2 days and assessed for proportion of cells with apoptotic nuclei. The data indicate that part of the mechanism by which TAT-d/n-ATF5 kills tumor cells is by increasing their expression of CHOP which in turn mediates death.

5.2. TAT-D/N-ATF5 Down-Regulates BCL2 Survival Protein

Figure 17:
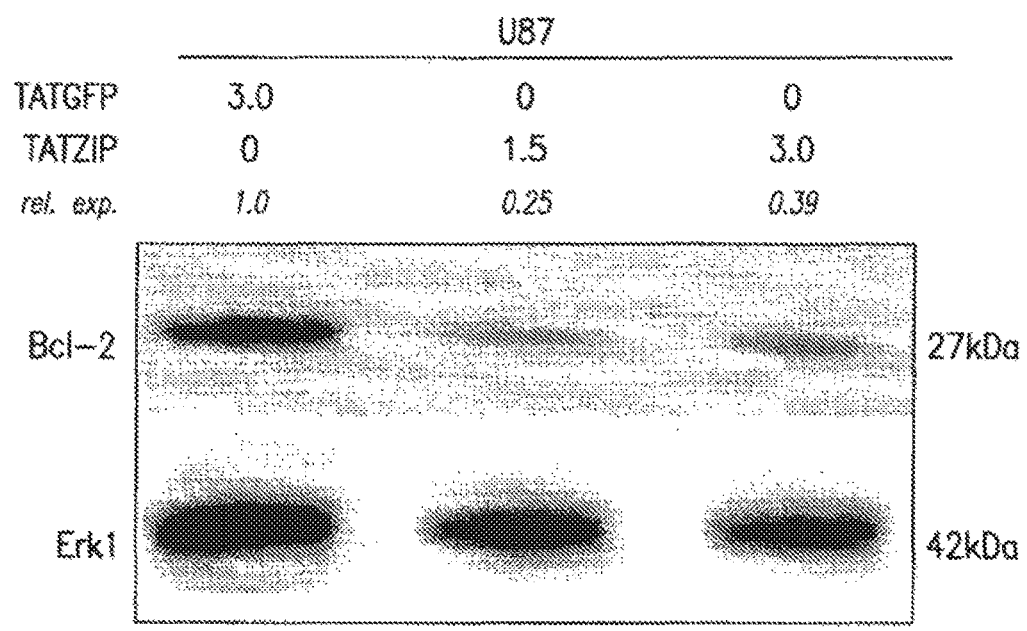

TAT-D/N-ATF5 down-regulates BCL2 survival protein. As outlined in FIG. 17, cultured U87 human glioblastoma cells were treated with the indicated concentrations of TATZIP (TAT-d/n-ATF5 peptide) (in μM) for 30 hrs. The cells were then harvested and assessed by Western immunoblotting for expression of the survival protein BCL2. These findings indicate that in addition to elevating pro-death CHOP, TAT-d/n-ATF5 may also kill tumor cells by reducing their levels of the BCL2 survival protein.

Figure 18:
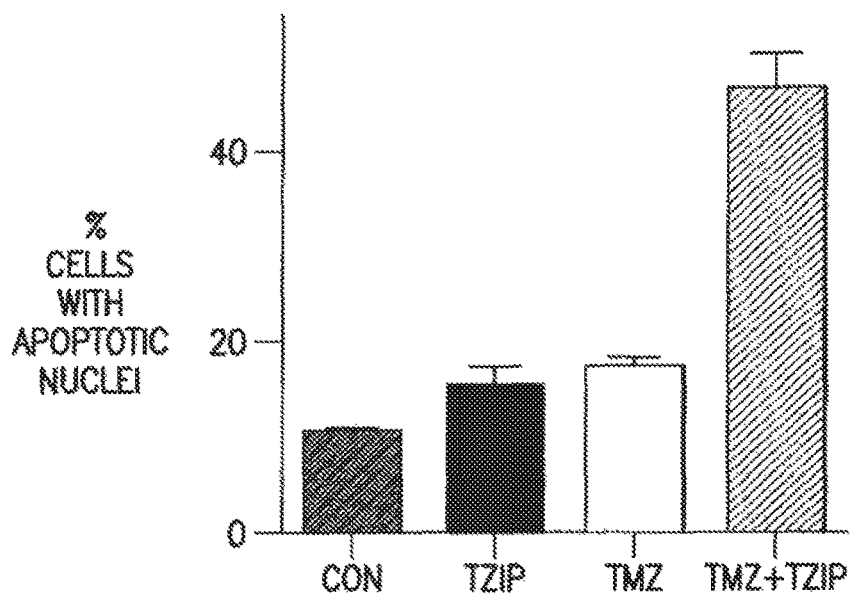

5.9 TAT-D/N-ATF5 Synergizes with Temozolomide to Kill Cultured U87 Glioblastoma Cells TAT-D/N-ATF5 synergizes with temozolomide (TMZ) to kill cultured U87 glioblastoma cells. As outlined in FIG. 18, cells were cultured for one day with sub-lethal levels of TAT-d/n-ATF5 (TZIP 1 μM) and TMZ (50 μM) either separately or in combination, and then assessed for proportion of cells with apoptotic nuclei. TMZ is presently the first-line treatment for human GBM. The data reveal that TAT-d/n-ATF5 not only functions in presence of TMZ, but that the two drugs act in synergy to kill GBM cells. This indicates that TAT-d/n-ATF5 can be administered to patients who are taking TMZ.

5.10 TAT-D/N-ATF5 Decreases Viability of U87, U373, and MSG Cells

Figure 19:
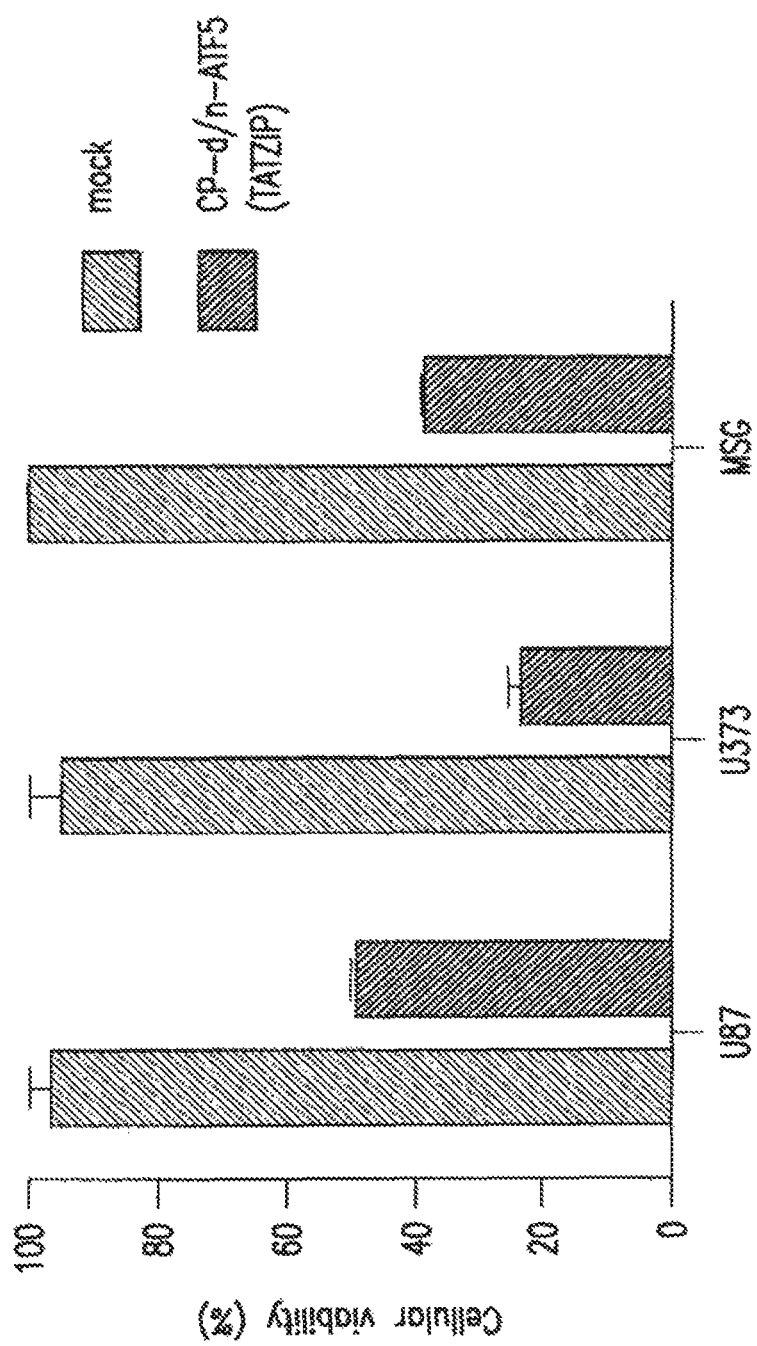
FIG. 19 depicts recombinant TAT-d/n-ATF5 (3 μM) treatment for 3-5 days decreasing viability of two human and one mouse GMB cell line as established by MTA assay.

As outlined in FIG. 19, recombinant TAT-d/n-ATF5 (3 μM) treatment for 3-5 days decreases viability of two human and one mouse GMB cell line as detected using an MTA assay.

5.11 Synthetic PEN-D/N-ATF5 Decreases Viability of U87 Cells

Figure 20:
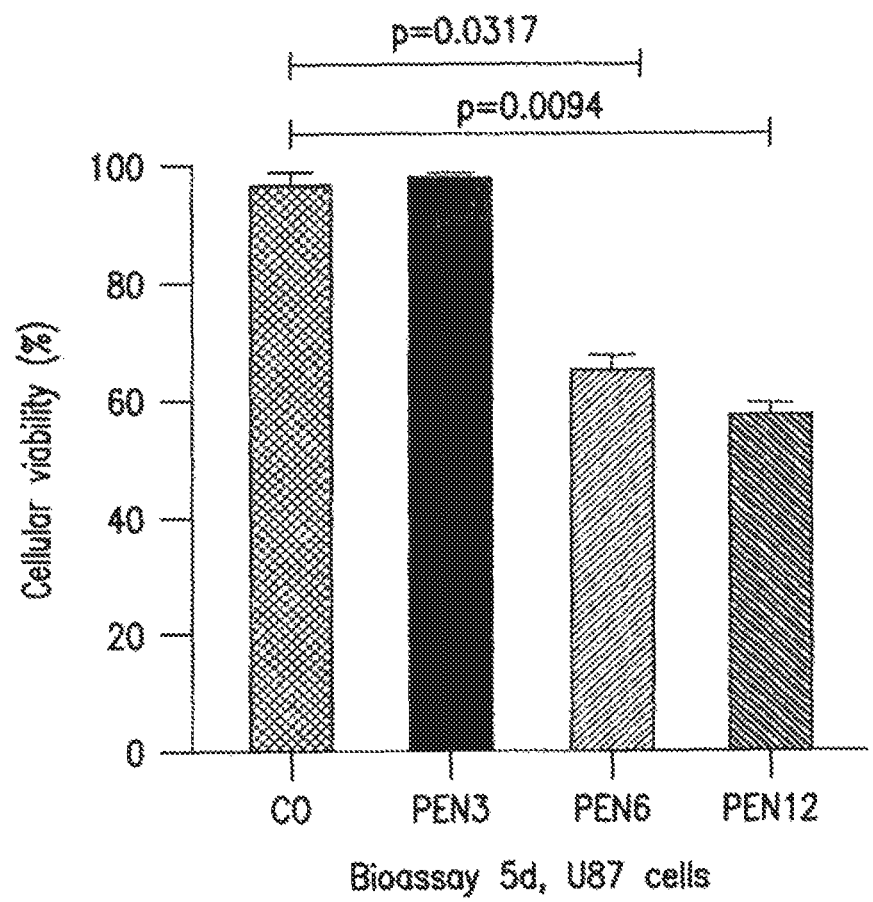
FIG. 20 depicts synthetic PEN-d/n-ATF5 treatment decreasing cell viability of cultured U87 human glioblastoma cells as established by MTA assay. 5 days treatment at indicated concentrations (μM).

As outlined in FIG. 20, synthetic PEN-d/n-ATF5 decreases cell viability of cultured U87 human glioblastoma cells. 5 days treatment at indicated concentrations (μM), as detected using an MTA assay.

5.12 TAT-D/N-ATF5 Promotes Cell Death of U87 Cells

As outlined in FIG. 21, Recombinant TAT-d/n-ATF5 promotes death of cultured U87 human glioblastoma cells as indicated by Annexin V/PI staining and flow cytometry. Proportions of viable cells are shown in lower left quadrant (88% control vs 58% treated). Dying cell proportions are in the lower right and upper right quadrants (9% in controls vs 36% in treated).

5.13 Synthetic PEN-D/N-ATF5 Promotes Apoptosis of GS9-6 Cells

As outlined in FIG. 22, Synthetic PEN-d/n-ATF5 promotes apoptotic death of primary GS9-6 human glioblastoma stem cells growing in culture as spheres. Data reflects 6 days of treatment. Data determined by Annexin V/PI staining and flow cytometry.

5.13 Recombinant PEN-D/N-ATF5 Promotes Apoptosis of GS9-6 Cells

As outlined in FIG. 23, Recombinant PEN-d/n-ATF5 promotes apoptotic death of primary GS9-6 human glioblastoma stem cells growing in culture as spheres. 5 days treatment. Data determined by Annexin V/PI staining and flow cytometry.

Various publications are cited herein, the contents of which are hereby incorporated by reference in their entireties.

---

The invention claimed is:

1. A cell-penetrating dominant-negative ATF5 molecule consisting essentially of: (i) a cell-penetrating peptide sequence selected from the group consisting of RQIKIWFQNRRMKWKK (SEQ ID NO: 34), YGRKKRRQRRR (SEQ ID NO: 40), and GRKKRRQRRRPPQ (SEQ ID NO: 41); (ii) a dominant-negative ATF5 sequence selected from the group consisting of LEQENAE (SEQ ID NO: 1), LEKEAEELEQENAE (SEQ ID NO: 2), LARENEELLEKEAEELEQENAE (SEQ ID NO: 3), and LEQRAEELARENEELLEKEAEELEQENAE (SEQ ID NO: 4); (iii) an ATF5 leucine zipper sequence selected from the group consisting of LEGECQGLEARNRELKERAESV (SEQ ID NO: 26), LEGECQGLEARNRELRERAESV (SEQ ID NO: 32), LEGECQGLEARNRELKERAES (SEQ ID NO: 53), and LEGECQGLEARNRELRERAES (SEQ ID NO: 54); and optionally (iv) one or more tags for isolation, purification, and/or identification.

2. The molecule of claim 1, wherein the cell-penetrating peptide sequence is RQIKIWFQNRRMKWKK (SEQ ID NO: 34).

3. The molecule of claim 1, wherein the cell-penetrating peptide sequence is YGRKKRRQRRR (SEQ ID NO: 40).

4. The molecule of claim 1, wherein the cell-penetrating peptide sequence is GRKKRRQRRRPPQ (SEQ ID NO: 41).

5. The molecule of claim 1, wherein the dominant-negative ATF5 sequence is LEQENAE (SEQ ID NO: 1).

6. The molecule of claim 1, wherein the dominant-negative ATF5 sequence is LEKEAEELEQENAE (SEQ ID NO: 2).

7. The molecule of claim 1, wherein the dominant-negative ATF5 sequence is LARENEELLEKEAEELEQENAE (SEQ ID NO: 3).

8. The molecule of claim 1, wherein the dominant-negative ATF5 sequence is LEQRAEELARENEELLEKEAEELEQENAE (SEQ ID NO: 4).

9. The molecule of claim 1, wherein the ATF5 leucine zipper sequence is LEGECQGLEARNRELKERAESV (SEQ ID NO: 26).

10. The molecule of claim 1, wherein the ATF5 leucine zipper sequence is LEGECQGLEARNRELRERAESV (SEQ ID NO: 32).

11. The molecule of claim 1, wherein the ATF5 leucine zipper sequence is LEGECQGLEARNRELKERAES (SEQ ID NO: 53).

12. The molecule of claim 1, wherein the ATF5 leucine zipper sequence is LEGECQGLEARNRELRERAES (SEQ ID NO: 54).

13. The molecule of claim 1, having a sequence selected from the group consisting of:

```
(i)
                               (SEQ ID NO: 18)
MGSSHHHHHHSSGLVPRGSHMRQIKIWFQNRRMKWKKLEQRAEE
LARENEELLEKEAEELEQENAELEGECQGLEARNRELKERAESV;

(ii)
                               (SEQ ID NO: 19)
RQIKIWFQNRRMKWKKLEQRAEELARENEELLEKEAEELEQENAEL
EGECQGLEARNRELKERAESV;

(iii)
                               (SEQ ID NO: 55)
MGSSHHHHHHSSGLVPRGSHMRQIKIWFQNRRMKWKKLEQRAEE
LARENEELLEKEAEELEQENAELEGECQGLEARNRELRERAESV;
and (iv)
                               (SEQ ID NO: 52)
RQIKIWFQNRRMKWKKLEQRAEELARENEELLEKEAEELEQENAEL
EGECQGLEARNRELRERAESV;
``` wherein the underlined residues (MG-HM) are the tag for isolation and/or purification, the bolded residues (RQ-KK) are the cell-penetrating peptide, the italicized residues (LE-AE) are the dominant-negative ATF5 sequence, and the bolded underlined residues (LE-SV) are the ATF5 leucine zipper sequence.

14. A composition comprising the cell-penetrating dominant-negative ATF5 molecule of claim 1.

15. The composition of claim 14, wherein the composition is a pharmaceutical composition.

16. A kit comprising the cell-penetrating dominant-negative ATF5 molecule of claim 1.

17. The kit of claim 16, wherein the cell-penetrating dominant-negative ATF5 molecule is in a pharmaceutically acceptable carrier.

18. A nucleic acid molecule encoding the cell-penetrating dominant-negative ATF5 molecule of claim 1.

19. A method of treating a tumor in a subject, the method comprising administering to the subject an effective amount of the molecule of claim 1, wherein the tumor is selected from the group consisting of a neural tumor, melanoma, mesothelioma, breast cancer, pancreatic cancer, colon carcinoma, and prostate cancer.

20. The method of claim 19, wherein the tumor is a neural tumor.

21. The method of claim 20, wherein the neural tumor is a glioma.

22. The method of claim 20, wherein the neural tumor is a glioblastoma.

23. The method of claim 20, wherein the neural tumor is neuroblastoma.

24. The method of claim 19, further comprising administering to the subject a second therapeutic agent.

25. The method of claim 20, further comprising administering to the subject temozolomide.

26. The method of claim 19, wherein administration is oral, parenteral, intranasal, or transdermal.

27. The method of claim 26, wherein the parenteral administration is intracranial, intrathecal, intramuscular, intraperitoneal, intravenous, or subcutaneous.

28. A method of promoting apoptosis in a neoplastic cell, the method comprising contacting the neoplastic cell with the molecule of claim 1.

29. The method of claim 28, wherein the neoplastic cell is selected from the group consisting of breast, ovary, endometrium, gastric, colon, liver, pancreas, kidney, bladder, prostate, testis, skin, esophagus, tongue, mouth, parotid, larynx, pharynx, lymph node, blood, lung, peripheral nervous system, and brain.

30. The method of claim 28, wherein the neoplastic cell is selected from the group consisting of glioblastoma, astrocytoma, glioma, medulloblastoma, meningioma, mesothelioma, and neuroblastoma.

* * * * *